(12) United States Patent
Harada

(10) Patent No.: US 11,839,355 B2
(45) Date of Patent: Dec. 12, 2023

(54) ENDOSCOPE

(71) Applicant: FUJIFILM Corporation, Tokyo (JP)

(72) Inventor: Takashi Harada, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 477 days.

(21) Appl. No.: 16/932,837

(22) Filed: Jul. 20, 2020

(65) Prior Publication Data

US 2020/0345210 A1    Nov. 5, 2020

Related U.S. Application Data

(63) Continuation of application No. PCT/JP2019/002535, filed on Jan. 25, 2019.

(30) Foreign Application Priority Data

Feb. 23, 2018    (JP) ................................ 2018-031048

(51) Int. Cl.
*A61B 1/00* (2006.01)
*A61B 1/018* (2006.01)

(52) U.S. Cl.
CPC ........ *A61B 1/00098* (2013.01); *A61B 1/0014* (2013.01); *A61B 1/00052* (2013.01);
(Continued)

(58) Field of Classification Search
CPC ............ A61B 1/00098; A61B 1/00101; A61B 1/00135; A61B 1/00142; A61B 1/005;
(Continued)

(56) References Cited

U.S. PATENT DOCUMENTS 5,460,168 A    10/1995    Masubuchi et al.
5,569,157 A *  10/1996    Nakazawa ......... A61B 1/00177
                                                              600/106
(Continued)

FOREIGN PATENT DOCUMENTS

EP    1759626    5/2013
JP    H05253177  10/1993
(Continued)

OTHER PUBLICATIONS

"International Search Report (Form PCT/ISA/210) of PCT/JP2019/002535," dated Apr. 9, 2019, with English translation thereof, pp. 1-4.
(Continued)

*Primary Examiner* — Ryan N Henderson
(74) *Attorney, Agent, or Firm* — JCIPRNET

(57) ABSTRACT

There is an endoscope that allows operations for attaching and detaching the proximal end of a wire to and from an elevating operation mechanism to be easily performed, can reduce the influence of variations of the length of a soft part and the length of an operation wire, and can adjust an operating range of an elevating operation lever for an elevator. The endoscope includes: an operation unit that is provided with an operation member; an insertion unit that is provided on a distal end side of the operation unit and is to be inserted into an object to be examined; a treatment tool-elevator that is provided in a distal end part of the insertion unit; a rotating body that is disposed to be exposed to an outside of the operation unit and operates in conjunction with an operation of the operation member; a movable member that is attachably and detachably connected to the rotating body; a position adjustment member that is capable of adjusting a connection position of the movable member in a rotation direction of the rotating body; an elevating operation wire, of which a distal end side is connected to the
(Continued)

treatment tool-elevator and a proximal end side is connected to the movable member and which causes the treatment tool-elevator to operate by being pushed or pulled according to an operation of the movable member; and a mounting member that is provided at a proximal end of the elevating operation wire and is attachably and detachably engaged with the movable member.

16 Claims, 32 Drawing Sheets

(52) U.S. Cl.
CPC ...... *A61B 1/00101* (2013.01); *A61B 1/00133* (2013.01); *A61B 1/018* (2013.01); *A61B 1/00066* (2013.01)

(58) Field of Classification Search
CPC ............... A61B 1/0051; A61B 1/0052; A61B 1/0053; A61B 1/0055; A61B 1/0056; A61B 1/0057; A61B 1/0058; A61B 1/008; A61B 1/00137; G02B 23/24; G02B 23/2476
USPC ........................................................ 600/107
See application file for complete search history.

(56) References Cited

U.S. PATENT DOCUMENTS

| | | | |
|---|---|---|---|
| 7,846,090 B2 | 12/2010 | Pilvisto et al. | |
| 10,357,145 B2* | 7/2019 | Fukushima | A61B 1/00098 |
| 10,856,724 B2* | 12/2020 | Miller | A61B 1/0676 |
| 11,019,984 B2* | 6/2021 | Miller | A61B 1/0676 |
| 11,484,186 B2* | 11/2022 | Harada | A61B 1/00002 |
| 2007/0270638 A1* | 11/2007 | Kitano | A61B 1/00098 600/114 |
| 2007/0287887 A1* | 12/2007 | Maruyama | G02B 23/2476 600/146 |
| 2008/0319264 A1* | 12/2008 | Maruyama | A61B 1/0052 600/146 |
| 2016/0206180 A1* | 7/2016 | Hosogoe | A61B 8/0841 |
| 2016/0270630 A1* | 9/2016 | Tanaka | A61B 1/00098 |
| 2016/0270633 A1* | 9/2016 | Iwasaka | A61B 1/00098 |
| 2016/0270634 A1* | 9/2016 | Tanaka | A61B 1/00098 |
| 2016/0270635 A1* | 9/2016 | Tanaka | A61B 1/00098 |
| 2016/0270636 A1* | 9/2016 | Iwasaka | A61B 1/00137 |
| 2016/0270637 A1* | 9/2016 | Tanaka | A61B 1/00098 |
| 2017/0000317 A1* | 1/2017 | Iizuka | A61B 1/0615 |
| 2017/0020370 A1* | 1/2017 | Yamaya | A61B 1/00142 |
| 2017/0112362 A1* | 4/2017 | Morimoto | A61B 1/00096 |
| 2017/0238789 A1* | 8/2017 | Iizuka | A61B 1/018 |
| 2018/0092512 A1* | 4/2018 | Hiraoka | A61B 1/00 |
| 2018/0185045 A1* | 7/2018 | Ohki | A61B 1/009 |
| 2018/0206708 A1* | 7/2018 | Miller | A61B 1/00177 |
| 2018/0249894 A1* | 9/2018 | Kolberg | A61B 1/00137 |
| 2018/0279857 A1* | 10/2018 | Miller | A61B 1/00142 |
| 2019/0223697 A1* | 7/2019 | Hosogoe | A61B 1/00101 |
| 2019/0223698 A1* | 7/2019 | Hosogoe | A61B 1/00098 |
| 2020/0178767 A1* | 6/2020 | Miller | A61B 1/015 |
| 2020/0178773 A1* | 6/2020 | Miller | A61B 1/00098 |
| 2020/0214544 A1* | 7/2020 | Harada | A61B 1/00101 |
| 2020/0315428 A1* | 10/2020 | Harada | A61B 1/00112 |
| 2020/0337530 A1* | 10/2020 | Miller | A61B 1/00089 |
| 2020/0345210 A1* | 11/2020 | Harada | A61B 1/00066 |
| 2020/0352418 A1* | 11/2020 | Hayakawa | A61B 1/00098 |
| 2021/0106213 A1* | 4/2021 | Yamasaka | A61B 1/018 |
| 2021/0244264 A1* | 8/2021 | Schulz | A61B 1/00066 |
| 2022/0202278 A1* | 6/2022 | Melito | G05G 5/06 |

FOREIGN PATENT DOCUMENTS

| | | | |
|---|---|---|---|
| JP | H06315458 | 11/1994 | |
| JP | 07047052 A * | 2/1995 | ......... A61B 1/00096 |
| JP | H0747052 | 2/1995 | |
| JP | 07184830 A * | 7/1995 | ......... A61B 1/00098 |
| JP | H07184830 | 7/1995 | |
| JP | H08243076 | 9/1996 | |
| JP | 2010136737 | 6/2010 | |
| JP | 2014128465 | 7/2014 | |
| JP | 2017148096 | 8/2017 | |
| JP | 2017148406 | 8/2017 | |

OTHER PUBLICATIONS

"Written Opinion of the International Searching Authority (Form PCT/ISA/237) of PCT/ JP2019/002535," dated Apr. 9, 2019, with English translation thereof, pp. 1-18.
"Office Action of Japan Counterpart Application" with English translation thereof, dated Sep. 14, 2021, p. 1-p. 8.
Office Action of China Counterpart Application, with English translation thereof, dated Dec. 21, 2022, pp. 1-14.

* cited by examiner

FIG. 19
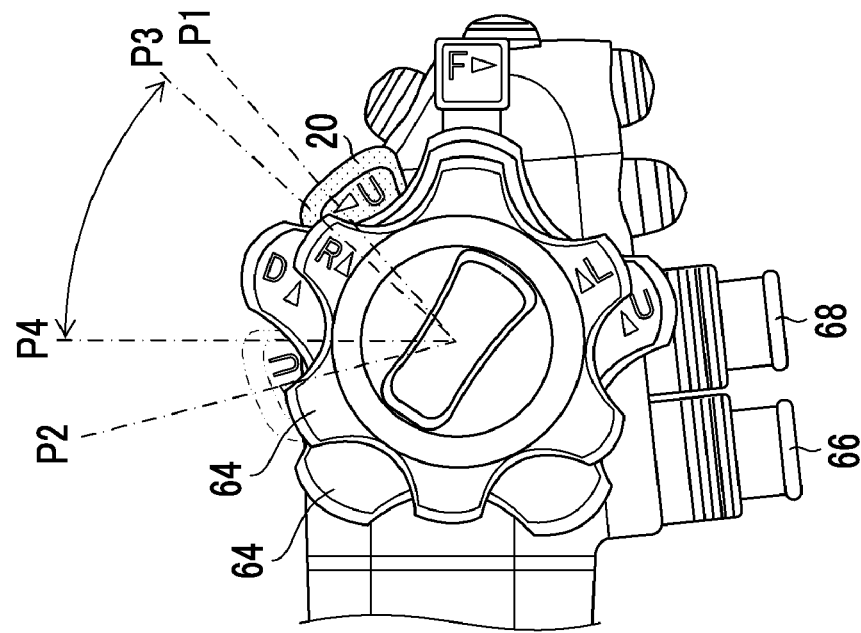
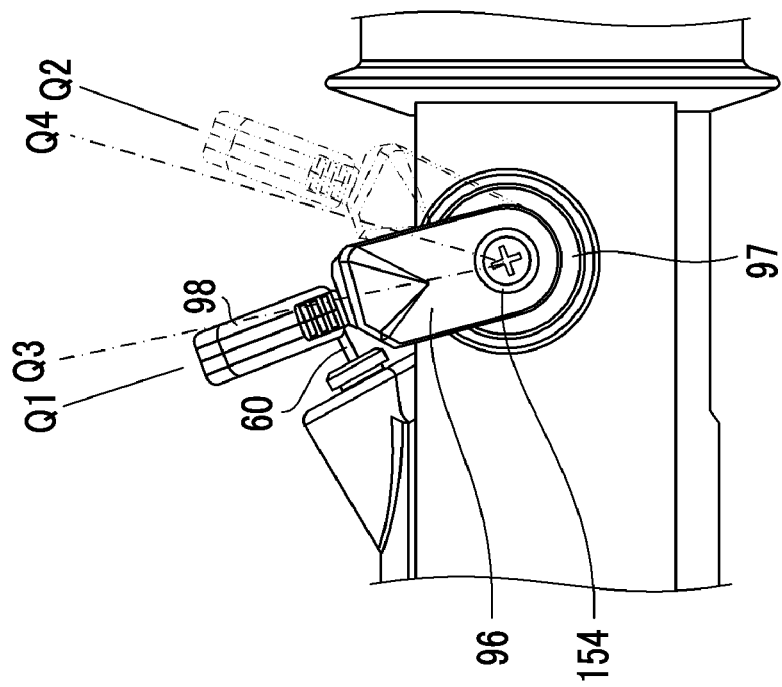

FIG. 30
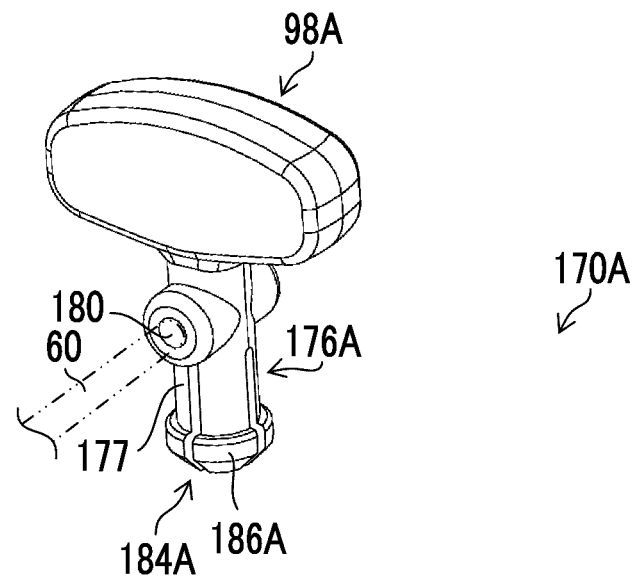
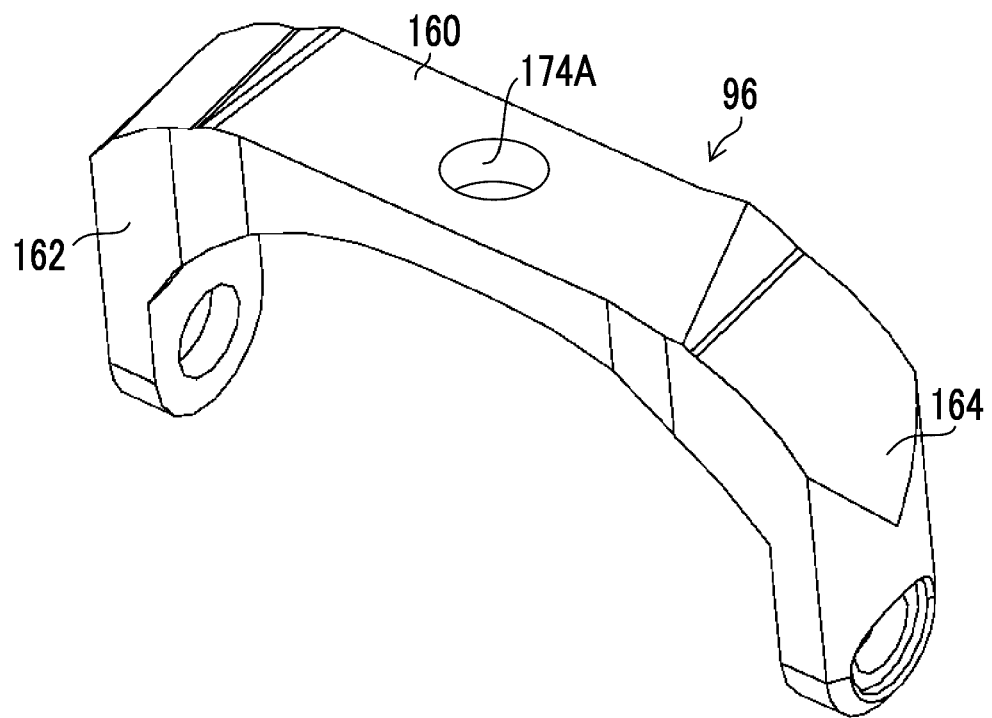

FIG. 34
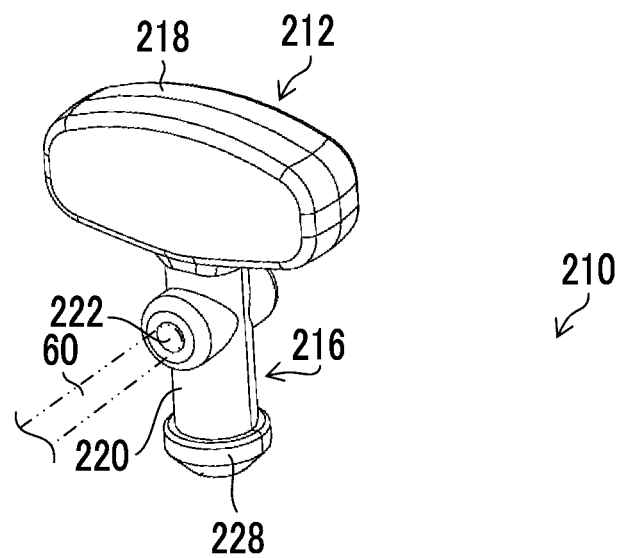
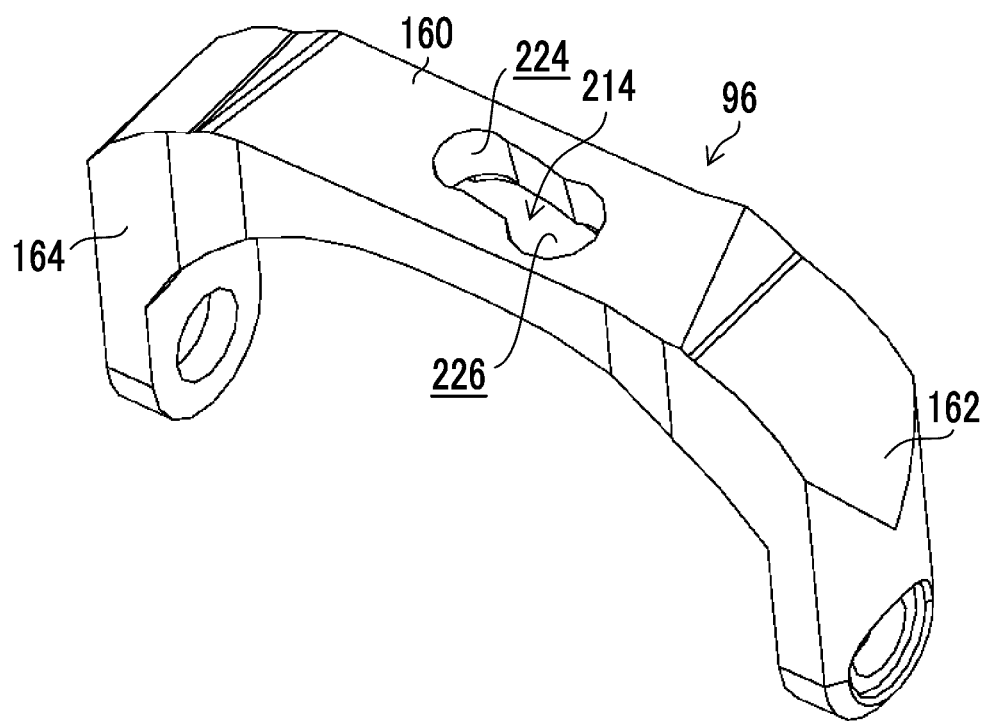

FIG. 37
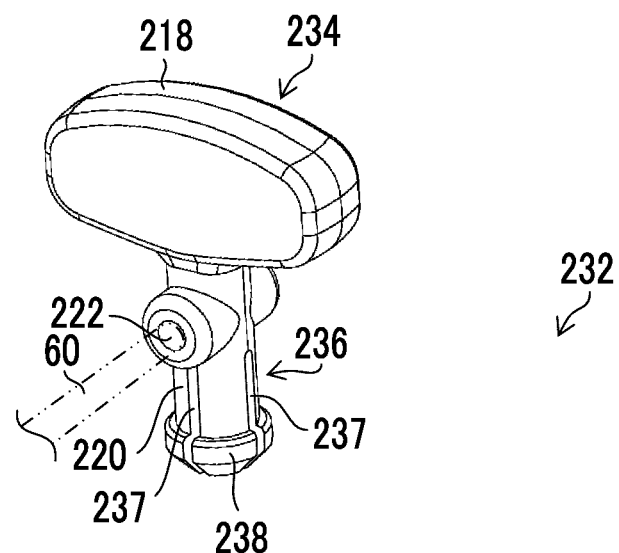
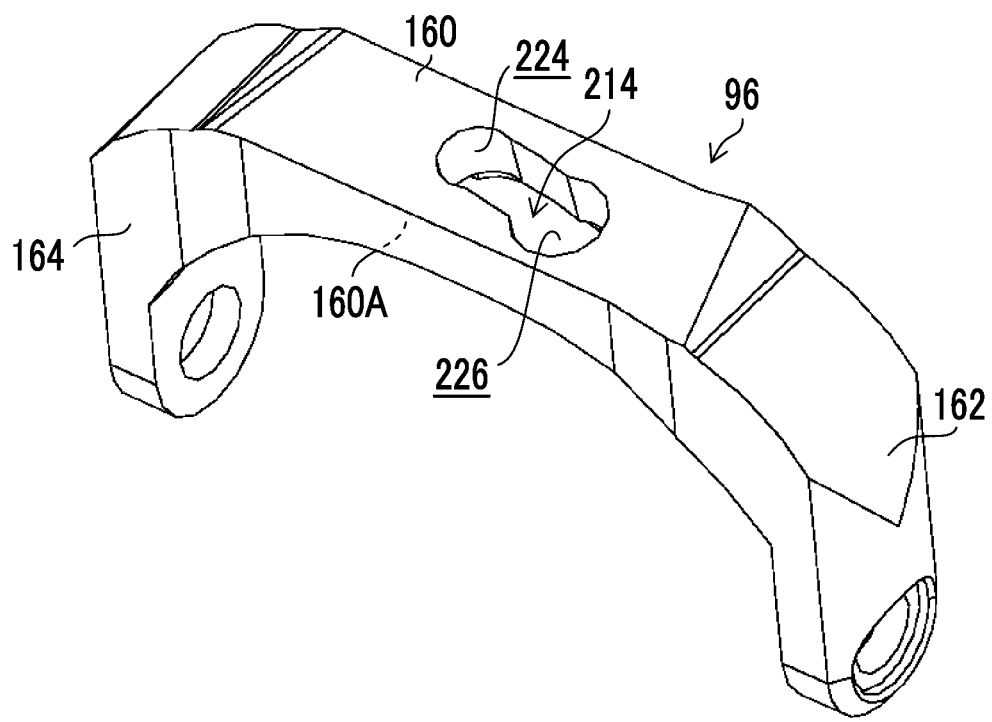

ENDOSCOPE

CROSS-REFERENCE TO RELATED APPLICATIONS

The present application is a Continuation of PCT International Application No. PCT/JP2019/002535 filed on Jan. 25, 2019 claiming priority under 35 U.S.C § 119(a) to Japanese Patent Application No. 2018-031048 filed on Feb. 23, 2018. Each of the above applications is hereby expressly incorporated by reference, in its entirety, into the present application.

BACKGROUND OF THE INVENTION

1. Field of the Invention

The present invention relates to an endoscope, and more particularly, to an endoscope that comprises, at a distal end part of an insertion unit, a treatment tool-elevator for changing a lead-out direction of a treatment tool.

2. Description of the Related Art

In an endoscope, various treatment tools are introduced through a treatment tool inlet provided on a hand operation unit (hereinafter referred to as an "operation unit"), are led out of a treatment tool outlet opened to a distal end member of the insertion unit to the outside, and are used for treatment. For example, a treatment tool, such as forceps or a contrast tube, is used in a duodenoscope, and a treatment tool, such as a puncture needle, is used in an ultrasound endoscope. The lead-out direction of such a treatment tool, which is led out of the treatment tool outlet, needs to be changed to perform treatment at a desired position in an object to be examined. For this purpose, the distal end member is provided with a treatment tool-elevator (hereinafter referred to as an "elevator"), and the endoscope is provided with a treatment tool-elevating mechanism that changes the attitude of the elevator between an elevated position and a fallen position.

A wire pulling mechanism where the distal end portion of a wire (also referred to as a forceps-elevating wire) is directly mounted on an elevator is known as the treatment tool-elevating mechanism (see JP1994-315458A (JP-H06-315458A)). In this mechanism, the proximal end side of a wire is connected to an elevating operation lever (also referred to as a forceps-elevating lever) provided on an operation unit and the elevator is rotated about a rotational movement shaft to change the attitude thereof between an elevated position and a fallen position in a case where the wire is pushed or pulled by the elevating operation lever.

More specifically, the operation unit disclosed in JP1994-315458A (JP-H06-315458A) is provided with a grip part, which is used to hold the operation unit with a hand, and angle knobs. In the operation unit, a wire opening portion is provided below the grip part, a drive shaft opening portion is provided at the grip part, the proximal end of the wire is led out of the wire opening portion, and the distal end of a drive shaft, which is moved by the forceps-elevating lever, is led out of the drive shaft opening portion. The distal end of the drive shaft and the proximal end of the wire are detachably connected to a connection tool, and the operation unit is attachably and detachably provided with a protective cover covering the connection tool.

Incidentally, in a case where an endoscope is used for various examinations or treatments, body cavity liquid adheres to the distal end member of the insertion unit including the elevator and a guide pipe into which the wire is to be inserted. For this reason, after being used, the endoscope is washed and disinfected using a washing solution and an antiseptic solution. In that case, since the diameter of the guide pipe is small and the wire is inserted into the guide pipe, time and effort are required for washing.

Accordingly, the endoscope disclosed in JP1994-315458A (JP-H06-315458A) is attachably and detachably provided with a cover, which covers the distal end member of the insertion unit, the elevator, and the wire; and the cover, the elevator, and the wire are detached and the distal end member of the insertion unit and the guide pipe for the wire are then washed.

Further, EP1759626B discloses an endoscope where the proximal end of a cable cord is led out of the proximal end of a control handle and a collet is connected to the proximal end of the cable cord. The collet is fastened to a nut and is moved in a front-rear direction by an operation lever.

SUMMARY OF THE INVENTION

Incidentally, there is considerable assembly tolerance of an endoscope and considerable tolerance of components. Particularly, the variations of the length of a soft part of an insertion unit and the length of an operation wire for operating an elevator affect the operability of the elevating operation lever.

The invention has been made in consideration of such circumstances, and an object of the invention is to provide an endoscope that can reduce the influence of variations of the length of a soft part and the length of an operation wire and can adjust the operating range of an elevating operation lever for an elevator.

In order to achieve the object of the invention, an endoscope according to a first aspect comprises: an operation unit that is provided with an operation member; an insertion unit that is provided on a distal end side of the operation unit and is to be inserted into an object to be examined; a treatment tool-elevator that is provided in a distal end part of the insertion unit; a rotating body that is disposed to be exposed to an outside of the operation unit and operates in conjunction with an operation of the operation member; a movable member that is attachably and detachably connected to the rotating body; a position adjustment member that is capable of adjusting a connection position of the movable member in a rotation direction of the rotating body; an elevating operation wire, of which a distal end side is connected to the treatment tool-elevator and a proximal end side is connected to the movable member and which causes the treatment tool-elevator to operate by being pushed or pulled according to an operation of the movable member; and a mounting member that is provided at a proximal end of the elevating operation wire and is attachably and detachably engaged with the movable member.

According to a second aspect, in the endoscope, the position adjustment member includes a housing portion that is provided in the movable member and houses at least a part of the rotating body, and a fixing screw that fixes positions of the rotating body housed in the housing portion and the movable member.

According to a third aspect, in the endoscope, the position adjustment member includes a grip portion that is provided at the movable member and grips at least a part of the rotating body and a fastening screw that fastens a distal end portion of the grip portion and fixes positions of the rotating body and the movable member.

According to a fourth aspect, in the endoscope, the position adjustment member includes an outer peripheral groove that is provided on at least a part of the rotating body, a housing portion which is provided in the movable member and on which an inner peripheral groove to be engaged with the outer peripheral groove is formed, and a fixing screw that fixes positions of the rotating body housed in the housing portion and the movable member.

According to a fifth aspect, in the endoscope, any one of the movable member or the mounting member is provided with an engaging hole and the other thereof is provided with an engaging portion to be attachably and detachably engaged with the engaging hole.

According to a sixth aspect, in the endoscope, the engaging portion is provided with an elastically deformable portion that is elastically deformed to be engaged with the engaging hole.

According to a seventh aspect, in the endoscope, a pair of elastically deformable claw portions to be locked to an edge portion of the engaging hole is formed at the elastically deformable portion, and the pair of claw portions is displaced so as to approach each other through elastic deformation in a case where the engaging hole and the engaging portion are engaged with each other or disengaged from each other.

According to an eighth aspect, in the endoscope, the engaging portion includes a cylindrical portion to be inserted into the engaging hole, and the elastically deformable portion is formed of a slotted portion provided at a distal end portion of the cylindrical portion, and the slotted portion is adapted to be elastically deformed to be capable of being reduced in diameter in a case where the distal end portion of the cylindrical portion is inserted into the engaging hole.

According to a ninth aspect, in the endoscope, the engaging hole includes a narrow portion having a first width and a wide portion having a second width larger than the first width, and the engaging portion includes a shaft portion that has an outer diameter equal to or smaller than the first width, and an enlarged-diameter portion that is provided at a distal end of the shaft portion and has an outer diameter larger than the first width and smaller than the second width.

According to a tenth aspect, in the endoscope, the engaging hole includes a narrow portion having a first width and a wide portion having a second width larger than the first width; the engaging portion includes a shaft portion that has an outer diameter equal to or smaller than the first width, and an enlarged-diameter portion that forms the elastically deformable portion, is provided at a distal end of the shaft portion, has an outer diameter larger than the second width, and includes a plurality of slotted grooves; and the enlarged-diameter portion is adapted to be elastically deformed due to the plurality of slotted grooves to be capable of being reduced in diameter in a case where the enlarged-diameter portion is inserted into the wide portion.

According to an eleventh aspect, in the endoscope, the engaging hole includes a friction resistance portion that is in contact with an outer peripheral surface of the shaft portion to apply frictional resistance to the shaft portion in a case where the shaft portion is moved between the narrow portion and the wide portion.

According to a twelfth aspect, in the endoscope, any one of the movable member or the mounting member is provided with a cylindrical body extending in a direction perpendicular to an axial direction of the elevating operation wire and the other thereof is provided with an annular body to be rotatably engaged with an outer periphery of the cylindrical body, and the endoscope comprises a rotation-regulating stopper that regulates relative rotation of the cylindrical body and the annular body.

According to a thirteenth aspect, the endoscope further comprises an engaging member that is provided at a distal end of the elevating operation wire and a housing groove that is provided in the treatment tool-elevator and is attachably and detachably engaged with the engaging member.

According to a fourteenth aspect, the endoscope further comprises a proximal end opening that is provided in the operation unit, a distal end opening that is provided in the distal end part, and an elevating operation wire channel that is provided in the insertion unit and allows the proximal end opening and the distal end opening to communicate with each other. The elevating operation wire is inserted into the elevating operation wire channel, a distal end side of the elevating operation wire is connected to the treatment tool-elevator disposed outside the distal end opening, and a proximal end side of the elevating operation wire is connected to the movable member disposed outside the proximal end opening.

According to a fifteenth aspect, in the endoscope, the movable member is provided to be rotatable about a direction, which is perpendicular to an axial direction of the elevating operation wire, as a rotation axis.

According to a sixteenth aspect, in the endoscope, the operation member is an operation member that is rotatably supported on the operation unit. The endoscope further comprises a first conversion mechanism that converts rotary motion of the operation member into linear motion, a drive member that is linearly driven by the first conversion mechanism, and a second conversion mechanism that converts linear motion of the drive member into rotary motion to rotate the movable member.

According to a seventeenth aspect, in the endoscope, the second conversion mechanism includes a speed reducer.

According to the invention, it is possible to provide an endoscope that can reduce the influence of variations of the length of a soft part and the length of an operation wire and can adjust the operating range of an elevating operation lever for an elevator.

BRIEF DESCRIPTION OF THE DRAWINGS

FIG. 19 is a diagram showing the operating ranges of an elevating operation lever and the movable member.

FIG. 30 is a diagram showing a modification example of the connection structure.

FIG. 31 is a cross-sectional view of main portions of the connection structure shown in

FIG. 30.

FIG. 34 is an exploded perspective view of the connection structure shown in FIG. 33.

FIG. 35 is a cross-sectional view of main portions of the connection structure shown in

FIG. 33.

FIG. 37 is an exploded perspective view of a connection structure of a third aspect.

DESCRIPTION OF THE PREFERRED EMBODIMENTS

An endoscope according to a preferred embodiment of the invention will be described below with reference to the accompanying drawings.

Figure 1:
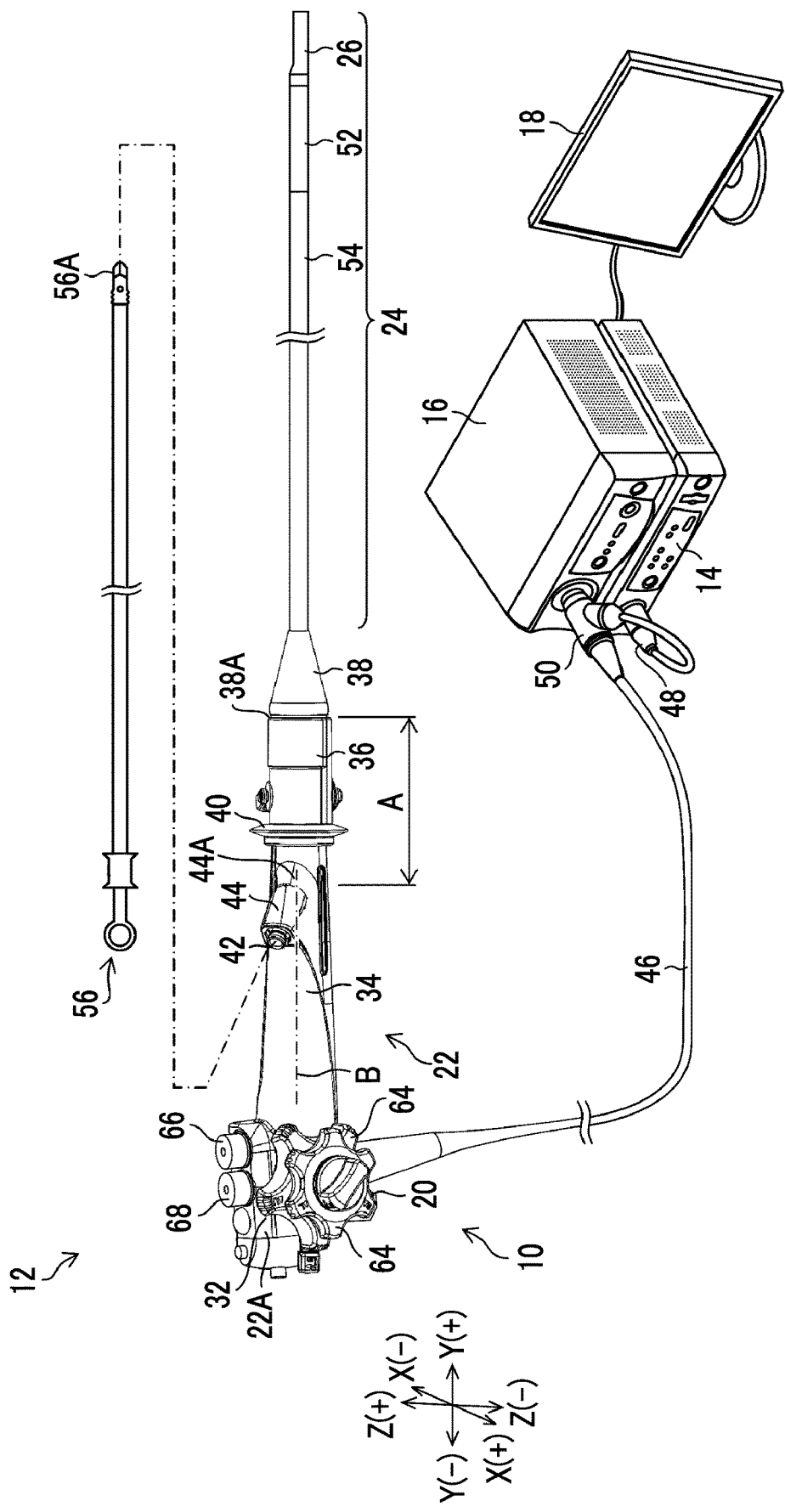
FIG. 1 is a diagram showing the configuration of an endoscope system comprising an endoscope according to an embodiment.

FIG. 1 is a diagram showing the configuration of an endoscope system 12 comprising an endoscope 10 according to an embodiment of the invention. The endoscope system 12 comprises an endoscope 10, a processor device 14, a light source device 16, and a display 18. A treatment tool 56 to be used for the endoscope system 12 is also shown in FIG. 1.

The endoscope 10 comprises an operation unit 22 that comprises an elevating operation lever 20 as an operation member, and an insertion unit 24 that is provided on the distal end side of the operation unit 22.

Figure 2:
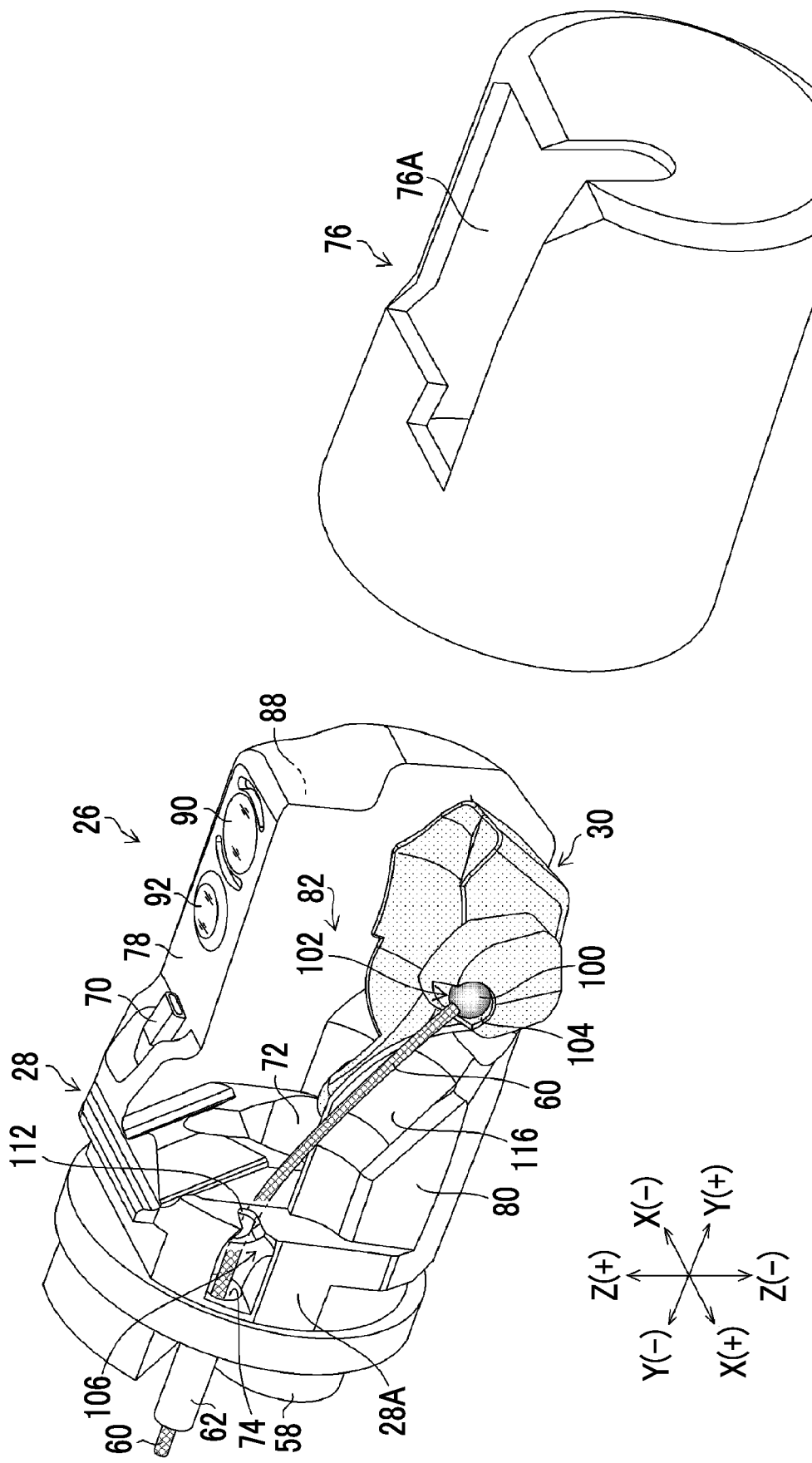
FIG. 2 is a perspective view of a distal end member of which an elevator is positioned at a fallen position.
Figure 3:
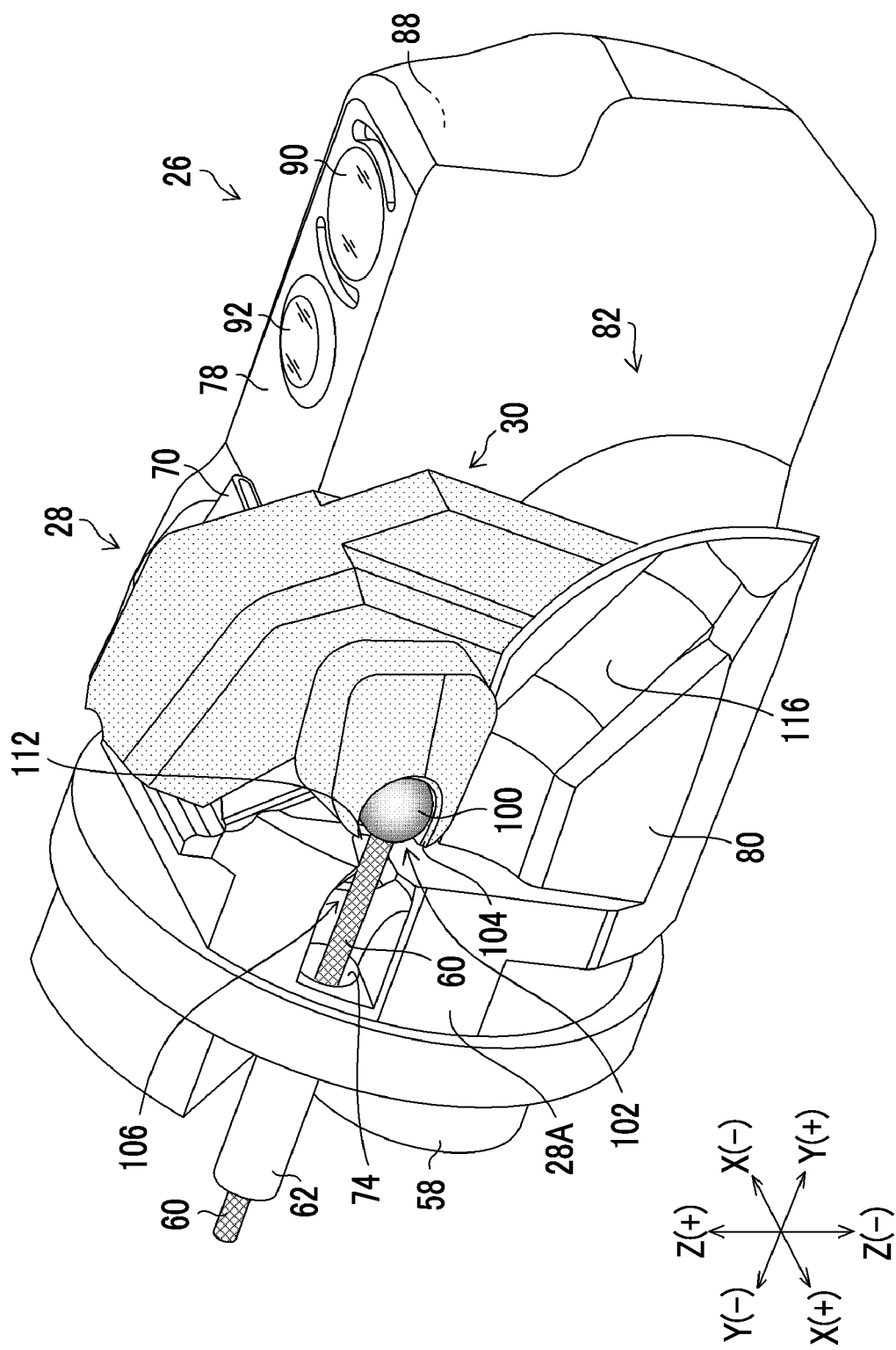
FIG. 3 is a perspective view of the distal end member of which the elevator is positioned at an elevated position.

Further, as shown in perspective views of FIGS. 2 and 3 showing the configuration of a distal end part 26 of the insertion unit 24, the distal end part 26 of the insertion unit 24 is provided with a distal end member 28 and an elevator 30 to be described later is mounted on the distal end member 28. FIG. 2 is a perspective view of the distal end member 28 of which the elevator 30 is positioned at a fallen position, and FIG. 3 is a perspective view of the distal end member 28 of which the elevator 30 is positioned at an elevated position.

In the following description, an upward direction refers to a Z(+) direction in FIGS. 1 and 2 and a downward direction refers to a Z(−) direction in FIGS. 1 and 2. Further, a right direction refers to an X(+) direction in FIG. 2, and a left direction refers to an X(−) direction in FIG. 2. Furthermore, a Y(+) direction in FIGS. 1 and 2 refers to a direction toward a distal end side of the distal end member 28 and a Y(−) direction in FIGS. 1 and 2 refers to a direction toward a proximal end side of the distal end member 28.

Returning to FIG. 1, the operation unit 22 includes an operation unit body 32 that is provided with the elevating operation lever 20, a grip part 34 that is connected to the operation unit body 32, and an extending part 36 that extends from the grip part 34 toward the distal end side. The proximal end portion of the insertion unit 24 is provided on the distal end side of the extending part 36 through a bending-proof pipe 38. The grip part 34 is a part that is to be gripped by an operator during the operation of the endoscope 10.

The extending part 36 is a part corresponding to a non-grip region which extends toward the distal end side from the distal end portion of the grip part 34 and on which a movable member 96 and a rotating body 97 (see FIG. 6) and some components of an elevating operation mechanism 120 (FIGS. 9 and 10) to be described later are provided. Specifically, a region A from a distal end portion 44A of a convex mount portion 44 for a treatment tool inlet 42, which is provided at the grip part 34, up to a proximal end portion 38A of the bending-proof pipe 38 corresponds to the extending part 36. An annular flange 40 is provided in the region of the extending part 36.

The operation unit body 32 of the operation unit 22 is provided with a universal cord 46. A light source connector 50 is provided on the distal end side of the universal cord 46, an electrical connector 48 is provided on the light source connector 50 so as to branch, the electrical connector 48 is connected to the processor device 14, and the light source connector 50 is connected to the light source device 16.

The insertion unit 24 is adapted so that the distal end part 26, a bendable part 52, and a soft part 54 are connected from the distal end side toward the proximal end side.

The following components are provided in the insertion unit 24. That is, components, such as a treatment tool channel 58, an elevating operation wire 60 (hereinafter referred to as a wire 60), an elevating operation wire channel 62 (hereinafter referred to as a wire channel 62), a light guide (not shown), an air/water supply tube (not shown), angle wires (not shown), and a signal cable (not shown), are provided in the insertion unit 24. The treatment tool channel 58 guides a distal end portion 56A of the treatment tool 56 shown in FIG. 1 to the distal end member 28 shown in FIG. 2, the wire 60 is used to perform an operation for changing the lead-out direction of the distal end portion 56A of the treatment tool 56 led out of the distal end member 28, the wire channel 62 guides the distal end portion of the wire 60 to the distal end member 28, and the light guide (not shown) guides illumination light supplied from the light source device 16 shown in FIG. 1 to the distal end member 28 shown in FIG. 2.

Returning to FIG. 1, the operation unit 22 is formed in a substantially cylindrical shape as a whole and has a cylinder axis B extending in a Y(+)-Y(−) direction. A pair of angle knobs 64 and 64 used to perform an operation for bending the bendable part 52 is disposed on one side surface 22A that is positioned on one side of a vertical cross section of the operation unit 22 including the cylinder axis B. The pair of angle knobs 64 and 64 is provided on the same axis so as to be rotationally movable.

The bendable part 52 includes a structure that is formed of a plurality of angle rings (not shown) connected to each other so as to be rotationally movable. The outer periphery of this structure is covered with a tubular mesh body woven with metal wires and the outer peripheral surface of the mesh body is covered with a tubular covering made of rubber, so that the bendable part 52 is formed. For example, four angle wires (not shown) are provided from the bendable part 52 having this configuration to the angle knobs 64 and 64 and these angle wires are pushed or pulled by the rotational moving operation of the angle knobs 64 and 64, so that the bendable part 52 is vertically and laterally bent.

An air/water supply button 66 and a suction button 68 are provided on the operation unit body 32 of the operation unit 22 side by side. In a case where the air/water supply button 66 is operated, air and water can be jetted from an air/water supply nozzle 70 provided on the distal end member 28 shown in FIG. 2. Further, in a case where the suction button 68 shown in FIG. 1 is operated, body fluid, such as blood, can be sucked from a suction port that is provided on the distal end member 28 shown in FIG. 2 and also functions as a treatment tool outlet 72.

Furthermore, the grip part 34 of the operation unit 22 shown in FIG. 1 is provided with a treatment tool inlet 42 into which the treatment tool 56 is to be introduced. The treatment tool 56, which is introduced from the treatment tool inlet 42 so that the distal end portion 56A is a leading end, is inserted into the treatment tool channel 58 of FIG. 2 inserted into the insertion unit 24 and is led out of the treatment tool outlet 72, which is provided in the distal end member 28, to the outside.

Further, the elevating operation lever 20 is rotatably provided on the same axis as the angle knobs 64 and 64 on one side surface 22A of the operation unit 22 shown in FIG. 1. The elevating operation lever 20 is operated to rotate by the hand of an operator gripping the grip part 34. In a case where the elevating operation lever 20 is operated to rotate, the wire 60 shown in FIG. 2 is pushed or pulled by the elevating operation mechanism 120 (see FIGS. 9 and 10) that operates in conjunction with the rotating operation of the elevating operation lever 20. Accordingly, the attitude of the elevator 30, which is connected to the distal end side of the wire 60, is changed between the elevated position shown in FIG. 3 and the fallen position shown in FIG. 2. The above-mentioned elevating operation mechanism 120 will be described later.

The soft part 54 shown in FIG. 1 includes a spiral pipe (not shown) formed of a thin belt-like metal plate that has elasticity and is spirally wound. The outside of the spiral pipe is covered with a tubular mesh body woven with metal wires and the outer peripheral surface of the mesh body is covered with a tubular covering consisting of a resin, so that the soft part 54 is formed.

The endoscope 10 according to the embodiment having the above-mentioned configuration is a side-viewing endoscope used as a duodenoscope, and the insertion unit 24 is inserted into an object to be examined through an oral cavity. The insertion unit 24 is inserted into the duodenum from the gullet through the stomach, so that treatment, such as predetermined examination or predetermined therapy, is performed.

A pair of biopsy forceps, which includes a cup provided at the distal end portion 56A thereof and capable of being used to collect body tissue, has been exemplified as the treatment tool 56 in the embodiment, but the treatment tool 56 is not limited thereto. For example, a treatment tool, such as a contrast tube or a knife for endoscopic sphincterotomy (EST), is used as another treatment tool.

Next, the distal end part 26 of the insertion unit 24 will be described.

As shown in FIG. 2, the distal end part 26 of the insertion unit 24 includes the distal end member 28 and a cap 76 that is attachably and detachably mounted on the distal end member 28. The cap 76 is formed substantially in the shape of a tube of which the distal end side is sealed, and a substantially rectangular open window 76A is formed at a part of the outer peripheral surface of the cap 76. In a case where the cap 76 is mounted on the distal end member 28, the open window 76A of the cap 76 communicates with the treatment tool outlet 72 of the distal end member 28. Accordingly, the distal end portion 56A of the treatment tool 56 led out of the treatment tool outlet 72 is led out of the open window 76A to the outside.

The cap 76 is made of an elastic material, for example, a rubber material, such as fluororubber or silicone rubber, or a resin material, such as polysulfone or polycarbonate, and an engaging portion (not shown) to be engaged with a groove (not shown) formed on the distal end member 28 is provided on the proximal end side of the cap 76. The engaging portion is engaged with the groove of the distal end member 28, so that the cap 76 is mounted on the distal end member 28. Furthermore, after treatment using the endoscope 10 ends, the cap 76 is detached from the distal end member 28 and is washed and disinfected or is discarded as a disposable.

The distal end member 28 is made of a metal material having corrosion resistance. Further, a partition wall 78 protruding toward the distal end side and a partition wall 80 facing the partition wall 78 are provided integrally with the distal end member 28. An elevator-housing chamber 82 housing the elevator 30 is formed between the partition walls 78 and 80. The treatment tool outlet 72 out of which the treatment tool 56 is led to the outside is formed on the proximal end side of the elevator-housing chamber 82, and the distal end portion of the treatment tool channel 58 is connected to the treatment tool outlet 72.

The treatment tool channel 58 is inserted into the insertion unit 24 shown in FIG. 1. The proximal end portion of the treatment tool channel 58 is connected to a distal end pipe 202 of a branch pipe 200 (see FIG. 10) provided in the operation unit 22.

The branch pipe 200 has a well-known structure. The proximal end portion of the branch pipe 200 branches into two pipe lines 204 and 206, and the treatment tool inlet 42 is formed at the proximal end of one pipe line 204. Accordingly, the distal end portion 56A of the treatment tool 56 introduced into the treatment tool channel 58 from the treatment tool inlet 42 through the pipe line 204 is inserted into the treatment tool channel 58 and is led out of the treatment tool outlet 72 shown in FIG. 2 to the elevator-housing chamber 82. Then, the lead-out direction of the distal end portion 56A of the treatment tool 56 led to the elevator-housing chamber 82 is changed according to the attitude of the elevator 30, which is disposed in the elevator-housing chamber 82, between the elevated position and the fallen position. Further, the distal end of a suction pipe 208 sucking body fluid, such as blood, is connected to the proximal end of the other pipe line 206 of the branch pipe 200 shown in FIG. 10.

Figure 4:
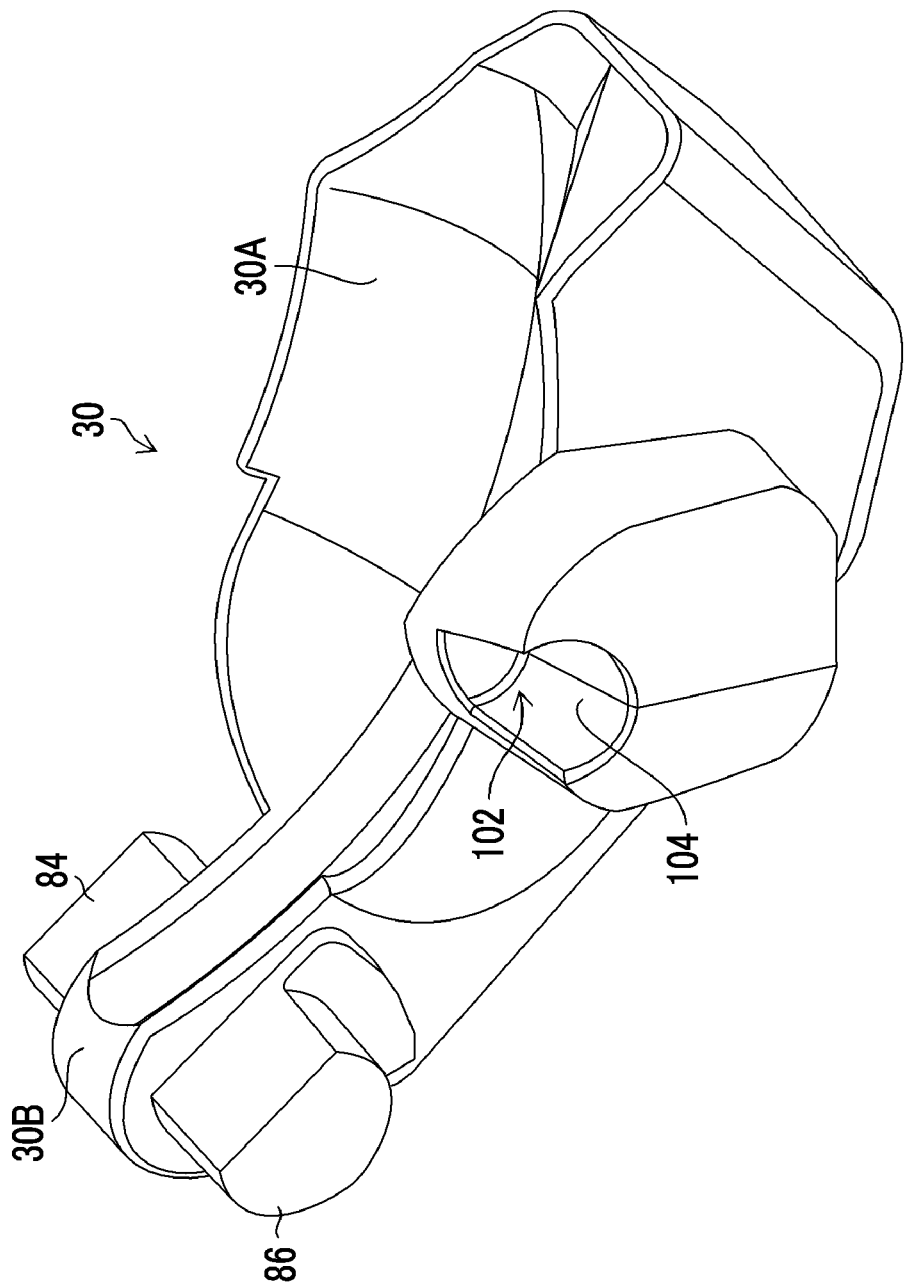
FIG. 4 is an enlarged perspective view of the elevator.

FIG. 4 is an enlarged perspective view of the elevator 30. As shown in FIG. 4, a guide surface 30A is provided on the upper surface of the elevator 30. The distal end portion 56A of the treatment tool 56 shown in FIG. 1 is led out of the open window 76A of the cap 76 shown in FIG. 2 to the outside along the guide surface 30A.

As shown in FIG. 4, rotational movement shafts 84 and 86 are provided on both side surfaces of a base portion 30B of the elevator 30. The axial direction of the rotational movement shafts 84 and 86 is set to an X(+)-X(−) direction shown in FIG. 2 in a case where the elevator 30 is mounted on the distal end member 28.

Figure 5:
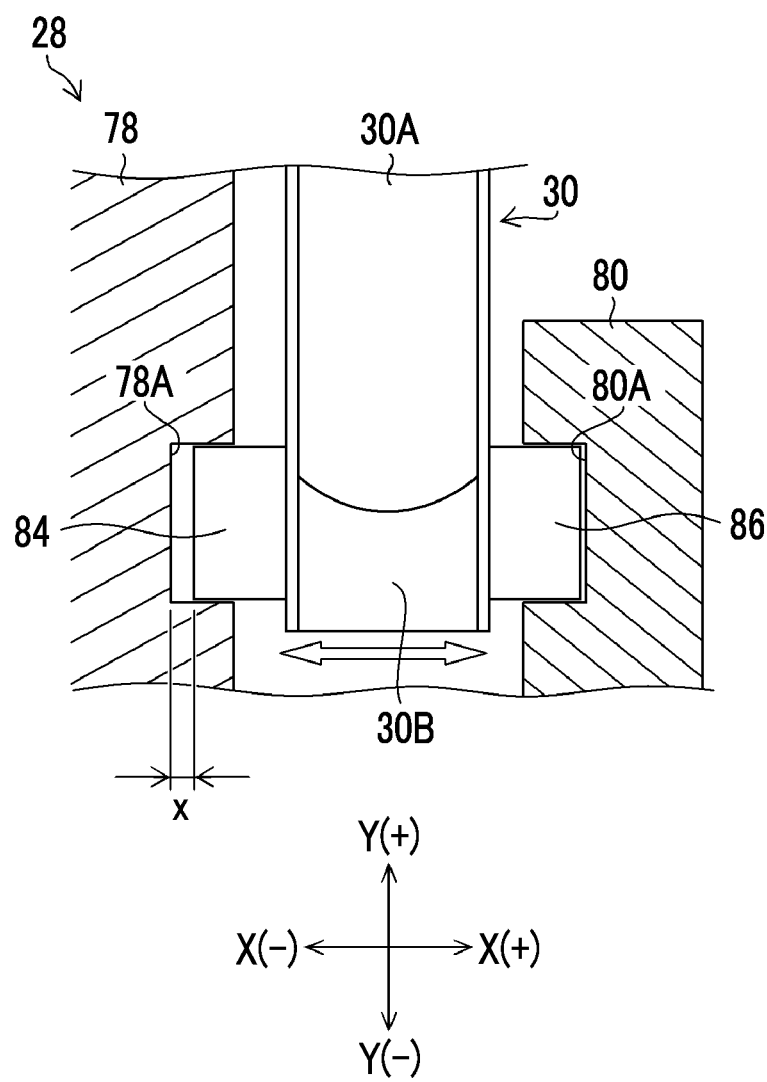
FIG. 5 is a cross-sectional view of main portions showing a structure for mounting the elevator on the distal end member.

FIG. 5 is a cross-sectional view of main portions showing a structure for mounting the elevator 30 on the distal end member 28. As shown in FIG. 5, the axes of the rotational movement shafts 84 and 86 are disposed on the same axis through the base portion 30B of the elevator 30, the rotational movement shaft 84 is fitted to a recessed bearing portion 78A of the partition wall 78 so as to be rotationally movable, and the rotational movement shaft 86 is fitted to a recessed bearing portion 80A of the partition wall 80 so as to be rotationally movable. Furthermore, the rotational movement shafts 84 and 86 are mounted in the bearing portions 78A and 80A while having a predetermined clearance x in the axial direction of the rotational movement shafts 84 and 86. In a case where the rotational movement shafts 84 and 86 are biased to one side using the clearance x, a part of one of the bearing portions 78A and 80A is exposed to the outside and a brush can be easily inserted into the exposed portion. Accordingly, the washability of the bearing portions 78A and 80A is improved.

As shown in FIGS. 2 and 3, an optical system-housing chamber 88 is provided in the partition wall 78. An illumination window 90 and an observation window 92 are provided at the upper portion of the optical system-housing chamber 88 so as to be adjacent to each other, and the air/water supply nozzle 70 directed to the observation window 92 is provided on the distal end member 28. The air/water supply nozzle 70 is connected to an air/water supply device (not shown) through an air/water supply tube (not shown) inserted into the insertion unit 24, and air or water is jetted toward the observation window 92 from the air/water supply nozzle 70 in a case where the air/water supply button 66 of the operation unit 22 shown in FIG. 1 is operated. Accordingly, the observation window 92 is washed.

Further, an illumination unit (not shown) and an image pickup unit (not shown) are housed in the optical system-housing chamber 88. The illumination unit comprises an illumination lens (not shown) that is installed in the illumination window 90, and a light guide (not shown) that is disposed so that the distal end surface of the light guide faces the illumination lens. The light guide is disposed in the universal cord 46 from the insertion unit 24 of the endoscope 10 through the operation unit 22, and the proximal end of the light guide is connected to the light source device 16 through the light source connector 50. Accordingly, illumination light generated from the light source device 16 is transmitted through the light guide and is applied to the outside from the illumination window 90.

The above-mentioned image pickup unit comprises an image pickup optical system (not shown) that is provided in the observation window 92 and a complementary metal oxide semiconductor (CMOS) or charge coupled device (CCD) image pickup element (not shown). The image pickup element is connected to the processor device 14 through a signal cable (not shown) inserted into the insertion unit 24 shown in FIG. 1. After image pickup signals of a subject image obtained by the image pickup unit are output to the processor device 14 through the signal cable and are subjected to image processing, the image pickup signals are displayed on the display 18 as a subject image.

Figure 6:
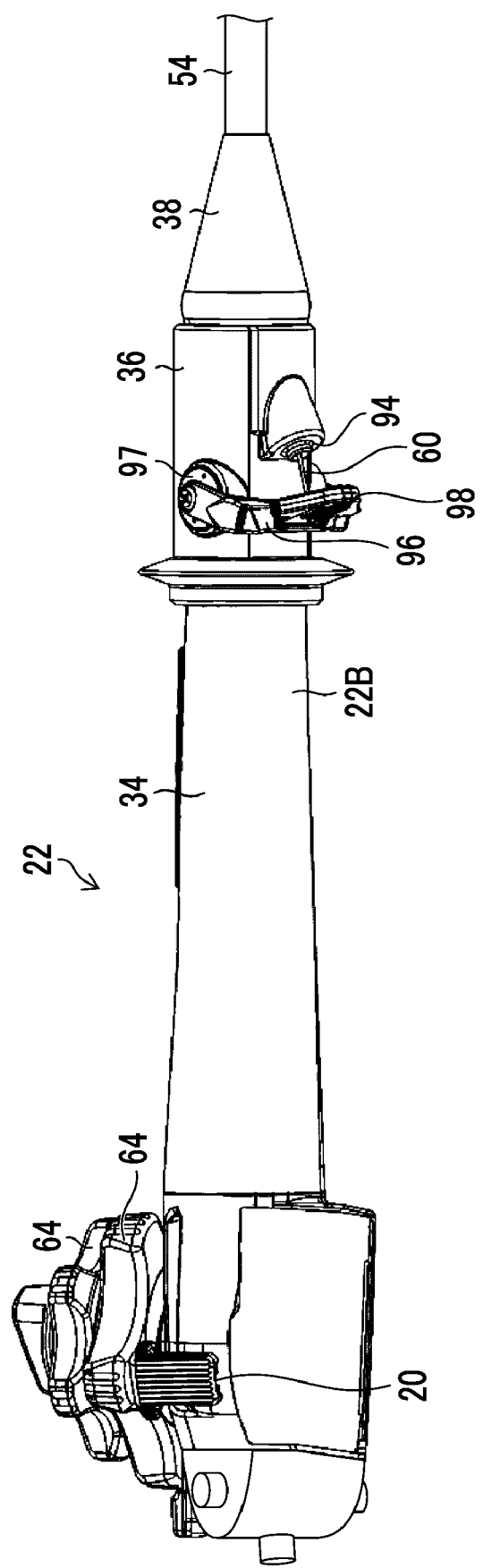
FIG. 6 is a perspective view showing the other side surface facing one side surface of an operation unit shown in FIG. 1.

Although the above description is repeated, the wire 60 will be described first. As shown in FIGS. 2 and 3, the distal end side of the wire 60 is disposed outside an outlet 74 and is connected to the elevator 30. Further, the proximal end side of the wire 60 is disposed outside an inlet 94 provided on the operation unit 22 as shown in FIG. 6, and is connected to the movable member 96 (see FIG. 10). The outlet 74 is an example of a distal end opening of the embodiment of the invention, and the inlet 94 is an example of a proximal end opening of the embodiment of the invention.

FIG. 6 is a perspective view of the operation unit 22, and is a perspective view showing the other side surface 22B facing one side surface 22A of the operation unit 22 shown in FIG. 1.

According to FIG. 6, the extending part 36 of the operation unit 22 is provided with the inlet 94. A mounting member 98 is provided at the proximal end of the wire 60 disposed outside the inlet 94, and is attachably and detachably mounted in an engaging hole (to be described later) of the movable member 96.

The operation unit 22 is provided with the movable member 96 and the rotating body 97. The rotating body 97 is disposed to be exposed to the outside of the operation unit 22, and operates in conjunction with the operation of the elevating operation lever 20 by the elevating operation mechanism 120 to be described later. The rotating body 97 may be disposed so that at least a part of the rotating body 97 is exposed to the outside. The movable member 96 is attachably and detachably connected to the rotating body 97. The movable member 96 is disposed to be exposed to the outside of the operation unit 22. Further, the movable member 96 is rotatably disposed on the other side surface 22B facing one side surface 22A on which the angle knobs 64 and 64 are provided in the embodiment, but the position of the movable member 96 disposed on the operation unit 22 is not limited. The movable member 96 may be disposed at a predetermined position on the operation unit 22 so as to be capable of being rotated by the rotating body 97. Furthermore, the movable member 96 is a driven lever with respect to the rotating body 97 that is rotated in conjunction with the rotating operation of the elevating operation lever 20.

The elevating operation mechanism 120 is disposed in the operation unit 22 and causes the movable member 96 to operate through the rotating body 97 in conjunction with the operation of the elevating operation lever 20. Accordingly, in a case where the elevating operation lever 20 is operated, the movable member 96 is operated through the elevating operation mechanism 120 and the rotating body 97 and the wire 60 (see FIG. 2) connected to the movable member 96 is pushed or pulled. The elevating operation mechanism 120 will be described later.

Next, an engaging structure for detachably engaging the distal end of the wire 60 with the elevator 30 will be described.

Returning to FIGS. 2 and 3, an engaging member 100 is provided at the distal end of the wire 60. Further, the elevator 30 is provided with a housing groove 102 that is detachably engaged with the engaging member 100 and includes an opening 104 formed on the side thereof corresponding to the X(+) direction. Accordingly, the engaging member 100 provided at the distal end of the wire 60 is housed in the housing groove 102 through the opening 104, so that the distal end of the wire 60 is connected to the elevator 30.

In the embodiment, the engaging member 100 is a sphere and the housing groove 102 is a spherical concave portion housing the engaging member 100 formed of a sphere. The shapes of the engaging member 100 and the housing groove 102 are not limited to the above-mentioned shapes. However, in a case where the engaging member 100 is formed of a sphere and the housing groove 102 is formed of a spherical concave portion, sliding resistance between the engaging member 100 and the housing groove 102 generated due to an operation for pushing or pulling the wire 60 can be reduced. Accordingly, an operation for pushing or pulling the wire 60 can be smoothly performed.

Further, the distal end member 28 is provided with a guide portion 106 for engagement that is connected to the housing groove 102 at the elevated position shown in FIG. 3. The guide portion 106 for engagement has a function to guide the engaging member 100, which is led out of the outlet 74, to the opening 104 of the housing groove 102. The outlet 74 is provided at the distal end member 28, and communicates with the inlet 94 (see FIG. 6) through the wire channel 62 that is provided in the insertion unit 24.

According to the endoscope 10 including the guide portion 106 for engagement, in a case where the wire 60 is introduced from the inlet 94 so that the engaging member 100 is a leading end, the engaging member 100 is inserted into the wire channel 62 (see FIG. 2) and is led out of the outlet 74 to the outside. Then, due to a continuous operation for introducing the wire 60, the engaging member 100 is guided toward the opening 104 of the housing groove 102 of the elevator 30 by the guide portion 106 for engagement and is engaged with the housing groove 102 through the opening 104. Therefore, according to the endoscope 10 of the embodiment, the engaging member 100 of the wire 60 can be engaged with the housing groove 102 of the elevator 30 by only an operation for introducing the wire 60.

Figure 7:
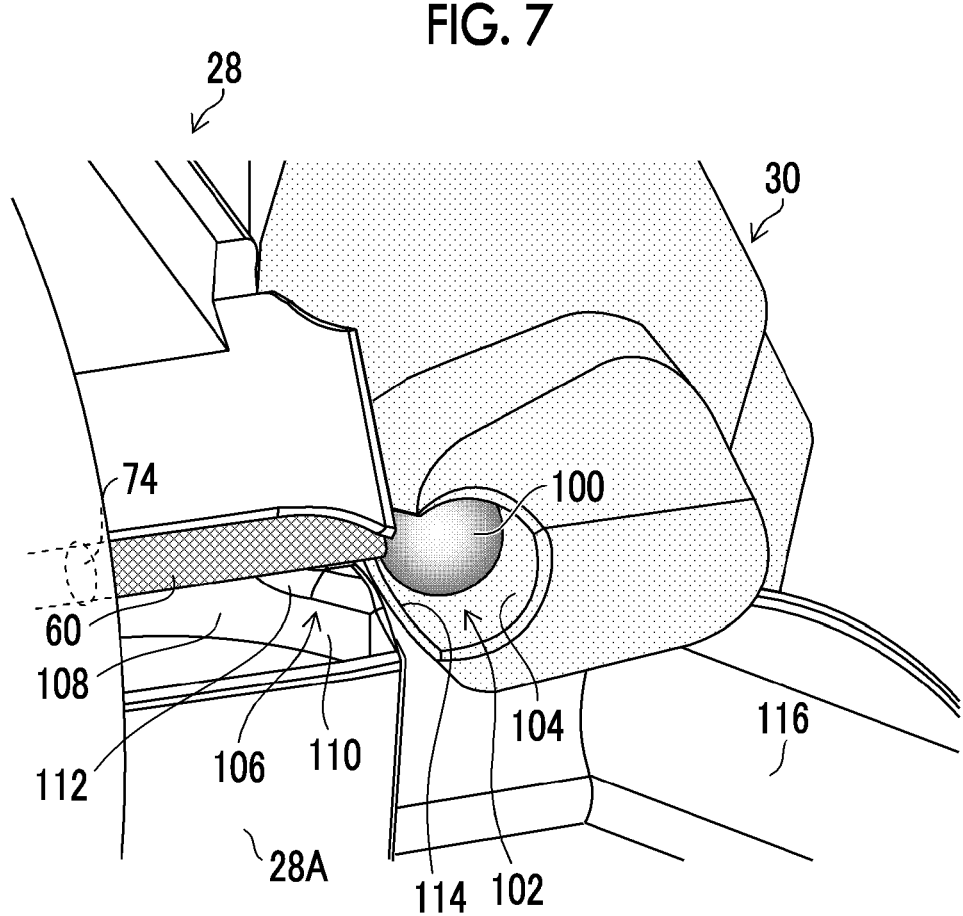
FIG. 7 is an enlarged perspective view showing that an engaging portion is housed in a housing portion through a guide portion for engagement.
Figure 8:
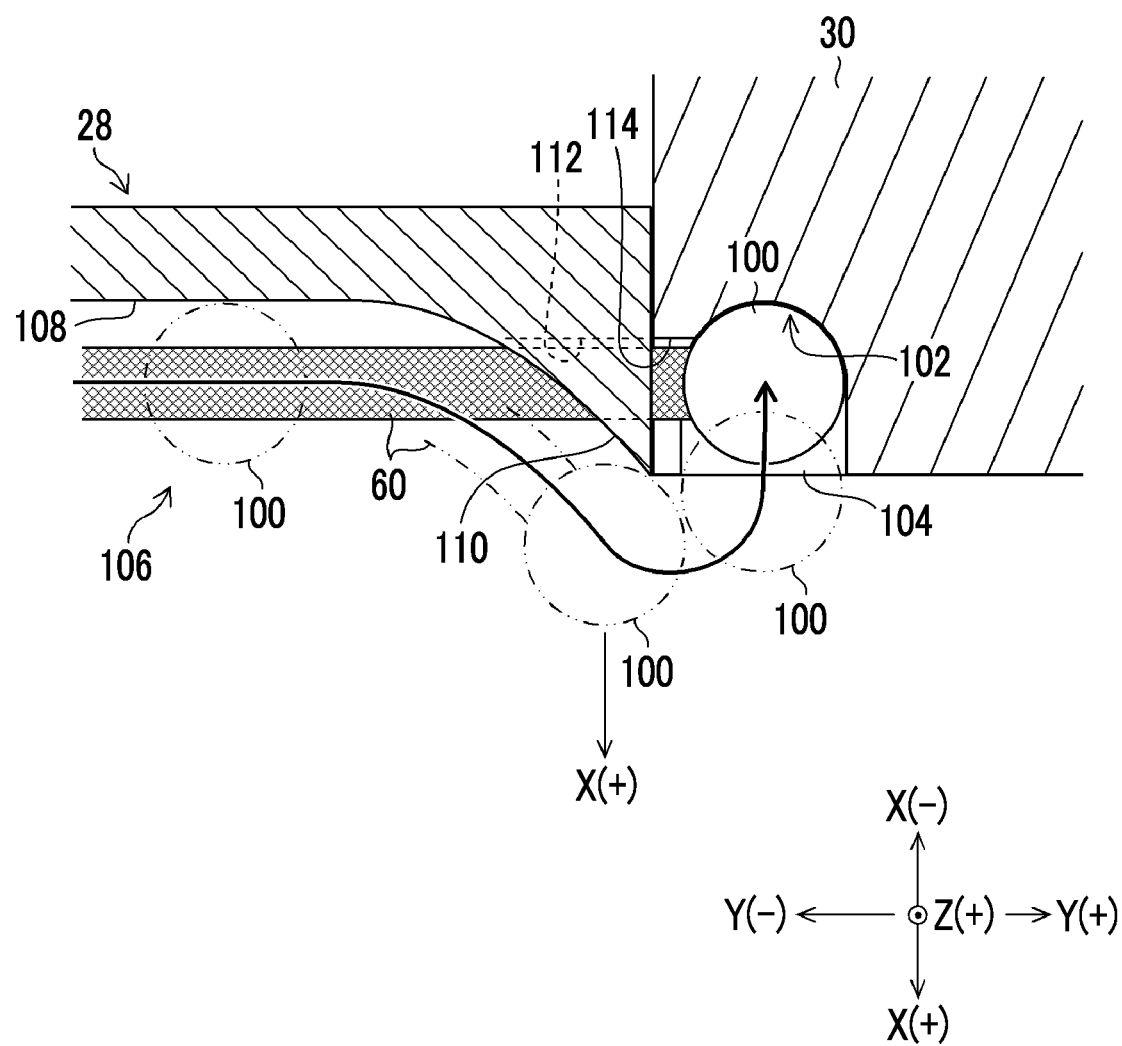
FIG. 8 is a diagram illustrating an operation where the engaging portion is guided by the guide portion for engagement and is housed in the housing portion.

FIG. 7 is an enlarged perspective view showing that the engaging member 100 is engaged with the housing groove 102 through the guide portion 106 for engagement. FIG. 8 is a diagram illustrating an operation until the engaging member 100 is guided by the guide portion 106 for engagement and is engaged with the housing groove 102 with time.

As shown in FIGS. 7 and 8, the guide portion 106 for engagement comprises a guide passage 108 for engagement that guides the engaging member 100, which is led out of the outlet 74, to the opening 104 of the housing groove 102, and a deformation generating portion 110 that is connected to the opening 104 of the housing groove 102 in the guide passage 108 for engagement. The deformation generating portion 110 is in contact with the engaging member 100, which is moved toward the opening 104 in the guide passage 108 for engagement in the Y(+) direction, and guides the engaging member 100 in the X(+) direction while guiding the engaging member 100 in the Y(+) direction.

Accordingly, as the engaging member 100 approaches the opening 104 along the guide passage 108 for engagement, the distal end side of the wire 60 is elastically deformed in a direction (X(+) direction) where the distal end side of the wire 60 gradually goes away from the opening 104. In a case where the engaging member 100 being moved in the guide passage 108 for engagement has passed through the deformation generating portion 110, the engaging member 100 is moved in the X(−) direction by the restoring force of the wire 60 and is engaged with the housing groove 102 through the opening 104.

The guide passage 108 for engagement is formed by cutting out a part of a peripheral surface 28A of the distal end member 28 in a concave shape, and is a surface that is gradually inclined toward a side corresponding to the X(+) direction from the outlet 74 in the Y(+) direction. The deformation generating portion 110 is formed on the distal end side of the guide passage 108 for engagement.

Further, a groove 112, which allows the distal end side of the wire 60 to be fitted and released in a case where the engaging member 100 is engaged with the housing groove 102, is formed in the guide portion 106 for engagement. Furthermore, a groove 114, which allows the distal end side of the wire 60 to be fitted and released in a case where the engaging member 100 is engaged with the housing groove 102, is also formed on the proximal end side of the housing groove 102 of the elevator 30. The width of the groove 112 in a direction perpendicular to the plane of FIG. 8 is larger than the diameter of the wire 60, and is smaller than the diameter of the engaging member 100 so that the engaging member 100 passing through the deformation generating portion 110 is not fitted into the groove 112. Further, the width of the groove 114 in the direction perpendicular to the plane of FIG. 8 is larger than the diameter of the wire 60, and is smaller than the diameter of the engaging member 100 so that the engaging member 100 engaged with the housing groove 102 is not separated in the Y(−) direction.

The guide portion 106 for engagement has a form suitable for engaging the engaging member 100 with the housing groove 102 in a state where the elevator 30 is positioned at the elevated position. That is, as shown in FIG. 7, the housing groove 102 is disposed at a position facing the outlet 74 in a state where the elevator 30 is positioned at the elevated position. Accordingly, in a case where the engaging member 100 is moved straight from the outlet 74, the engaging member 100 can be engaged with the housing groove 102 of the elevator 30, which is positioned at the elevated position, through the guide portion 106 for engagement.

Next, a disengaging structure for disengaging the engaging member 100 of the wire 60, which is engaged with the housing groove 102 of the elevator 30, from the housing groove 102 will be described.

The distal end member 28 is provided with a guide surface 116 for disengagement, and the guide surface 116 for disengagement is provided on the upper surface of the partition wall 80 (see FIG. 2). The guide surface 116 for disengagement is a guide surface (see FIGS. 2 and 3) that is inclined toward a side corresponding to the Z(−) direction in the X(+) direction. Further, the guide surface 116 for disengagement functions as a surface for guiding the wire 60 in a direction where the engaging member 100 is disengaged from the inside of the housing groove 102 to the outside of the opening 104 in a case where the wire 60 is operated to be further pushed in a state where the engaging member 100 is engaged with the housing groove 102 and the elevator 30 is positioned at the fallen position.

According to the disengaging structure having this configuration, a mounting member (to be described later) provided at the proximal end of the wire 60 is detached from the engaging hole (to be described later) of the movable member 96 and the wire 60 is then operated to be pushed from the inlet 94 of the extending part 36 so that the elevator 30 is positioned to the fallen position shown in FIG. 2 from the elevated position shown in FIG. 3. After that, in a case where the wire 60 is operated to be further pushed, the wire 60 is guided by the guide surface 116 for disengagement of the distal end member 28 in the X(+) direction where the engaging member 100 is disengaged from the inside of the housing groove 102 to the outside of the opening 104. Accordingly, the engaging member 100 is easily disengaged from the inside of the housing groove 102 to the outside of the opening 104 by the restoring force of the wire 60.

Next, the elevating operation mechanism 120 will be described.

Figure 9:
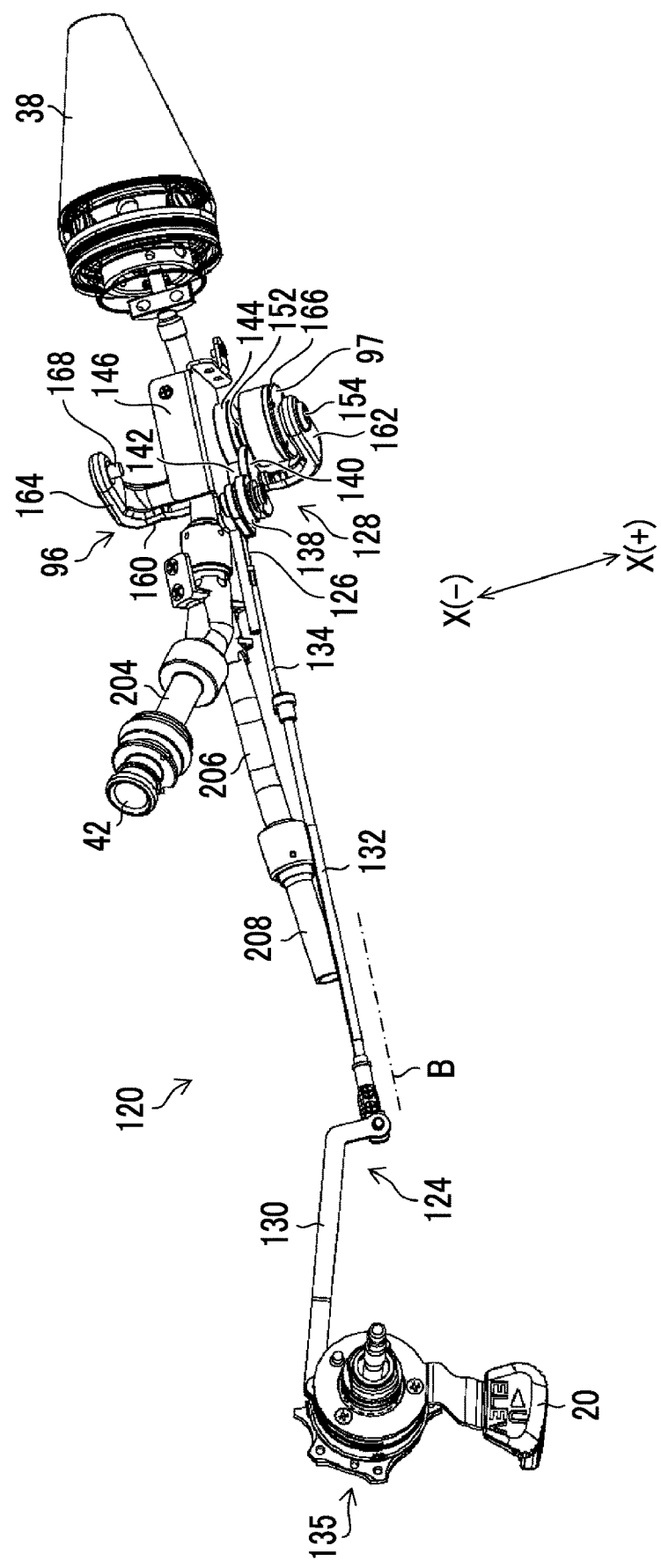
FIG. 9 is a diagram showing the entire configuration of an elevating operation mechanism.
Figure 10:
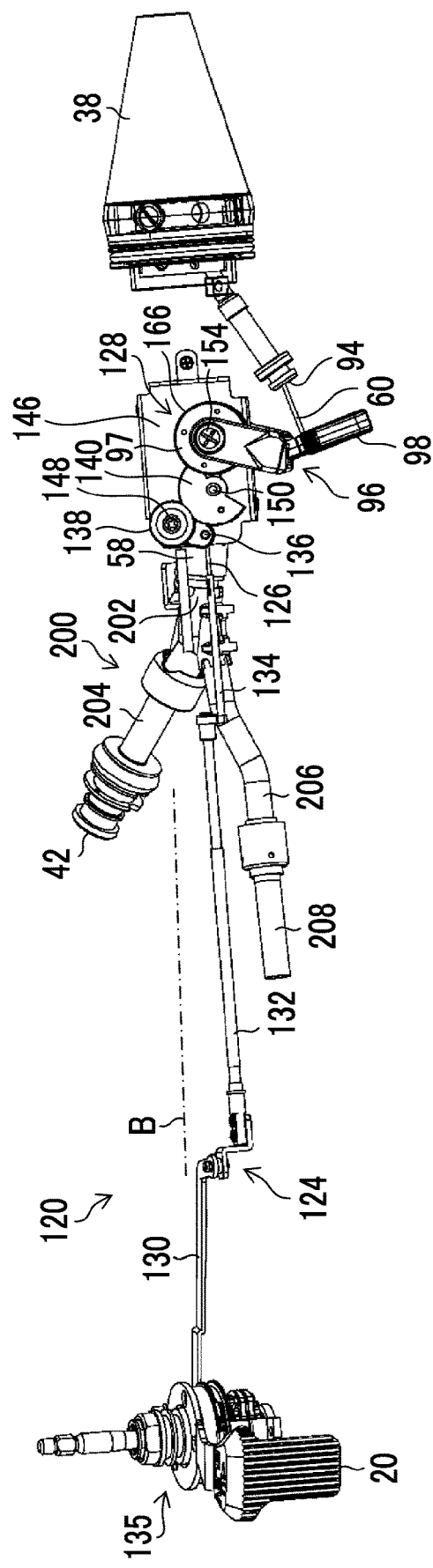
FIG. 10 is a side view of the elevating operation mechanism shown in FIG. 9.

FIG. 9 is a diagram showing the entire configuration of the elevating operation mechanism 120. Further, FIG. 10 is a side view of the elevating operation mechanism 120 shown in FIG. 9. In FIGS. 9 and 10, an exterior case (not shown) of the operation unit 22 is omitted and the inside of the operation unit 22 is shown.

As shown in FIGS. 9 and 10, the elevating operation mechanism 120 is provided in the operation unit 22. Specifically, the components of the respective part of the elevating operation mechanism 120 are provided in the operation unit 22 from the operation unit body 32 to the extending part 36.

Further, the elevating operation mechanism 120 is a power transmission mechanism that connects the elevating operation lever 20 to the movable member 96 and transmits the rotating operation of the elevating operation lever 20 to the movable member 96. In the embodiment, the elevating operation lever 20 and the movable member 96 are connected to each other through the rotating body 97.

The elevating operation mechanism 120 comprises a first conversion mechanism 124 that converts the rotary motion of the elevating operation lever 20 into linear motion, a wire 126 that is linearly moved by the first conversion mechanism 124, and a second conversion mechanism 128 that converts the linear motion of the wire 126 into rotary motion to rotate the rotating body 97 and the movable member 96 connected to the rotating body 97. The wire 126 is an example of a drive member of the embodiment of the invention.

The first conversion mechanism 124 comprises a crank member 130 of which the proximal end is connected to the elevating operation lever 20, a first slider 132 of which the proximal end is connected to the distal end of the crank member 130, and a second slider 134 of which the proximal end is connected to the distal end of the first slider 132. The elevating operation lever 20 and the crank member 130 are connected to each other by a connection mechanism 135.

The proximal end of the wire 126 is connected to the distal end of the second slider 134, and the distal end of the wire 126 is connected to the second conversion mechanism 128 including a speed reducer.

According to the first conversion mechanism 124 having the above-mentioned configuration, in a case where the elevating operation lever 20 is operated to rotate, the crank member 130, the first slider 132, and the second slider 134 are linearly moved along the cylinder axis B in conjunction with the rotating operation of the elevating operation lever 20. Accordingly, the wire 126 is linearly moved along the cylinder axis B, and the linear motion of the wire 126 is transmitted to the second conversion mechanism 128.

The second conversion mechanism 128 comprises a lever 136, a first gear 138, a second gear 140, a third gear 142, and a fourth gear 144. The first gear 138, the second gear 140, the third gear 142, and the fourth gear 144 form the speed reducer.

The lever 136 is rotatably supported on a bracket 146 through a shaft 148, and the distal end of the wire 126 is connected to the lever 136. Accordingly, the lever 136 is rotated about the shaft 148 by the linear motion of the wire 126.

The first gear 138 is provided integrally with the lever 136 and is rotated about the shaft 148. The second gear 140 meshes with the first gear 138, and is rotatably supported on the bracket 146 through a shaft 150. The third gear 142 is provided integrally with the second gear 140 and is provided on the same axis as the second gear 140. The fourth gear 144 is provided on the same axis as a drive shaft 152 of the rotating body 97, and is rotatably supported on the bracket 146 through the drive shaft 152 together with the rotating body 97. The third gear 142 meshes with the fourth gear 144.

Therefore, according to the second conversion mechanism 128 having the above-mentioned configuration, in a case where the linear motion of the wire 126 is transmitted to the lever 136, the first gear 138 is operated to rotate together with the lever 136 and the rotating operation of the first gear 138 is transmitted to the fourth gear 144 through the second and third gears 140 and 142. As a result, the fourth gear 144 is rotated. Accordingly, the fourth gear 144, the rotating body 97, and the movable member 96 connected to the rotating body 97 are rotated about the drive shaft 152.

Therefore, according to the elevating operation mechanism 120 having the above-mentioned configuration, the rotating operation of the elevating operation lever 20 can be transmitted to the rotating body 97 through the first conversion mechanism 124, the wire 126, and the second conversion mechanism 128. Accordingly, the rotating body 97 is rotated, so that the movable member 96 is rotated about the drive shaft 152.

Further, according to the elevating operation mechanism 120, the rotating operation of the elevating operation lever 20 is decelerated and transmitted to the movable member 96 by the second conversion mechanism 128 including the speed reducer. That is, the rotation angles of leg portions 162 and 164 of the movable member 96 are smaller than the rotation angle of the lever 136 that is operated by the operation of the elevating operation lever 20. Accordingly, since a force required to operate the elevating operation lever 20 can be further reduced, it is easy to control the elevated/fallen attitude of the elevator 30 by the elevating operation lever 20.

Furthermore, in the embodiment, the wire 126 is exemplified as an example of the drive member of the elevating operation mechanism 120 as shown in FIGS. 9 and 10. Since the wire 126 is used as the drive member, there are the following advantages. That is, since the curved movement (slack) of the wire 126 can occur in a case where the linear motion of the second slider 134 is converted into the rotary motion of the lever 136, a link mechanism does not need to be installed. As a result, the limitations of space are reduced. Further, in a case where the second slider 134 and the lever 136 are connected to each other by a link mechanism, a place to which a force is released is reduced in the elevating operation mechanism 120. However, since the wire 126 is used, a force can be released by the slack of the wire 126. Accordingly, a load applied to the elevating operation mechanism 120 can be reduced. For this reason, even in a case where any force is applied to the movable member 96, which is exposed to the outside of the operation unit 22, from the outside, the wire 126 is loosened, so that the force can be released. Accordingly, a load applied to the elevating operation mechanism 120 can be reduced.

Figure 15:
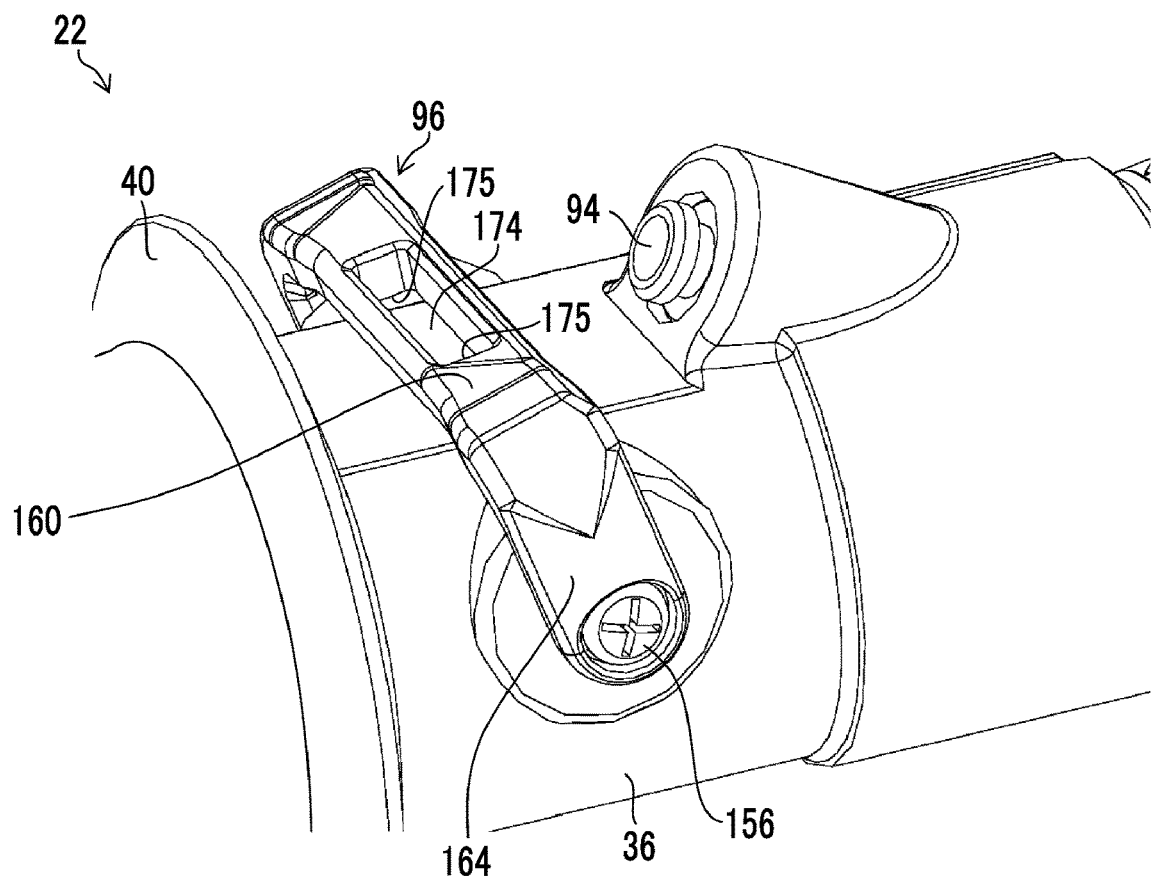
FIG. 15 is a perspective view of an extending part showing an inlet and a movable member.
Figure 16:
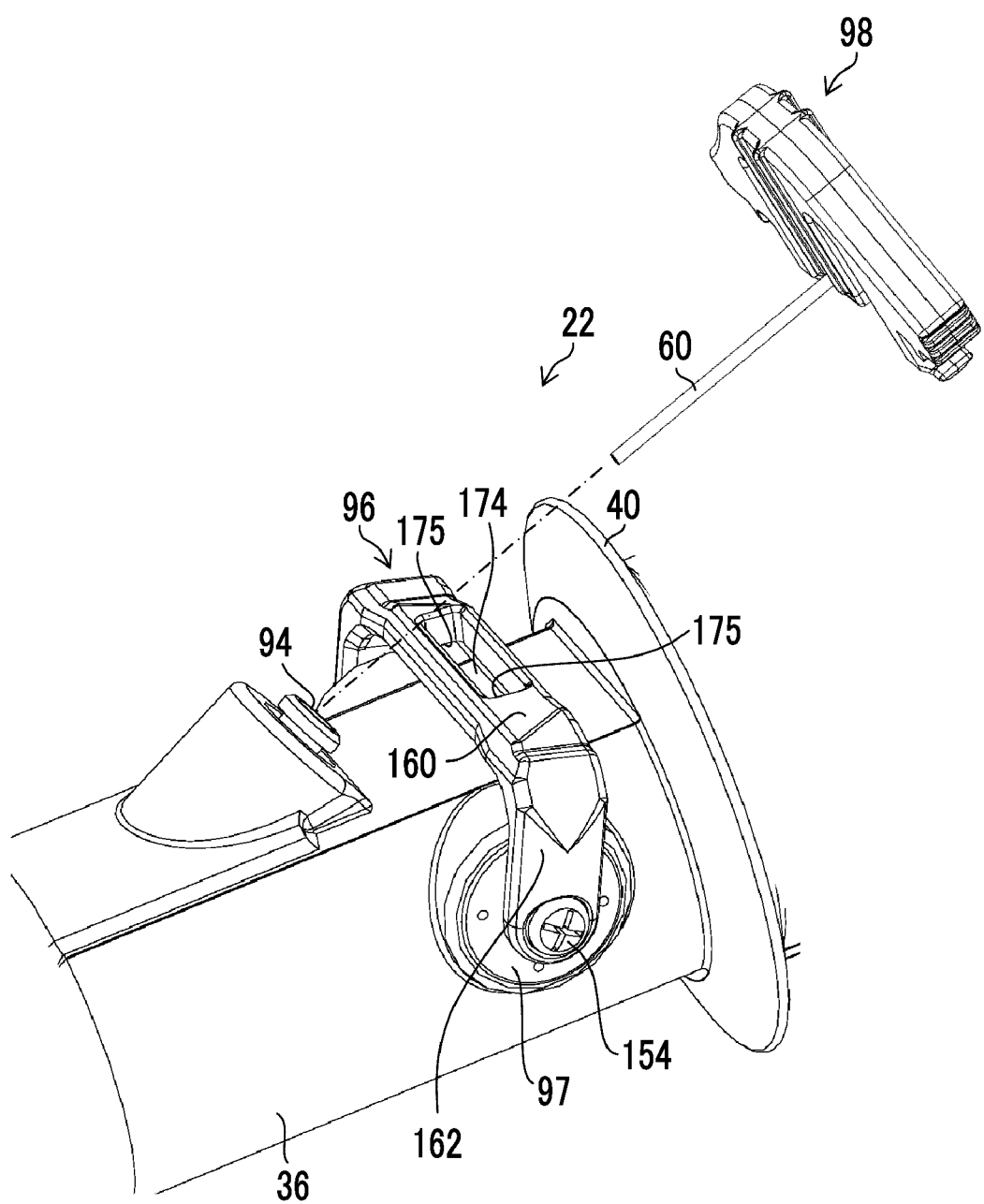
FIG. 16 is a diagram illustrating that a wire is inserted through the inlet so that the engaging member is a leading end.

Here, the shape of the movable member 96 will be described. As shown in FIGS. 15 and 16 to be described later, the movable member 96 comprises a flat plate-shaped beam portion 160 and leg portions 162 and 164 provided at both ends of the beam portion 160 and is formed in a U-shape as a whole. Further, as shown in FIGS. 9 and 10, the rotating body 97 is connected to the drive shaft 152 provided on the side corresponding to the leg portion 162. An O-ring 166 is provided on a part of the outer periphery of the rotating body 97. The rotating body 97 is supported to be rotationally movable on an exterior case (not shown) of the operation unit 22 through the O-ring 166, and a driven shaft 168 provided at the leg portion 164 is supported to be rotationally movable on the exterior case (not shown) through an O-ring (not shown). The watertightness of the operation unit 22 is kept by these O-rings 166. As shown in FIGS. 9 and 10, the leg portion 162 of the movable member 96 is connected to the rotating body 97 by a fixing screw 154. As long as the rotating body 97 can be rotated on the drive shaft 152, the structure of the rotating body 97 is not limited. To allow the rotating body 97 to be smoothly rotated and to seal the extending part 36 by the O-ring provided on the outer periphery of the rotating body 97, it is preferable that the rotating body 97 has a discoid shape or a cylindrical shape.

Further, the rotation axes of the drive shaft 152 and the driven shaft 168 of the movable member 96 are set to a direction (X(+)-X(−) direction) perpendicular to the axial direction of the wire 60. That is, since the movable member 96 is provided to be rotatable about a direction, which is perpendicular to the axial direction of the wire 60, as a rotation axis, the movable member 96 can smoothly push or pull the wire 60.

Next, a connection structure 170 of a first aspect for connecting the proximal end of the wire 60 to the movable member 96 will be described with reference to FIGS. 11 to 15. Since a connection tool as an elevating operation mechanism is not housed in the narrow inner space of the operation unit unlike in the endoscope disclosed in JP1994-315458A (JP-H06-315458A) in the connection structure of the embodiment, it is easy to perform operations for attaching and detaching the wire. Further, since the connection tool as the elevating operation mechanism is not housed in the operation unit unlike in the endoscope disclosed in JP1994-315458A (JP-H06-315458A), it is possible to avoid a problem that the size of the operation unit is increased. Furthermore, since the cable cord is not led to the outside of the control handle and the distal end of the cable cord is not attachably and detachably mounted on the collet and the nut unlike in the endoscope disclosed in EP1759626B, it is easy to perform operations for attaching and detaching the wire. The easiness of the operation for attaching and detaching the proximal end of the wire to and from the elevating operation mechanism will be described with reference to the connection structure 170.

Figure 11:
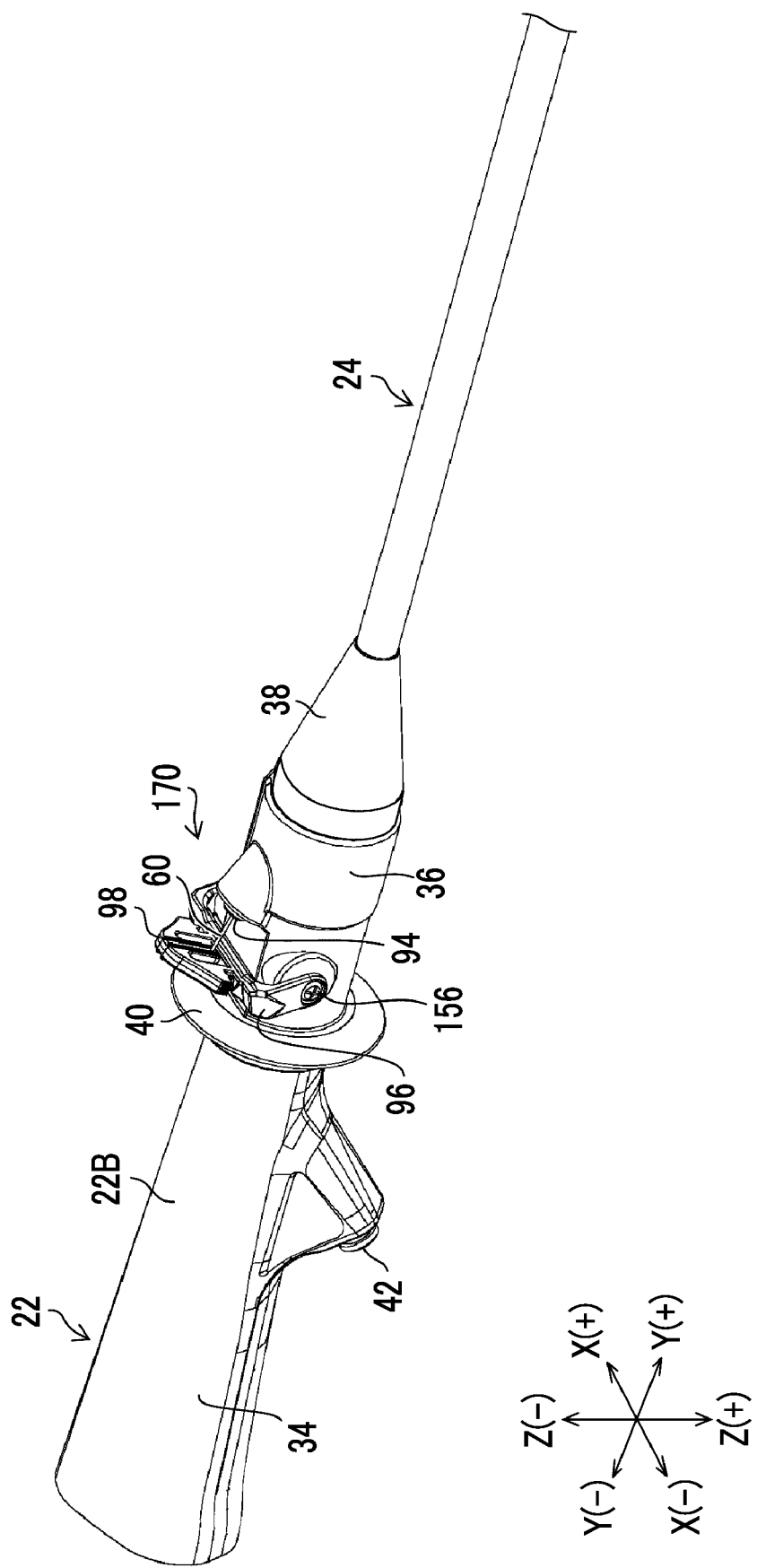
FIG. 11 is a perspective view of a connection structure of a first aspect.
Figure 12:
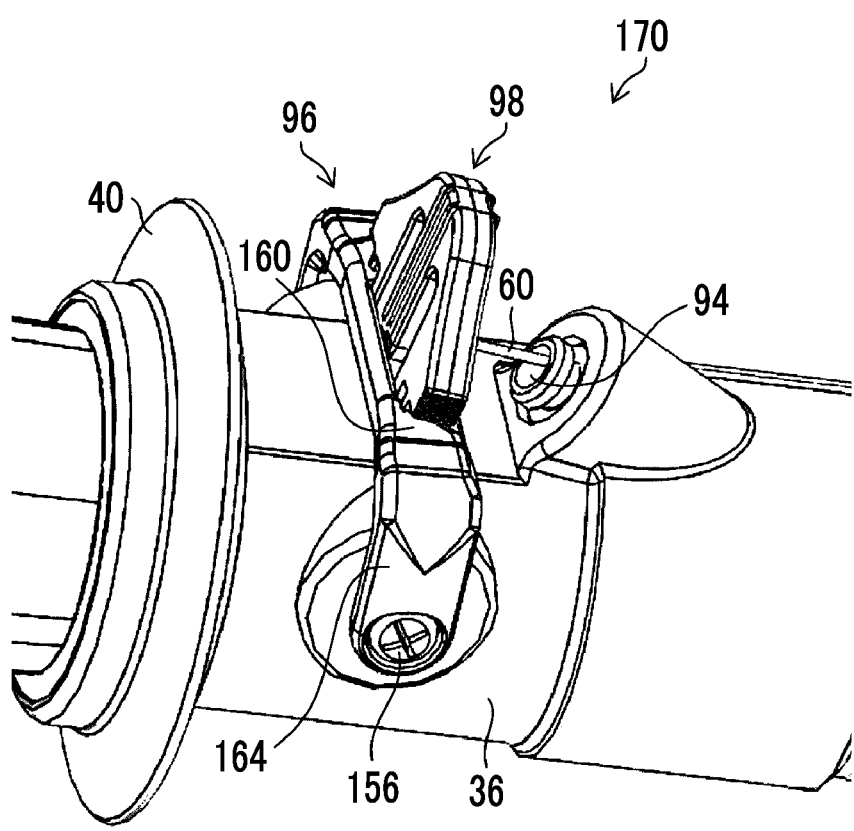
FIG. 12 is a perspective view of the connection structure shown in FIG. 11 that is viewed from the left side.

FIG. 11 is a perspective view of the connection structure 170 that is viewed from the other side surface 22B of the operation unit 22. Further, FIG. 12 is a perspective view of the connection structure 170 shown in FIG. 11 that is viewed from the left side.

Figure 13:
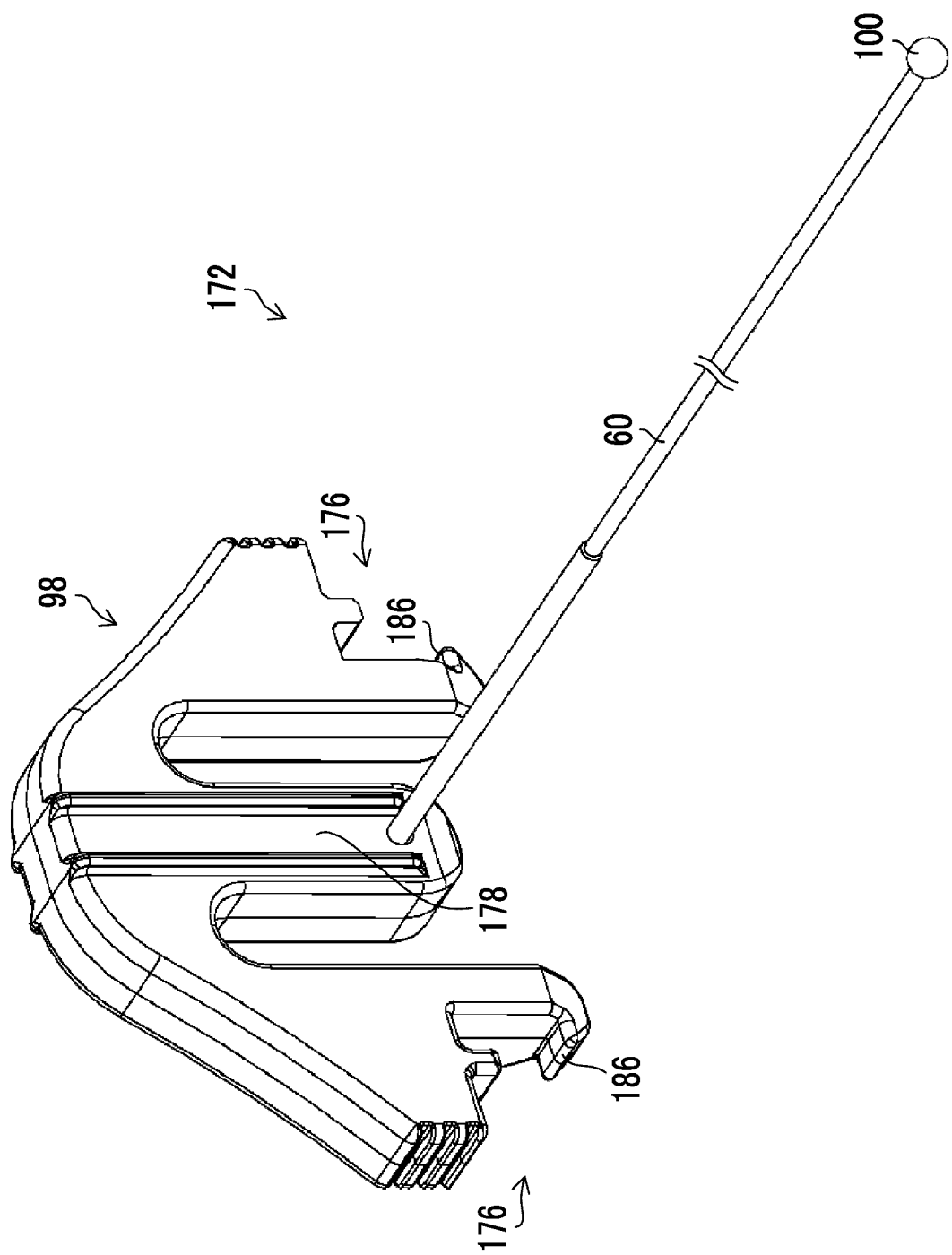
FIG. 13 is a perspective view of a wire assembly.
Figure 14:
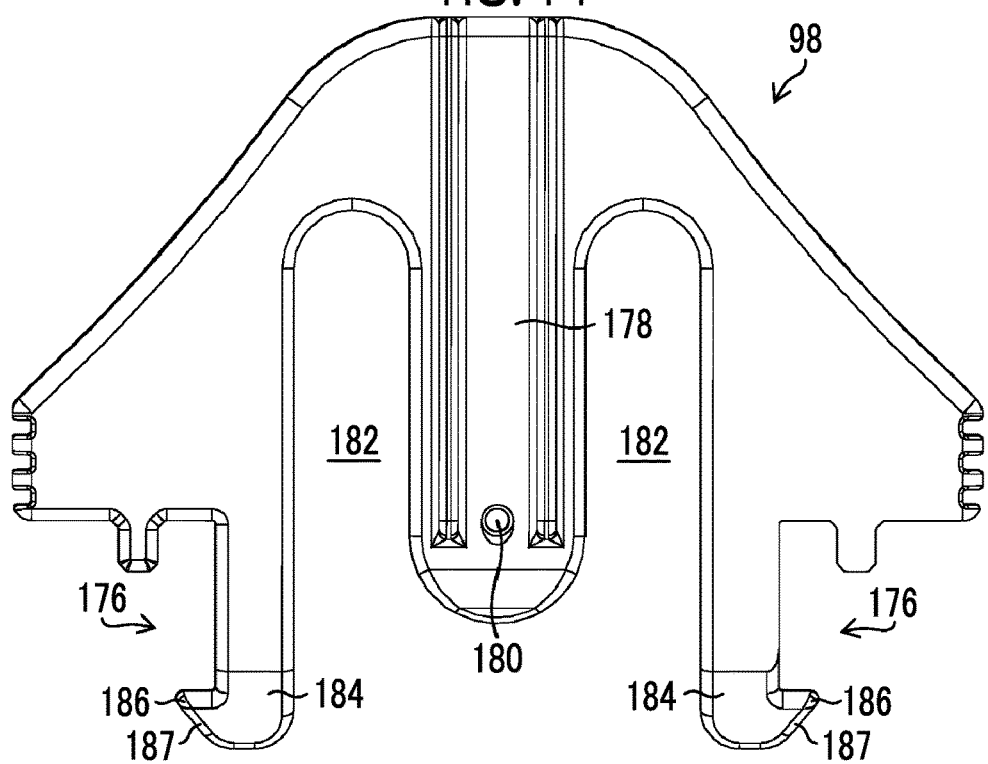
FIG. 14 is a front view of a mounting member.

Furthermore, FIG. 13 is a perspective view of a wire assembly 172 that comprises the wire 60 and the mounting member 98 provided at the proximal end of the wire 60, FIG. 14 is a front view of the mounting member 98, and FIG. 15 is a perspective view of the extending part 36 showing the inlet 94 and the movable member 96.

FIGS. 11 to 15 are diagrams illustrating the connection structure 170. Among FIGS. 11 to 15, FIGS. 11 and 12 show that the proximal end of the wire 60 and the movable member 96 are connected to each other by the connection structure 170, and FIGS. 13 to 15 show the mounting member 98 and the movable member 96 of the connection structure 170.

As shown in FIG. 15, the movable member 96 is provided with an engaging hole 174 with which the mounting member 98 is to be attachably and detachably engaged with one touch. The engaging hole 174 is formed of a through hole that is formed so as to extend in the longitudinal direction of the beam portion 160 of the movable member 96 and penetrates the surface and back of the beam portion 160. A pair of engaging portions 176 and 176 (see FIG. 14) of the mounting member 98 is attachably and detachably engaged with the engaging hole 174 with one touch. That is, the mounting member 98 is attachably and detachably engaged with the movable member 96 with one touch. Therefore, according to the connection structure 170 of the first embodiment, the proximal end of the wire 60 and the movable member 96 are connected to each other outside the operation unit 22. The engaging hole 174 may be a recessed non-through hole that does not penetrate the surface and back of the beam portion 160.

In this specification, "attachably and detachably engaged with one touch" means that an operation for mounting the mounting member 98 on the movable member 96 and an operation for disengaging the mounting member 98 from the movable member 96 are performed by only the operation of the mounting member 98 relative to the movable member 96 without the use of other fixing tools (for example, screws, bolts, nuts, or the like). The same applies to other embodiments to be described later.

The mounting member 98 shown in FIG. 14 is a substantially triangular plate-like body, and a hole portion 180 to which the proximal end of the wire 60 is to be connected is formed in a core portion 178 formed in the central portion of the mounting member 98. The engaging portions 176 and 176 of the mounting member 98 are provided on both sides of the core portion 178 with slit-like notches 182 interposed between the core portion 178 and themselves, and are provided with a pair of elastically deformable portions 184 that is elastically deformed to be engaged with the engaging hole 174. A pair of claw portions 186, which is to be locked to both edge portions 175 and 175 (see FIGS. 15 and 16) of the engaging hole 174 in the longitudinal direction, is formed at the elastically deformable portions 184. In a case where the engaging hole 174 and the engaging portions 176 are engaged with each other or disengaged from each other, the pair of claw portions 186 is displaced so as to approach each other through the elastic deformation of the pair of elastically deformable portions 184.

Next, a procedure for connecting the proximal end of the wire 60 to the movable member 96 by the connection structure 170 of the first embodiment will be described with reference to FIGS. 16 to 18.

Before the proximal end of the wire 60 is connected to the movable member 96, the distal end of the wire 60 is connected to the elevator 30 first.

FIG. 16 is a diagram illustrating that the wire 60 is inserted through the inlet 94 so that the engaging member 100 (see FIG. 13) is a leading end, and the distal end of the wire 60 is connected to the elevator 30 by an operation for inserting the wire 60.

That is, in a case where the wire 60 is introduced through the inlet 94 as shown in FIG. 16 so that the engaging member 100 is a leading end in a state where the elevator 30 is positioned at the elevated position (see FIG. 3), the engaging member 100 is led out of the outlet 74 through the wire channel 62 (see FIG. 2) to the outside. Then, due to a continuous operation for introducing the wire 60, the engaging member 100 is guided toward the opening 104 of the housing groove 102 of the elevator 30 by the guide portion 106 for engagement shown in FIG. 3 and is engaged with the housing groove 102 through the opening 104. Accordingly, the distal end of the wire 60 is connected to the elevator 30.

Figure 17:
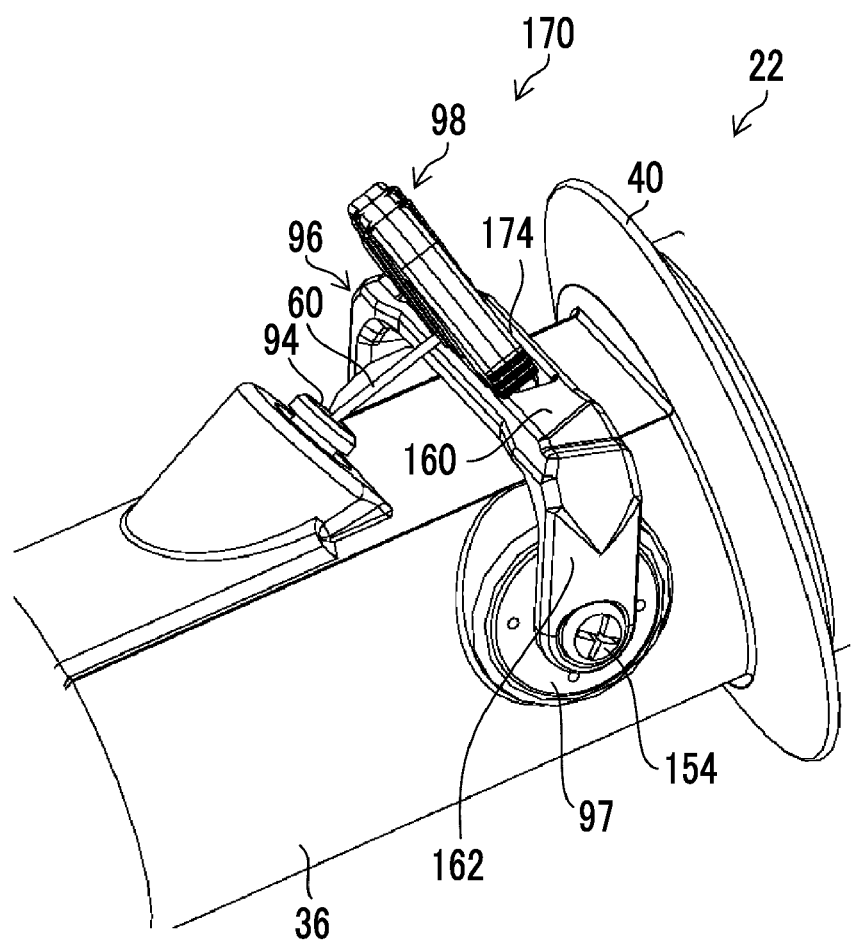
FIG. 17 is a diagram illustrating the mounting member in a state where the distal end of the wire is connected to the elevator.
Figure 18:
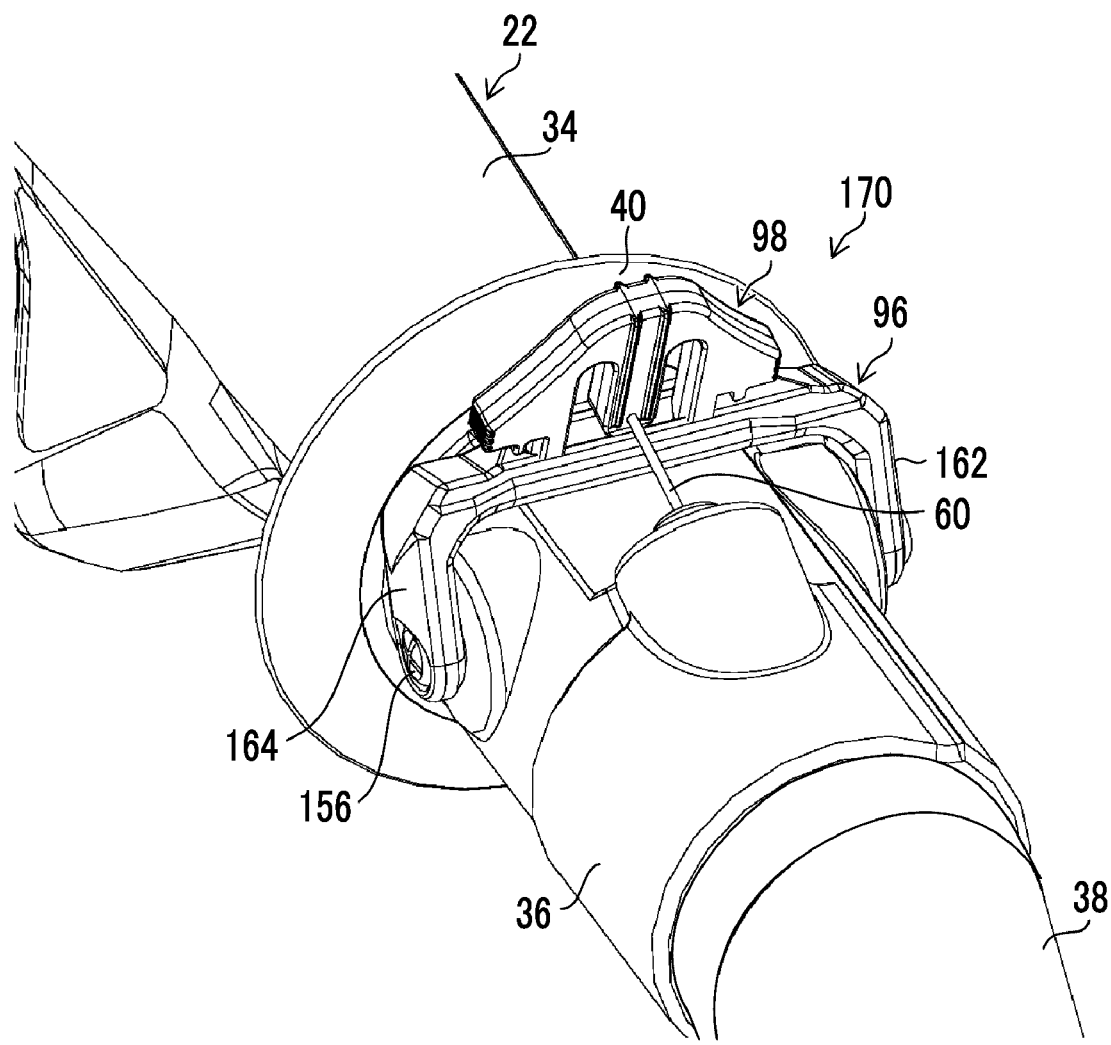
FIG. 18 is a diagram illustrating that the mounting member is connected to the movable member.

FIG. 17 shows the state of the mounting member 98 in a state where the distal end of the wire 60 is connected to the elevator 30. In this state, tapered portions 187 formed at the lower portions of the claw portions 186 are in contact with both the edges of the engaging hole 174 and are pushed. An interval between the claw portions 186 and 186 is reduced by this operation, so that the claw portions 186 and 186 are locked to both the edge portions 175 and 175 of the engaging hole 174. Accordingly, the mounting member 98 is connected to the movable member 96 as in a connection diagram shown in FIG. 18.

Therefore, according to the connection structure 170 of the first embodiment, an operation for mounting the mounting member 98 on the movable member 96 can be performed by only the operation of the mounting member 98 relative to the movable member 96. That is, according to the connection structure 170 of the first embodiment, the mounting member 98 can be engaged with the movable member 96 with one touch.

In a case where a user mounts the mounting member 98 on the movable member 96, the user can pinch the pair of engaging portions 176 and 176 of the mounting member 98 with fingers and can also reduce an interval between the claw portions 186 and 186 so that the interval is smaller than the length of the engaging hole 174 in the longitudinal direction. That is, the pair of elastically deformable portions 184 is displaced so as to approach each other through elastic deformation. Then, after the claw portions 186 and 186 are inserted into the engaging hole 174, the user releases the force of the fingers and increases the interval between the claw portions 186 and 186 to lock the claw portions 186 and 186 to both the edge portions 175 and 175 of the engaging hole 174. Accordingly, the mounting member 98 is engaged with the movable member 96 with one touch.

As shown in FIG. 12, the leg portion 164 of the movable member 96 is rotatably supported on the driven shaft 168 (not shown) by a fixing screw 156.

Further, the engaging hole 174 has been formed in the movable member 96 and the engaging portions 176 have been formed at the mounting member 98 in the embodiment, but the engaging portions 176 may be formed at the movable member 96 and the engaging hole 174 may be formed in the mounting member 98. That is, any one of the movable member 96 or the mounting member 98 may be provided with the engaging hole 174 and the other thereof may be provided with the engaging portions 176 that are to be attachably and detachably engaged with the engaging hole 174 with one touch. Furthermore, the claw portions 186 may be provided on the beam portion 160 of the movable member 96 not in the longitudinal direction but in a lateral direction. Moreover, the engaging hole 174 may be two engaging holes that are formed so as to be separated from each other in the longitudinal direction of the beam portion 160.

Incidentally, the endoscope 10 is used for various examinations or treatments. Then, the following work is performed in a case where the endoscope 10 is to be washed.

First, the user detaches the cap 76 shown in FIG. 2 from the distal end member 28. Then, the user detaches the engaging portions 176 and 176 of the mounting member 98 from the engaging hole 174 (see FIG. 15) of the movable member 96 and detaches the wire 60 from the movable member 96. Next, the user pushes the wire 60 from the inlet 94 of the extending part 36 and positions the elevator 30 to the fallen position shown in FIG. 2 from the elevated position shown in FIG. 3. After that, in a case where the user further pushes the wire 60, the engaging member 100 is disengaged from the inside of the housing groove 102 to the outside of the opening 104. The distal end of the wire 60 is detached from the elevator 30 by this work. Next, the user pulls the wire 60 out of the inlet 94 to empty the wire channel 62. After that, the distal end member 28, the elevator 30, and the wire channel 62 for the wire 60 are washed.

In the work for detaching the distal end of the wire 60 from the elevator 30, the mounting member 98 can be easily detached from the movable member 96 since the mounting member 98 of the connection structure 170 of the first embodiment is connected to the movable member 96 outside the operation unit 22. Specifically, the user pinches the pair of engaging portions 176 and 176 of the mounting member 98 with fingers and reduces the interval between the claw portions 186 and 186 so that the interval is smaller than the length of the engaging hole 174 in the longitudinal direction. After that, the user pulls the claw portions 186 and 186 out of the engaging hole 174.

Accordingly, according to the connection structure 170 of the first embodiment, an operation for disengaging the mounting member 98 from the movable member 96 can be performed by only the operation of the mounting member 98 relative to the movable member 96. That is, according to the connection structure 170 of the first embodiment, the mounting member 98 can be disengaged from the movable member 96 with one touch.

As described above, according to the connection structure 170 of the first embodiment, it is possible to connect the proximal end of the wire 60 to the movable member 96 by merely engaging the engaging portions 176 and 176 of the mounting member 98 with the engaging hole 174 of the movable member 96 outside the operation unit 22 after the distal end of the wire 60 is connected to the elevator 30. Further, in a case where the proximal end of the wire 60 is to be detached from the movable member 96 to wash the endoscope 10, it is possible to detach the proximal end of the wire 60 from the movable member 96 by merely detaching the mounting member 98 from the engaging hole 174 of the movable member 96 outside the operation unit 22.

Therefore, according to the connection structure 170 of the first embodiment, operations for attaching and detaching the proximal end of the wire 60 to and from the movable member 96 can be easily performed in comparison with the endoscope disclosed in JP1994-315458A (JP-H06-315458A) where work for attaching and detaching the proximal end of a wire to and from a connection tool is performed inside an operation unit and the endoscope disclosed in EPI 759626B where the distal end of a cable cord is attachably and detachably mounted on a collet and a nut.

The wire 60 has been pulled out of the inlet 94 in the above-mentioned embodiment, but the wire 60 may be pulled out of the outlet 74 of the distal end member 28. In this case, the wire 60 can be pulled out of the outlet 74 in a case where the mounting member 98 is detached from the proximal end of the wire 60 prior to the pull of the wire 60.

Next, the operation of the movable member 96 using the elevating operation lever 20 will be described. As shown in FIG. 19, an operator can move the elevating operation lever 20 between in a movable region (between a position P1 and a position P2). The rotating body 97 is rotated depending on the operation of the elevating operation lever 20. The movable member 96 mounted on the rotating body 97 is rotationally moved between a position Q1 and a position Q2. In a case where the operator positions the elevating operation lever 20 to a position P3 from the position P1, the mounting member 98 is positioned to a position Q3 from the position Q1. In a case where the elevating operation lever 20 is operated toward a position P4 beyond the position P3 (in a case where the mounting member 98 starts to be rotationally moved to a position Q4 from the position Q3), the elevator 30, which is positioned at the maximum fallen position in a case where the elevating operation lever 20 is positioned between the position P1 and the position P3, starts to be elevated from the maximum fallen position. Further, in a case where the elevating operation lever 20 is positioned at the position P4, the mounting member 98 is positioned at the position Q4 and the elevator 30 is positioned at the maximum elevated position. The endoscope 10 is assembled on the basis of a soft part 54 having a standard length and the wire 60 so that the elevator 30 can be rotationally moved in a range between the maximum fallen position and the maximum elevated position in a case where the elevating operation lever 20 is positioned in an operating range between the positions P3 and P4.

As shown in FIG. 19, the movable range (the positions Q1 and Q2) of the movable member 96 and the elevator operating range (between the positions Q3 and Q4) of the movable member 96 do not coincide with each other. A width between the positions P1 and P3 is determined in consideration of a trajectory along which the wire 60 is moved in the insertion unit 24 so that the elevator 30 is positioned at the maximum fallen position by the further push of the elevator 30. Further, a width between the positions P2 and P4 is determined so that tension can be further applied to the elevator 30 positioned at the maximum elevated position.

In one type of endoscope 10 comprising the elevator 30, it is preferable that the elevator 30 is positioned at the maximum fallen position in a case where the elevating operation lever 20 is positioned at the position P3 by an operator and the elevator 30 is positioned at the maximum elevated position in a case where the elevating operation lever 20 is positioned at the position P4 by an operator. Operational feel varies in a case where there is variation among the endoscopes 10 in facilities including a plurality of endoscopes 10. Accordingly, in a case where individual differences between the endoscopes 10 are removed so that the elevator 30 is operated with the same operational feel, an operator can perform a manipulation without a sense of incongruity.

However, the assembly tolerance of the endoscope 10 and the tolerance of components are present. In a case where assembly tolerance and component tolerance are present in the soft part 54 of the insertion unit 24, variations occur in a length from the proximal end to the distal end of the insertion unit 24. The operating range (between the positions P3 and P4) of the elevating operation lever 20 may be changed in a case where relative variation is present between the length of the soft part 54 and the length of the wire 60.

Figure 20:
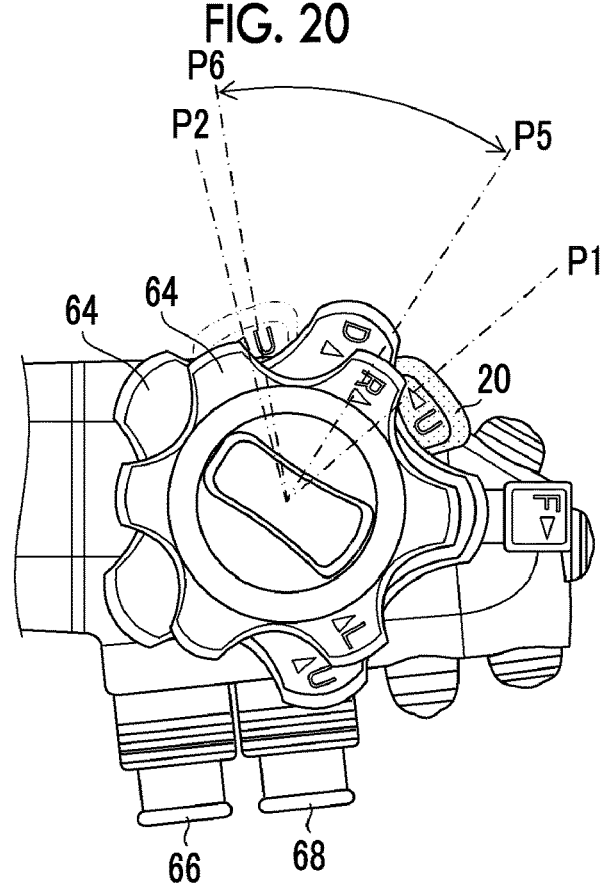
FIG. 20 is a diagram illustrating the operating range of the elevating operation lever in a case where a soft part is short.

For example, in a case where the endoscope 10 is assembled on the basis of a standard soft part 54 and the length of the wire 60 shown in FIG. 19 in a state where the soft part 54 is short, the operating range of the elevating operation lever 20 for operating the elevator 30 is positioned closer to the distal end side than that in FIG. 19 as shown in FIG. 20 so that the positions of the elevating operation lever 20 where the elevator 30 is positioned at the maximum fallen position and the maximum elevated position are changed to a position P5 from the position P3 and to a position P6 from the position P4. As a result, since the elevator 30 cannot be pulled, there is a concern that a treatment tool 56 having a large diameter may not be elevated.

Figure 21:
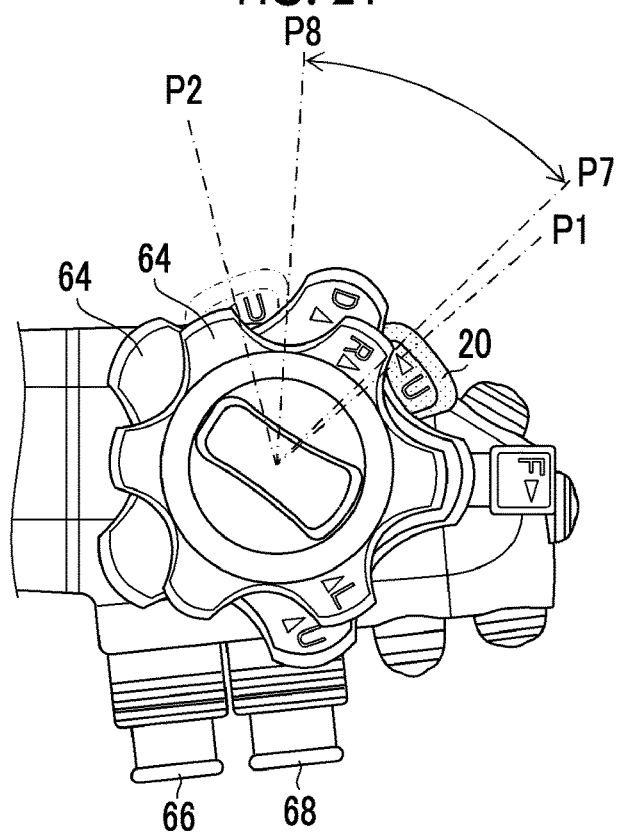
FIG. 21 is a diagram illustrating the operating range of the elevating operation lever in a case where the soft part is longer than a design specification.

Further, in a case where the endoscope 10 is assembled on the basis of the standard soft part 54 and the length of the wire 60 shown in FIG. 19 in a state where the soft part 54 is long, the operating range of the elevating operation lever 20 for operating the elevator 30 is positioned closer to the proximal end side than that in FIG. 19 as shown in FIG. 21 so that the positions of the elevating operation lever 20 where the elevator 30 is positioned at the maximum fallen position and the maximum elevated position are changed to a position P7 from the position P3 and to a position P8 from the position P4. As a result, since the length of the wire 60 is not long enough, the elevator 30 is not fallen. For this reason, there is a concern that the insertability of the treatment tool 56 may be adversely affected.

In a case where variations occur in the length of the soft part 54, the operating ranges of the elevating operation lever 20, which are required in a case where the elevator 30 is operated to the maximum fallen position and the maximum elevated position, do not coincide with each other as shown in FIGS. 19, 20, and 21.

Accordingly, the connection position of the movable member 96 in the rotation direction of the rotating body 97 is adjusted according to the aspects of the variation of the soft part 54 in the embodiment, so that the operating ranges of the elevating operation lever 20, which allow the elevator 30 to be positioned at the maximum fallen position and the maximum elevated position, are made to coincide with each other even though variations occur in the soft part 54. The aspects will be described below.

Figure 22:
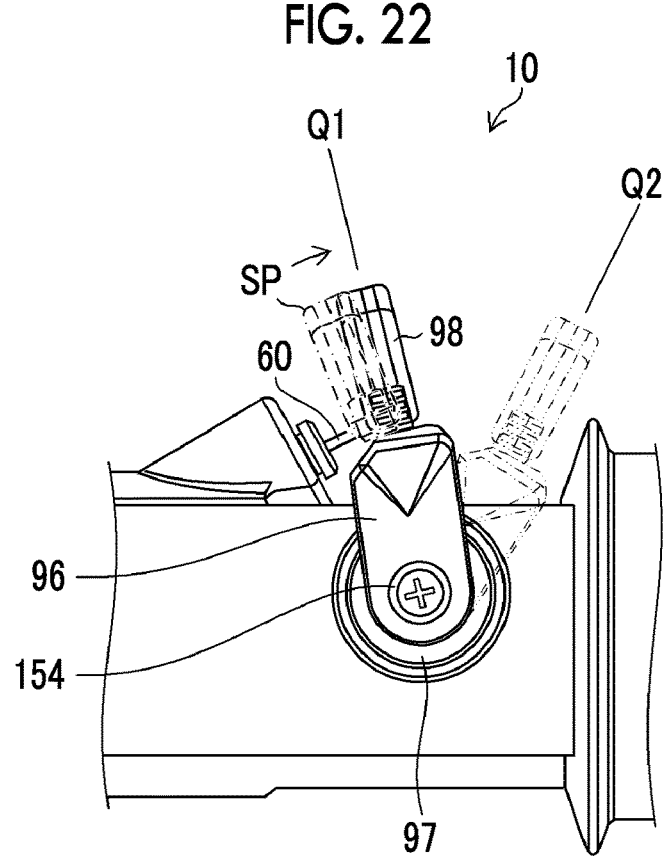
FIG. 22 is a diagram showing a connection position where the movable member and a rotating body are connected to each other in a case where the soft part is shorter than the design specification.

FIG. 22 shows a connection position between the movable member 96 and the rotating body 97 in a case where the soft part 54 is shorter than the standard soft part 54. As shown in FIG. 22, the movable member 96 is shifted to be connected at a position closer to the proximal end side than the position SP of the movable member 96, which is obtained in the case of the length of the standard soft part 54 shown in FIG. 19, in the rotation direction of the rotating body 97. Since the connection position between the movable member 96 and the rotating body 97 is shifted to the proximal end side, the operating range (between the position P5 and the position P6) of the elevating operation lever 20 for the elevator 30, which is positioned close to the distal end side and is shown in FIG. 20, can be changed to the operating range (between the position P3 and the position P4) of the elevating operation lever 20 for the elevator 30 shown in FIG. 19.

Figure 23:
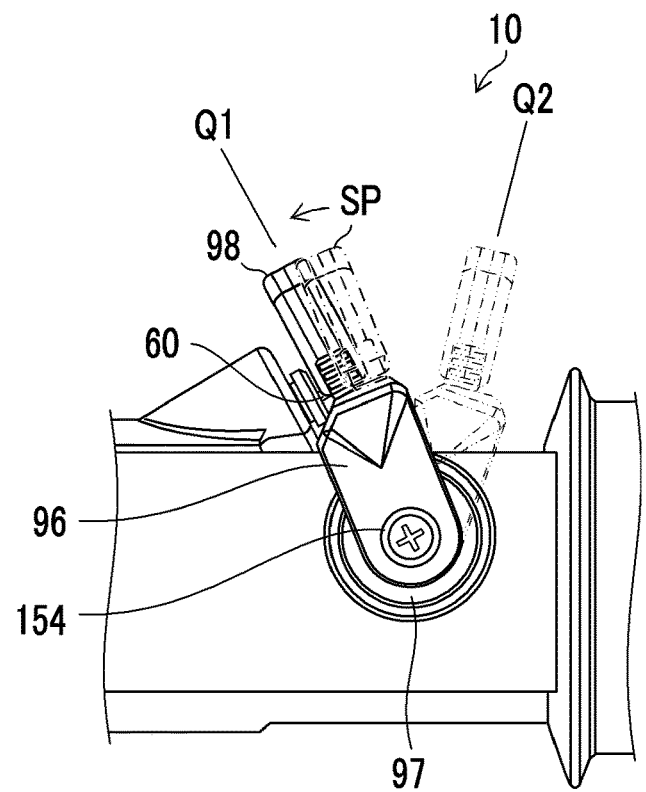
FIG. 23 is a diagram showing a connection position where the movable member and the rotating body are connected to each other in a case where the soft part is longer than the design specification.

FIG. 23 shows the connection position between the movable member 96 and the rotating body 97 in a case where the soft part 54 is longer than the standard soft part 54. As shown in FIG. 23, the movable member 96 is shifted to be connected at a position closer to the distal end side than the position SP of the movable member 96, which is obtained in the case of the length of the standard soft part 54 shown in FIG. 19, in the rotation direction of the rotating body 97. Since the connection position between the movable member 96 and the rotating body 97 is shifted to the distal end side, the operating range (between the position P7 and the position P8) of the elevating operation lever 20 for the elevator 30, which is positioned close to the proximal end side and is shown in FIG. 21, can be changed to the operating range (between the position P3 and the position P4) of the elevating operation lever 20 for the elevator 30 shown in FIG. 19.

According to the embodiment, since the operating range (between the position P3 and the position P4) of the elevating operation lever 20 for the elevator 30 can be adjusted even though variations in the length of the soft part 54 and the length of the wire 60 occur, it is possible to provide the same operational feel to the operator in the operation of the elevator 30 that uses the elevating operation lever 20.

The adjustment of the connection position between the movable member 96 and the rotating body 97 shown in FIGS. 22 and 23 can be performed in the following procedure.

For example, a standard wire used to adjust the connection position is prepared. The standard wire includes the wire 60 of which the distal end is provided with the engaging member 100 and the mounting member 98 that is provided at the proximal end of the wire 60.

In a case where the endoscope 10 is manufactured and assembled, the distal end of the standard wire is mounted on the elevator 30 and the mounting member 98 is mounted on the movable member 96. The connection position of the movable member 96 is adjusted in the rotation direction of the rotating body 97 by a fastening adjustment member so that the elevator 30 is positioned at the maximum fallen position in a case where the elevating operation lever 20 is positioned at the position P3 and the elevator 30 is positioned at the maximum elevated position in a case where the elevating operation lever 20 is positioned at the position P4. After the adjustment of the connection position ends, the standard wire is detached. After the connection position is adjusted for each endoscope 10, each endoscope 10 is shipped as a product.

Since the connection position has been adjusted, an operator does not need to adjust the connection position between the movable member 96 and the rotating body 97 in a case where the operator engages the wire 60 with the elevator and mounts the mounting member 98 on the movable member 96.

Figure 24:
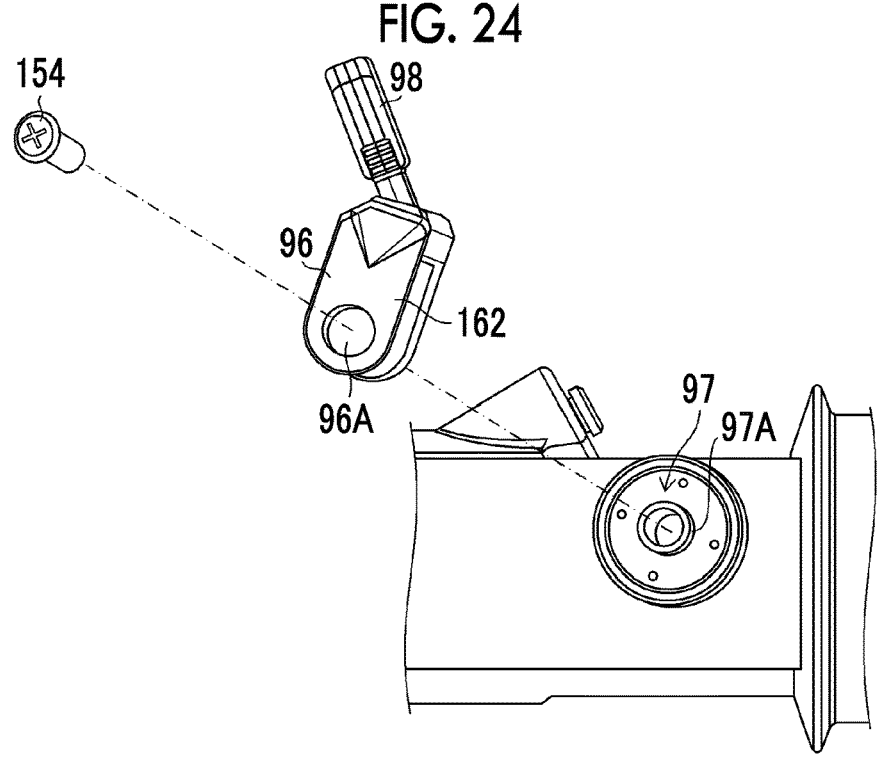
FIG. 24 is a diagram showing a position adjustment member of a first example.

FIG. 24 is an exploded view of a part of the endoscope, and is a diagram illustrating the configuration of a position adjustment member of a first example that can adjust the connection position between the movable member 96 and the rotating body 97. As shown in FIG. 24, the endoscope 10 comprises the rotating body 97 that operates in conjunction with the operation of the elevating operation lever 20, the movable member 96 that is attachably and detachably connected to the rotating body 97, and the fixing screw 154 that fixes the movable member 96 to the rotating body 97.

A through hole 96A is formed in the leg portion 162 of the movable member 96. The rotating body 97 comprises a tubular protruding portion 97A that is fitted to the drive shaft 152 (not shown). The protruding portion 97A of the rotating body 97 is inserted into the through hole 96A of the movable member 96, so that the protruding portion 97A as a part of the rotating body 97 is housed in the through hole 96A serving as a housing portion. The movable member 96 is rotatably supported by the rotating body 97. According to this configuration, the movable member 96 can select any position in the rotation direction of the rotating body 97. The through hole 96A is also referred to as a bearing.

Since the movable member 96 and the rotating body 97 are fixed to each other by the fixing screw 154 in a state where any position is selected, the connection position of the movable member 96 in the rotation direction of the rotating body 97 can be adjusted. The axial direction of the fixing screw 154 is parallel to the axial direction of the drive shaft 152. Here, "parallel" includes substantially parallel. As shown in FIG. 24, the fixing screw 154 and the through hole 96A serving as a housing portion housing a part of the rotating body 97 function as the position adjustment member.

Figure 25:
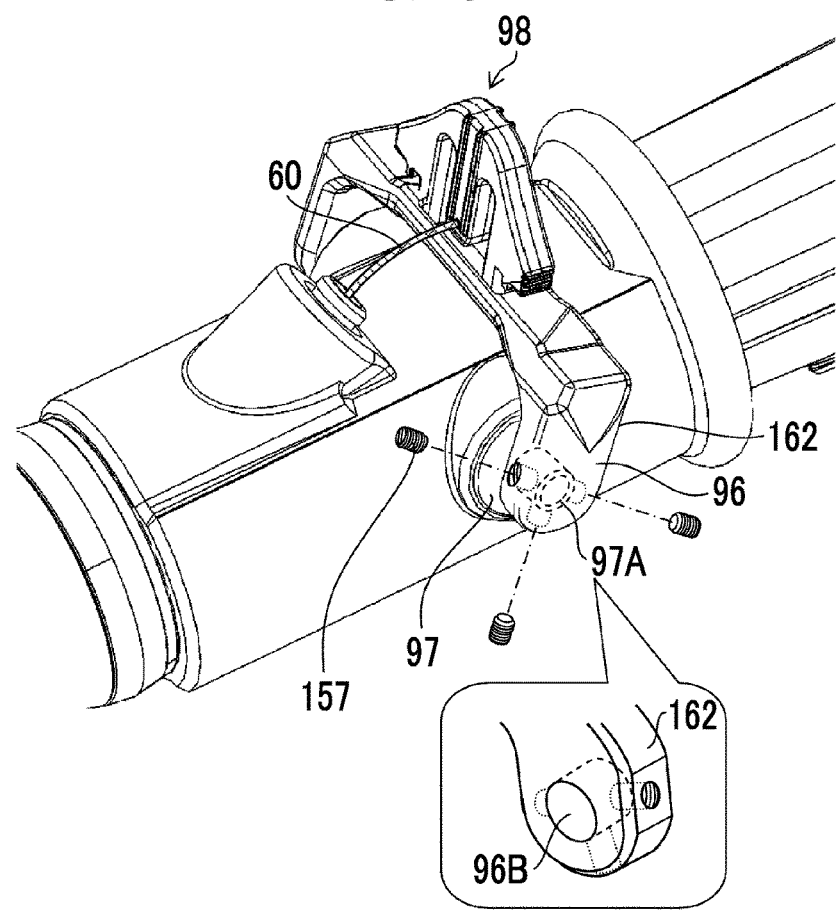
FIG. 25 is a diagram showing a position adjustment member of a second example.

FIG. 25 is a diagram showing a position adjustment member of a second example. As shown in FIG. 25, the rotating body 97 comprises a tubular protruding portion 97A that is fitted to the drive shaft 152. A recess 96B is formed in the leg portion 162 of the movable member 96 as a housing portion. The recess 96B is a space that has a bottom without penetrating the leg portion 162. The recess 96B is opened toward the protruding portion 97A. The protruding portion 97A as a part of the rotating body 97 is housed in the recess 96B of the movable member 96. The movable member 96 is rotatably supported by the rotating body 97. According to this configuration, the movable member 96 can select any position in the rotation direction of the rotating body 97. The recess 96B is also referred to as a bearing.

Since the movable member 96 and the rotating body 97 are fixed to each other by a plurality of fixing screws 157 in a state where any position is selected, the connection position of the movable member 96 in the rotation direction of the rotating body 97 can be adjusted. The axial direction of the fixing screw 157 is perpendicular to the axial direction of the drive shaft 152. Here, "perpendicular" includes substantially perpendicular. As shown in FIG. 25, the fixing screws 157 and recess 96B serving as a housing portion housing a part of the rotating body 97 function as the position adjustment member.

Figure 26:
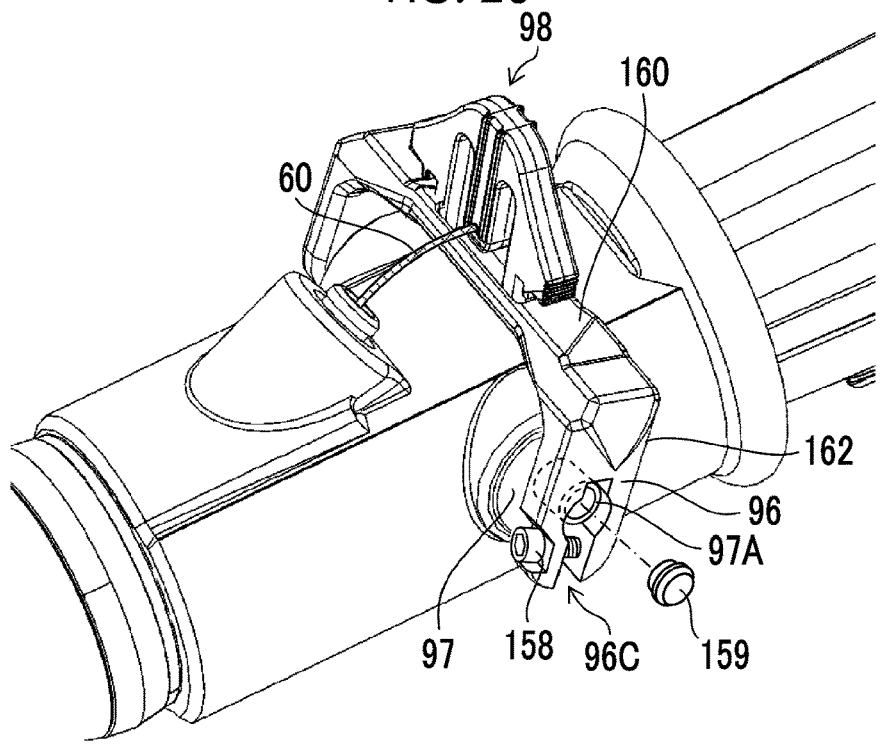
FIG. 26 is a diagram showing a position adjustment member of a third example.

FIG. 26 is a diagram showing a position adjustment member of a third example. As shown in FIG. 26, the rotating body 97 comprises a tubular protruding portion 97A that is fitted to the drive shaft 152. The distal end portion of the leg portion 162 of the movable member 96 opposite to the beam portion 160 is branched by a notch portion, so that a grip portion 96C is formed. An expanded portion is formed at the notch portion of the grip portion 96C. The protruding portion 97A as a part of the rotating body 97 is inserted into the expanded portion, so that the rotating body 97 is rotatably gripped by the grip portion 96C. According to this configuration, the movable member 96 can select any position in the rotation direction of the rotating body 97.

As shown in FIG. 26, a screw hole (not shown) is formed at the branched distal end portion of the grip portion 96C. The screw hole is positioned on one side of the expanded portion of the grip portion 96C opposite to the beam portion 160. A fastening screw 158 is inserted into the screw hole. The branched distal end portion is fastened by the fastening screw 158. The fastening screw 158 is tightened, so that a gap of the notch portion of the distal end portion is reduced. Accordingly, since the movable member 96 and the rotating body 97 are fixed to each other by the fastening screw 158 in a state where any position is selected, the connection position of the movable member 96 in the rotation direction of the rotating body 97 can be adjusted. As shown in FIG. 26, the grip portion 96C and the fastening screw 158 function as the position adjustment member.

It is preferable that a cap 159 is provided at the expanded portion of the grip portion 96C to keep the watertightness of the operation unit 22 (not shown).

Figure 27:
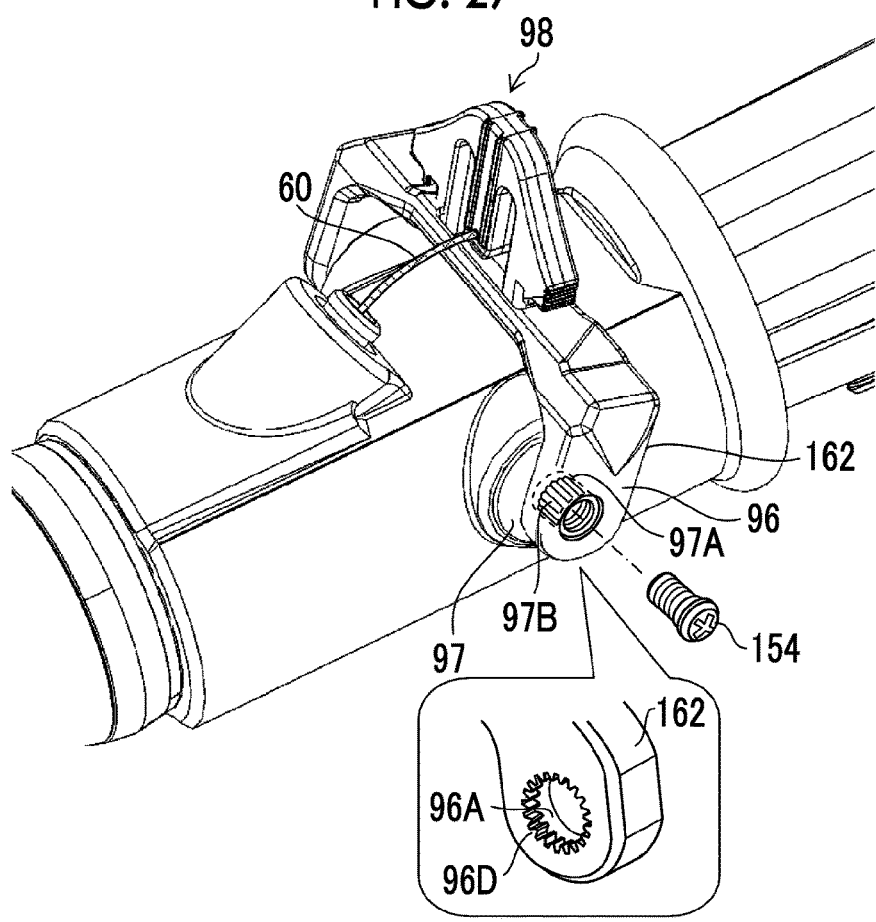
FIG. 27 is a diagram showing a position adjustment member of a fourth example.

FIG. 27 is a diagram showing a position adjustment member of a fourth example. The position adjustment member shown in FIG. 27 and the position adjustment member shown in FIG. 24 have the same basic configuration. On the other hand, unlike in FIG. 24, outer peripheral grooves 97B are formed on the outer periphery of the tubular protruding portion 97A of the rotating body 97 as shown in FIG. 27. Inner peripheral grooves 96D to be engaged with the outer peripheral grooves 97B are formed in the through hole 96A forming a housing portion of the leg portion 162 of the movable member 96. According to this configuration, the movable member 96 can select any position corresponding to a groove pitch of the inner peripheral grooves 96D and the outer peripheral grooves 97B in the rotation direction of the rotating body 97.

Since the movable member 96 and the rotating body 97 are fixed to each other by the fixing screw 154 in a state where any position is selected, the connection position of the movable member 96 in the rotation direction of the rotating body 97 can be adjusted. In addition, since the inner peripheral grooves 96D and the outer peripheral grooves 97B are engaged with each other, a positional deviation between the movable member 96 and the rotating body 97 can be suppressed. The axial direction of the fixing screw 154 is parallel to the axial direction of the drive shaft 152 (not shown). Here, "parallel" includes substantially parallel. As shown in FIG. 27, the through hole 96A serving as a housing portion housing a part of the rotating body 97, the fixing screw 154, the inner peripheral grooves 96D, and the outer peripheral grooves 97B function as the position adjustment member.

Figure 28:
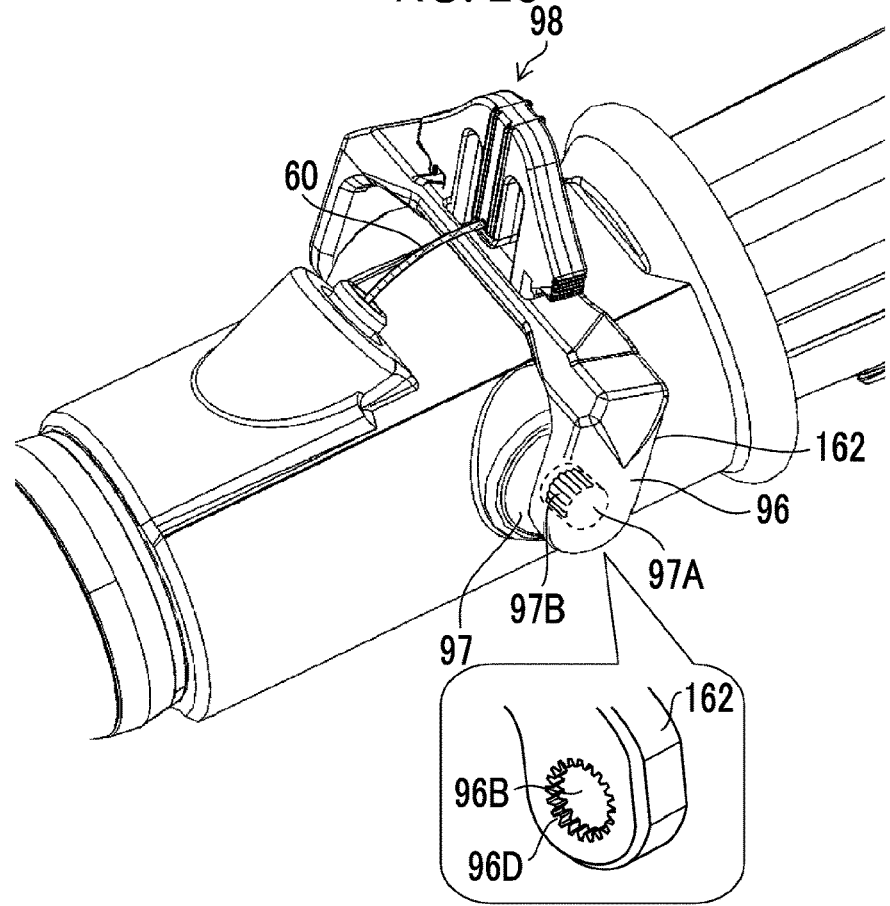
FIG. 28 is a diagram showing a position adjustment member of a fifth example.
Figure 29:
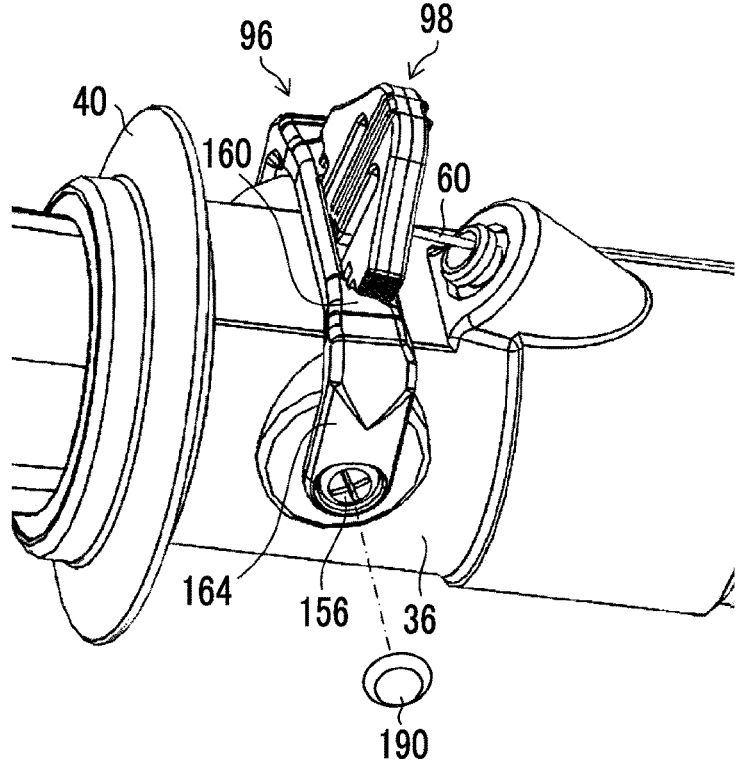
FIG. 29 is a diagram showing the position adjustment member shown in FIG. 28 that is viewed from an opposite side.

FIGS. 28 and 29 are diagrams showing a position adjustment member of a fifth example. The position adjustment member shown in FIGS. 28 and 29 and the position adjustment member shown in FIG. 27 have the same basic configuration. FIG. 29 is a perspective view of FIG. 28 that is viewed from an opposite side. Outer peripheral grooves 97B are formed on the outer periphery of a tubular protruding portion 97A of the rotating body 97.

On the other hand, a recess 96B is formed in the leg portion 162 of the movable member 96 as a housing portion. The recess 96B is a space that does not penetrate the leg portion 162. The recess 96B is opened toward the protruding portion 97A. Inner peripheral grooves 96D to be engaged with the outer peripheral grooves 97B are formed in the recess 96B. According to this configuration, the movable member 96 can select any position corresponding to the groove pitch of the inner peripheral grooves 96D and the outer peripheral grooves 97B in the rotation direction of the rotating body 97. The recess 96B is also referred to as a bearing.

Since the movable member 96 and the rotating body 97 are fixed to each other by a fixing screw 156 in a state where any position is selected, the connection position of the movable member 96 in the rotation direction of the rotating body 97 can be adjusted. The fixing screw 156 is inserted into the leg portion 164 of the movable member 96 and is fastened to the operation unit 22 (not shown). The fixing screw 156 supports the movable member 96 to allow the movable member 96 to be rotatable. Accordingly, a fixing screw is not provided at the leg portion 162 of the movable member 96 in the embodiment. The annular protruding portion 97A is sealed by the recess 96B of the leg portion 162. In addition, since the inner peripheral grooves 96D and the outer peripheral grooves 97B are engaged with each other, a positional deviation between the movable member 96 and the rotating body 97 can be suppressed. After the fixing screw 156 is tightened, a cap 190 is mounted to cover the fixing screw 156. Since the cap 190 is provided, watertightness can be kept.

The axial direction of the fixing screw 156 is parallel to the axial direction of the drive shaft 152 (not shown). Here, "parallel" includes substantially parallel. As shown in FIGS. 28 and 29, the recess 96B serving as a housing portion housing a part of the rotating body 97, the fixing screw 156, the inner peripheral grooves 96D, and the outer peripheral grooves 97B function as the position adjustment member.

The position adjustment members have been described with reference to FIGS. 24 to 29, but the configuration of the position adjustment member is not limited as long as the connection position between the movable member 96 and the rotating body 97 can be adjusted.

FIG. 30 is a perspective view showing a modification example of the connection structure 170 shown in FIGS. 11 to 18.

In the description of a connection structure 170A of a modification example shown in FIG. 30, the same members as the members of the connection structure 170 shown in FIGS. 11 to 18 or members similar to the members of the connection structure 170 will be denoted by the same reference numerals as the reference numerals shown in FIGS. 11 to 18.

An engaging hole 174A formed in a movable member 96 is a circular through hole. Further, an engaging portion 176A of a mounting member 98A includes a cylindrical portion 177 to be inserted into the engaging hole 174A. Furthermore, an elastically deformable portion of the mounting member 98A is formed of a slotted portion 184A that is provided at the distal end portion of the cylindrical portion 177, and claw portions 186A are formed on the outer peripheral surface of the slotted portion 184A.

Figure 31:
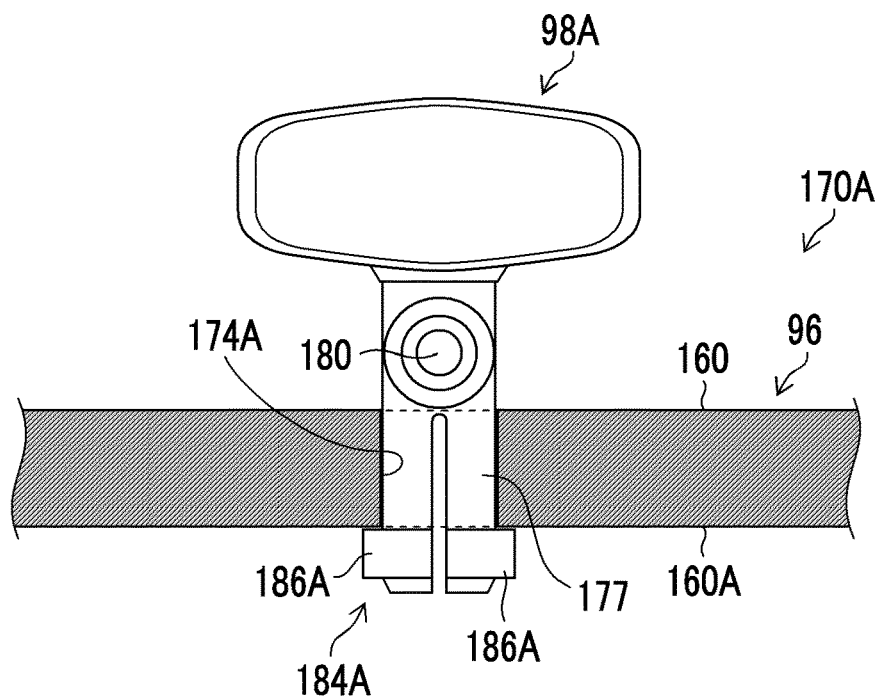

According to the connection structure 170A having the above-mentioned configuration, the slotted portion 184A is reduced in diameter by being elastically deformed in a case where the slotted portion 184A of the cylindrical portion 177 is inserted into the engaging hole 174A. Accordingly, the slotted portion 184A passes through the engaging hole 174A, and the slotted portion 184A then returns to the original diameter in a case where the slotted portion 184A has passed through the engaging hole 174A. Therefore, since the claw portions 186A of the slotted portion 184A are engaged with a back 160A of the beam portion 160 of the movable member 96 as in the cross-sectional view of the connection structure 170A shown in FIG. 31, the mounting member 98A is engaged with the movable member 96 with one touch.

Even in the case of the connection structure 170A, as in the case of the connection structure 170, work for attaching and detaching the mounting member 98A to and from the movable member 96 is performed outside the operation unit 22. For the work for mounting the mounting member 98A, a user has only to insert the engaging portion 176A into the engaging hole 174A. The proximal end of the wire 60 can be easily connected to the movable member 96 through the mounting member 98A by this work for mounting the mounting member 98A.

Further, in a case where the mounting member 98A is to be detached from the movable member 96, a user pinches the slotted portion 184A with fingers and reduces the diameter of the slotted portion 184A. Then, the user pulls the slotted portion 184A out of the engaging hole 174A.

Accordingly, even in the case of the connection structure 170A of the modification example, as in the case of the connection structure 170, each of an operation for mounting the mounting member 98A on the movable member 96 and an operation for disengaging the mounting member 98A from the movable member 96 can be performed by only the operation of the mounting member 98A relative to the movable member 96. That is, according to the connection structure 170A, the mounting member 98A is attachably and detachably engaged with the movable member 96 with one touch.

Figure 32:
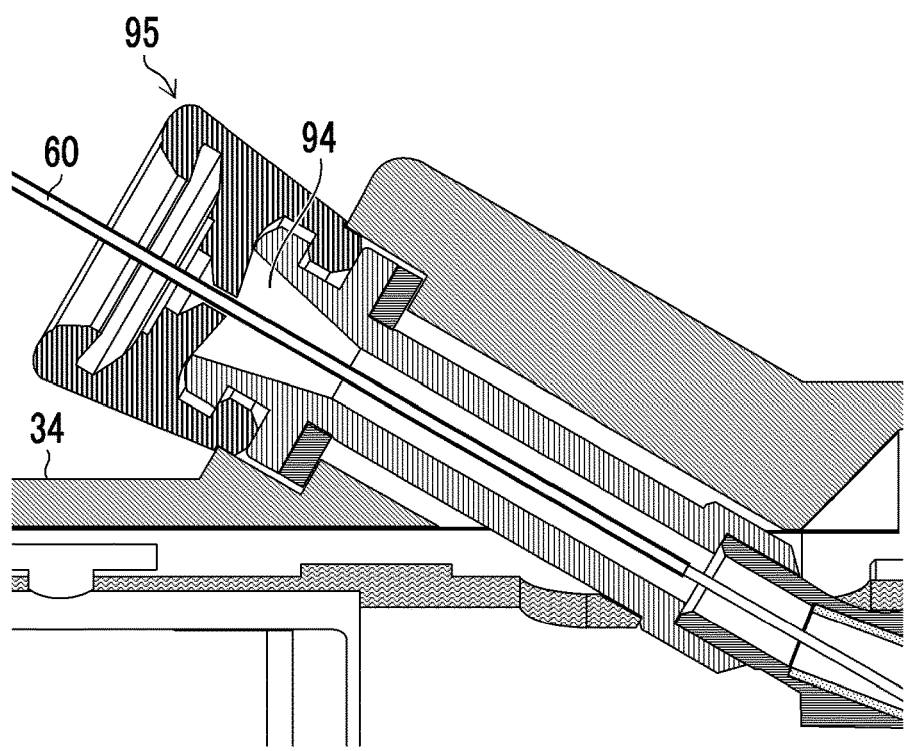
FIG. 32 is a cross-sectional view showing a state where a valve element is mounted on the inlet.

FIG. 32 is a cross-sectional view showing a state where a valve element 95 is mounted on the inlet 94. Since the proximal end of the wire 60 is disposed outside of the inlet 94 in the embodiment, it is preferable that the valve element 95 is mounted on the inlet 94. Accordingly, it is possible to prevent body cavity liquid, which flows back from the outlet 74 of the distal end member 28 through the wire channel 62, from leaking from the inlet 94.

Next, a connection structure 210 of a second aspect will be described with reference to FIGS. 33 to 35.

Figure 33:
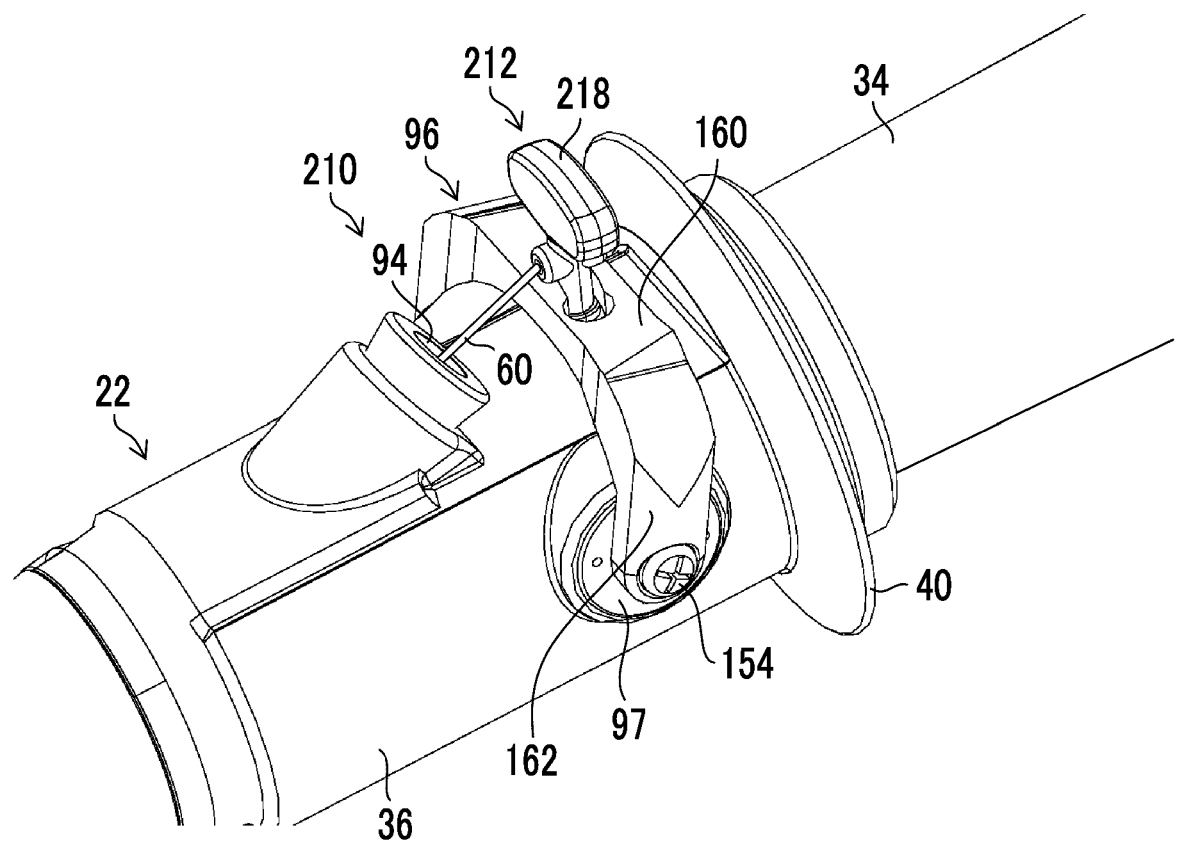
FIG. 33 is a perspective view of a connection structure of a second aspect.
Figure 35:
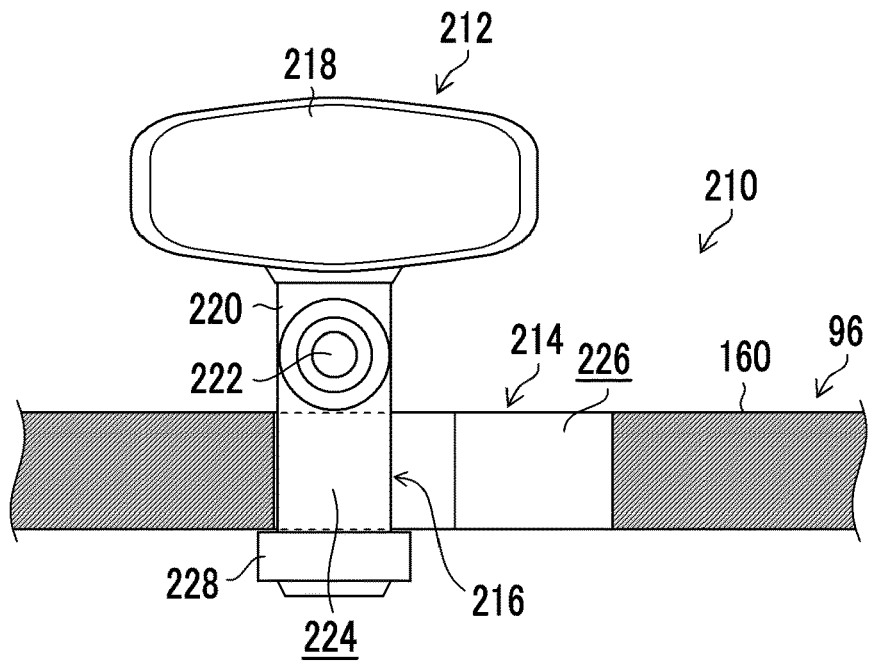

FIG. 33 is a perspective view of the connection structure 210, FIG. 34 is an exploded perspective view of the connection structure 210, and FIG. 35 is a cross-sectional view of main portions of the connection structure 210. In the description of the connection structure 210, the same members as the members of the connection structure 170 shown in FIGS. 11 to 18 or members similar to the members of the connection structure 170 will be denoted by the same reference numerals as the reference numerals shown in FIGS. 11 to 18.

The connection structure 210 includes a movable member 96 and a mounting member 212.

As shown in FIG. 34, a beam portion 160 of the movable member 96 is provided with an engaging hole 214 and the mounting member 212 is provided with an engaging portion 216 that is to be attachably and detachably engaged with the engaging hole 214 with one touch. Further, the mounting member 212 includes a knob portion 218 and a shaft portion 220 forming the engaging portion 216, and the proximal end of the wire 60 is connected to a hole portion 222 formed in the shaft portion 220.

Figure 36:
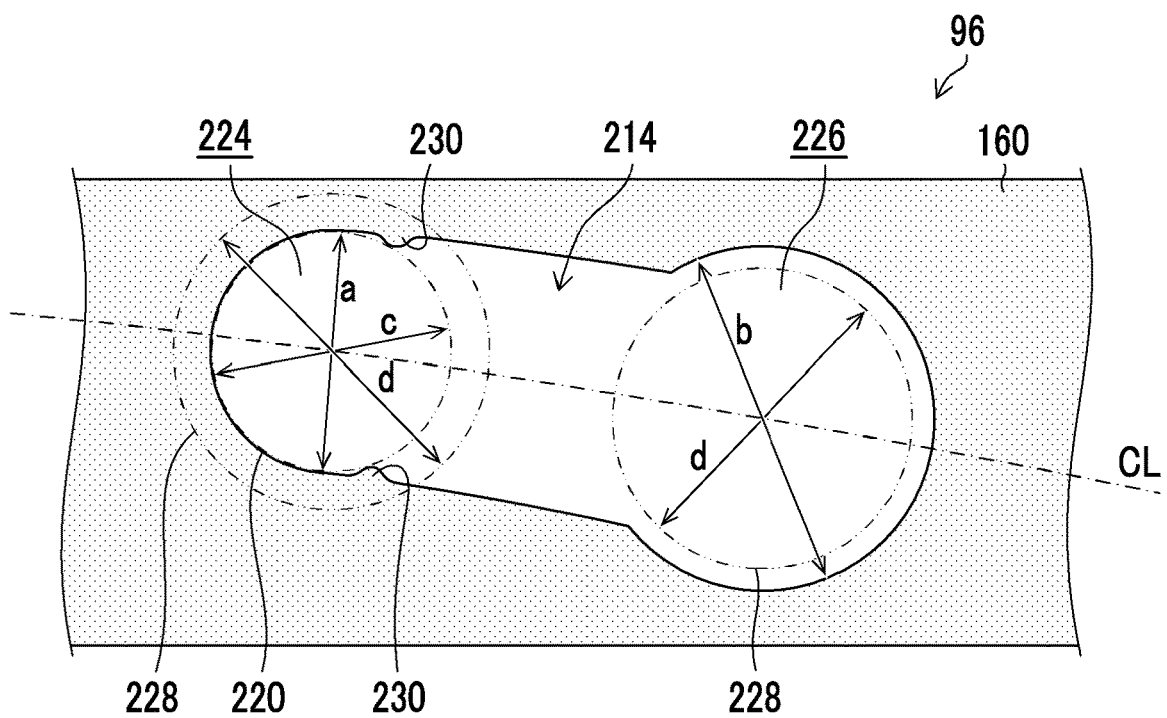
FIG. 36 is a plan view showing the size of an engaging portion with respect to an engaging hole.

Here, the shape of the engaging hole 214 will be described. FIG. 36 is a plan view of the engaging hole 214, and shows that the shape of the engaging portion 216 is superimposed on the shape of the engaging hole 214.

The engaging hole 214 includes a narrow portion 224 having a diameter a and a wide portion 226 having a diameter b larger than the diameter a. In the embodiment, a first width of the invention is described as the diameter a and a second width of the invention is described as the diameter b. As shown in FIG. 36, a line CL connecting the center of the narrow portion 224 to the center of the wide portion 226 is a curve. The line CL forms a substantially circular arc that is centered on the inlet 94 (not shown). The arrangement of the narrow portion 224 and the wide portion 226 facilitates an operation for engaging the mounting member 212 with the engaging hole 214. This will be described later.

Further, the engaging portion 216 of the mounting member 212 shown in FIG. 34 includes the shaft portion 220 that has an outer diameter c equal to or smaller than the diameter a shown in FIG. 36, and an enlarged-diameter portion 228 that is provided at the distal end of the shaft portion 220. The enlarged-diameter portion 228 has an outer diameter d that is larger than the diameter a and smaller than the diameter b. The enlarged-diameter portion 228 functions as a retaining member that regulates the disengagement of the shaft portion 220 from the narrow portion 224 in the axial direction of the shaft portion 220. For the stable holding of the shaft portion 220, it is preferable that a difference between the diameter a and the outer diameter c is small.

An engaging operation will be described. Since the wide portion 226 of the engaging hole 214 is larger than the enlarged-diameter portion 228, the engaging portion 216 of the mounting member 212 can be easily inserted into the engaging hole 214. Then, the mounting member 212 is slid to the narrow portion 224 from the wide portion 226. In that case, since the mounting member 212 is fixed to the wire 60 as shown in FIG. 33, the mounting member 212 is moved on a substantially arc-shaped trajectory that is centered on the inlet 94. Since the narrow portion 224 and the wide portion 226 are arranged along a substantially circular arc as described above, the mounting member 212 can smoothly slide between the narrow portion 224 and the wide portion 226. In addition, tension can be applied to the wire 60 in a case where the mounting member 212 is positioned in the narrow portion 224.

Furthermore, the engaging hole 214 includes friction resistance portions 230 between the narrow portion 224 and the wide portion 226. The friction resistance portions 230 are provided at an open inlet portion of the narrow portion 224. The inadvertent sliding of the shaft portion 220, which is inserted into the narrow portion 224, to the wide portion 226 from the narrow portion 224 can be regulated by the friction resistance portions 230. The friction resistance portions 230 are formed to protrude from the wall surfaces of the engaging hole 214 facing each other.

Even in the case of the connection structure 210 having this configuration, as in the case of the connection structure 170, work for attaching and detaching the mounting member 212 to and from the movable member 96 is performed outside the operation unit 22. For the work for mounting the mounting member 212, a user has only to insert the engaging portion 216 into the wide portion 226 of the engaging hole 214 and to slide the engaging portion 216 toward the narrow portion 224 to engage the engaging portion 216 with the narrow portion 224. Accordingly, the mounting member 212 is engaged with the movable member 96 with one touch. The proximal end of the wire 60 can be easily connected to the movable member 96 through the mounting member 212 by this work for mounting the mounting member 212.

Further, in a case where the engaging portion 216 is slid toward the narrow portion 224 from the wide portion 226, the shaft portion 220 is in contact with the friction resistance portions 230 but the engaging portion 216 can be engaged with the narrow portion 224 without any problems by a force for sliding the engaging portion 216.

Furthermore, in a state where the engaging portion 216 is engaged with the narrow portion 224, the disengagement of the shaft portion 220 from the narrow portion 224 in the axial direction of the shaft portion 220 is prevented by the enlarged-diameter portion 228. Moreover, since the shaft portion 220 is in contact with the friction resistance portions 230, the sliding of the engaging portion 216 to the wide portion 226 from the narrow portion 224 is regulated. Accordingly, the mounting member 212 can be reliably connected to the movable member 96.

On the other hand, in a case where a user is to detach the mounting member 212 from the movable member 96 for the washing of the endoscope 10, the user slides the engaging portion 216 of the mounting member 212 to the wide portion 226 from the narrow portion 224 and pulls the engaging portion 216 out of the wide portion 226. Accordingly, the mounting member 212 is disengaged from the movable member 96 with one touch.

Therefore, according to the connection structure 210 shown in FIGS. 33 to 35, operations for attaching and detaching the proximal end of the wire 60 to and from the movable member 96 can be easily performed in comparison with the above-mentioned endoscopes disclosed in JP1994-315458A (JP-H06-315458A) and EP1759626B.

The engaging hole 214 comprising the friction resistance portions 230 has been exemplified in FIG. 36, but an engaging hole 214 not comprising the friction resistance portions 230 may be provided.

Next, a connection structure 232 of a third aspect will be described with reference to FIGS. 37 and 38.

FIG. 37 is an exploded perspective view of the connection structure 232. FIG. 38 is a plan view of an engaging hole 214 formed in a movable member 96, and shows that the shape of an engaging portion 236 of a mounting member 234 is superimposed on the shape of an engaging hole 214. In the description of the connection structure 232, the same members as the members of the connection structure 210 shown in FIGS. 33 to 37 or members similar to the members of the connection structure 210 will be denoted by the same reference numerals as the reference numerals shown in FIGS. 33 to 36.

Figure 38:
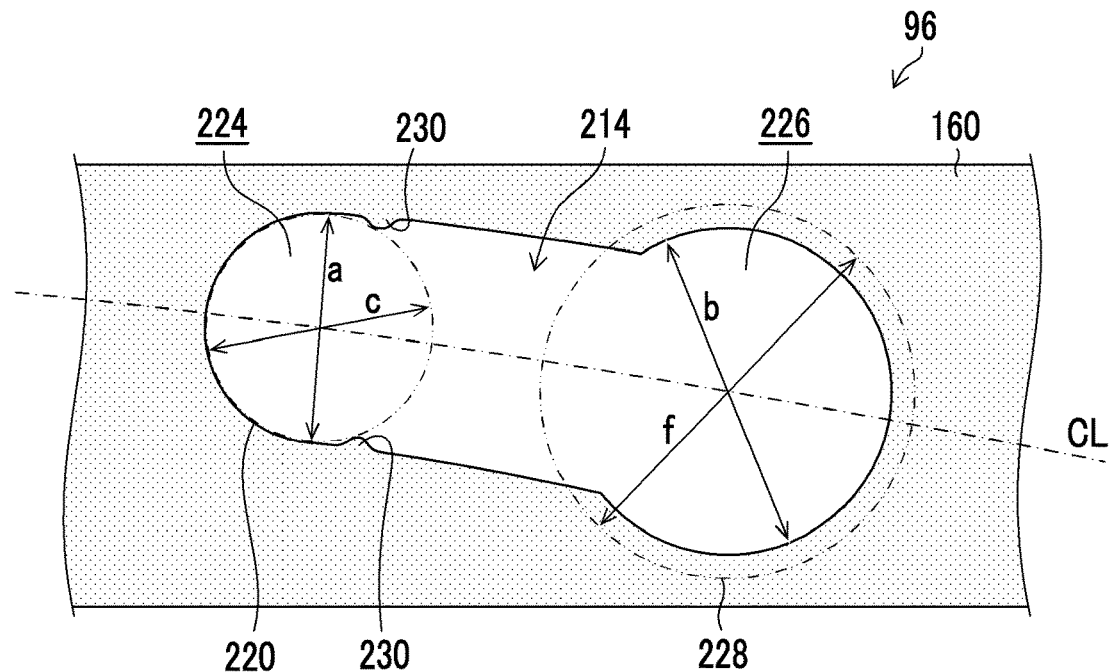
FIG. 38 is a plan view showing the size of an engaging portion with respect to an engaging hole.

As shown in FIG. 38, the engaging hole 214 includes a narrow portion 224 having a diameter a and a wide portion 226 having a diameter b larger than the diameter a. The narrow portion 224 and the wide portion 226 have the positional relationship as that shown in FIG. 36.

Further, the engaging portion 236 of the mounting member 234 shown in FIG. 37 includes: a shaft portion 220 that has an outer diameter c equal to or larger than the diameter a; and an enlarged-diameter portion 238 that is provided at the distal end of the shaft portion 220, has an outer diameter f larger than the diameter b, and includes a plurality of (for example, four) slotted grooves 237 (see FIG. 37). In a case where the enlarged-diameter portion 238 is inserted into the wide portion 226, the enlarged-diameter portion 238 is elastically deformed due to the plurality of slotted grooves 237 and is reduced in diameter. For the stable holding of the shaft portion 220, it is preferable that a difference between the diameter a and the outer diameter c is small.

Even in the case of the connection structure 232 having this configuration, as in the case of the connection structure 210, work for attaching and detaching the mounting member 234 to and from the movable member 96 is performed outside the operation unit 22. In the work for mounting the mounting member 234, first, the enlarged-diameter portion 238 is fitted into the wide portion 226 of the engaging hole 214. In that case, the enlarged-diameter portion 238 is elastically deformed due to the plurality of slotted grooves 237 and is reduced in diameter. Accordingly, the enlarged-diameter portion 238 passes through the wide portion 226, and the enlarged-diameter portion 238 then returns to the original diameter in a case where the enlarged-diameter portion 238 has passed through the wide portion 226. Therefore, since the enlarged-diameter portion 238 is engaged with a back 160A of the beam portion 160 of the movable member 96, the separation of the mounting member 234 from the movable member 96 is prevented.

After that, a user slides the engaging portion 236 toward the narrow portion 224 to engage the engaging portion 236 with the narrow portion 224. Accordingly, the mounting member 234 is engaged with the movable member 96 with one touch. The proximal end of the wire 60 can be easily connected to the movable member 96 through the mounting member 234 by this work for mounting the mounting member 234.

Further, in a state where the engaging portion 236 is engaged with the narrow portion 224, the disengagement of the shaft portion 220 from the narrow portion 224 in the axial direction of the shaft portion 220 is prevented by the enlarged-diameter portion 238. Moreover, since the shaft portion 220 is in contact with the friction resistance portions 230, the sliding of the engaging portion 236 to the wide portion 226 from the narrow portion 224 is regulated. Accordingly, the mounting member 234 can be reliably connected to the movable member 96.

On the other hand, in a case where a user is to detach the mounting member 234 from the movable member 96 for the washing of the endoscope 10, the user slides the engaging portion 236 of the mounting member 234 to the wide portion 226 from the narrow portion 224, pinches the enlarged-diameter portion 238 with fingers to reduce the diameter of the enlarged-diameter portion 238, and pulls the enlarged-diameter portion 238 out of the wide portion 226. Accordingly, the mounting member 234 is disengaged from the movable member 96 with one touch.

Therefore, according to the connection structure 232 shown in FIGS. 37 and 38, operations for attaching and detaching the proximal end of the wire 60 to and from the movable member 96 can be easily performed in comparison with the above-mentioned endoscopes disclosed in JP1994-315458A (JP-H06-315458A) and EP1759626B.

The engaging hole 214 comprising the friction resistance portions 230 has been exemplified in FIG. 38, but an engaging hole 214 not comprising the friction resistance portions 230 may be provided.

Next, a connection structure 240 of a fourth aspect will be described with reference to FIGS. 39 and 40.

Figure 39:
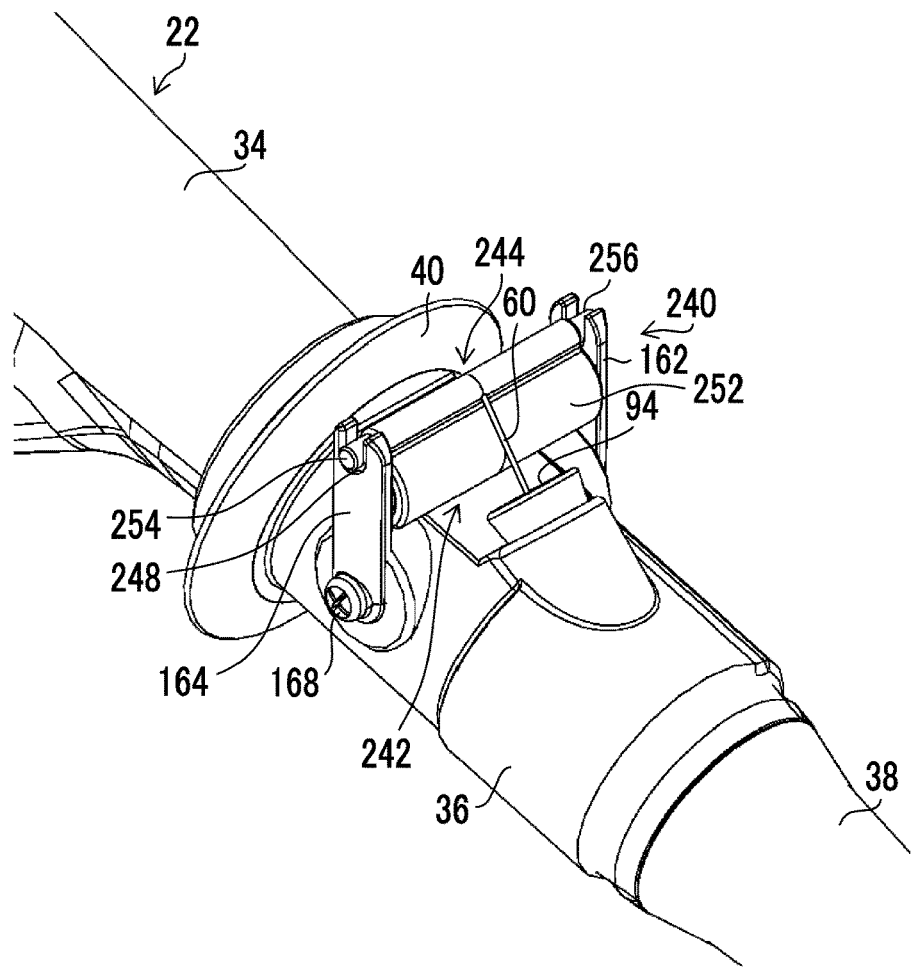
FIG. 39 is a perspective view of a connection structure of a fourth aspect.
Figure 40:
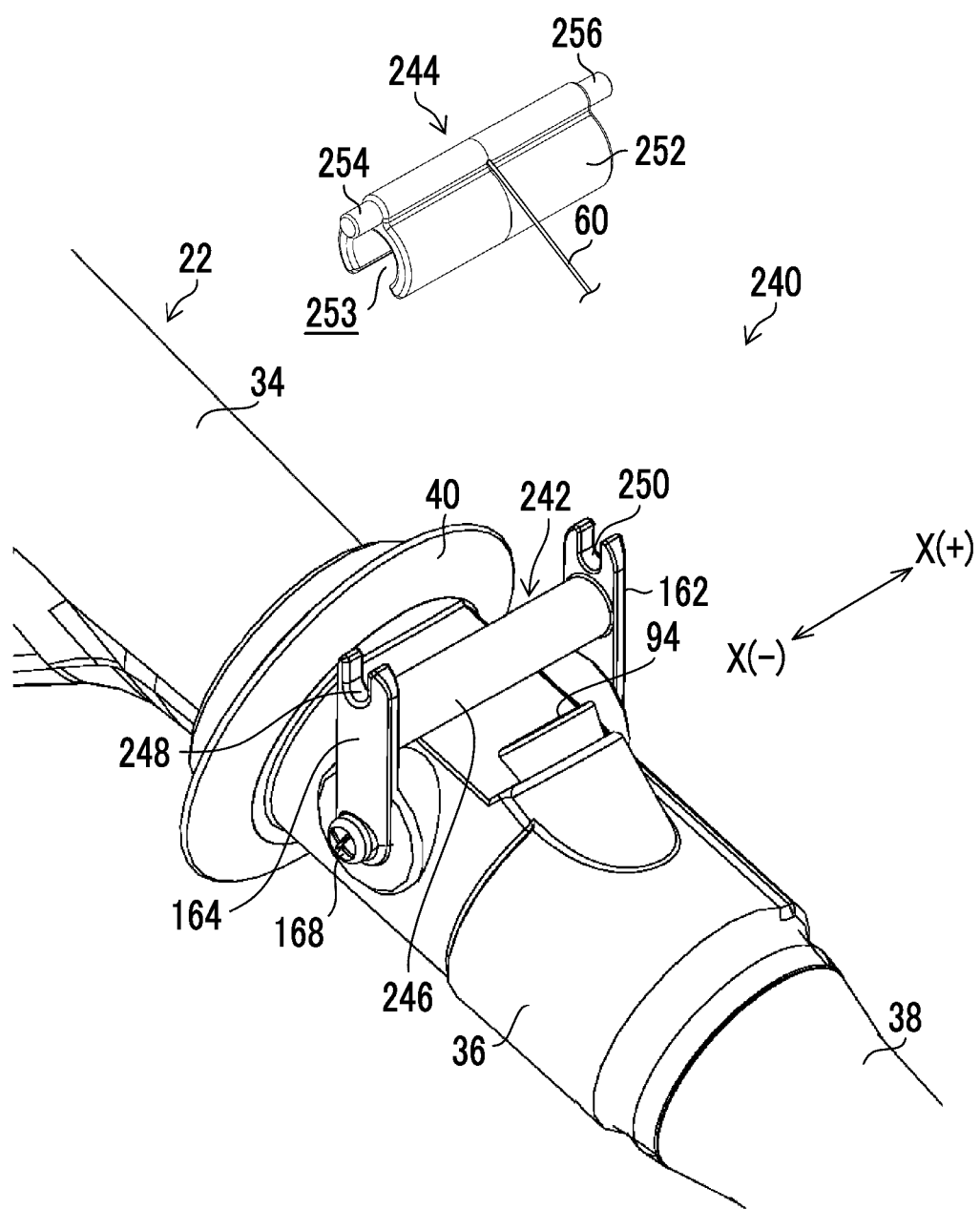
FIG. 40 is an exploded perspective view of the connection structure shown in FIG. 39.

FIG. 39 is a perspective view of the connection structure 240, and FIG. 40 is an exploded perspective view of the connection structure 210. In the description of the connection structure 240, the same members as the members of the connection structure 170 shown in FIGS. 11 to 18 or members similar to the members of the connection structure 170 will be denoted by the same reference numerals as the reference numerals shown in FIGS. 11 to 18.

The connection structure 240 includes a movable member 242 and a mounting member 244.

The movable member 242 includes a leg portion 162, a leg portion 164, and a cylindrical body 246 that connects the leg portion 162 to the leg portion 164. The cylindrical body 246 extends in a direction (X(+)-X(−) direction) perpendicular to the axial direction of the wire 60. Further, in FIGS.

39 and 40, U-shaped grooves 248 and 250 forming a rotation-regulating stopper are formed at the upper end portions of the leg portions 162 and 164.

The proximal end of the wire 60 is connected to the mounting member 244. The mounting member 244 includes an annular body 252 that is rotatably engaged with the outer periphery of the cylindrical body 246, and pins 254 and 256 that form the rotation-regulating stopper together with the grooves 248 and 250. The annular body 252 is formed to have a C-shaped cross section orthogonal to a longitudinal direction, and a slit 253 formed in the longitudinal direction is pressed against the cylindrical body 246, so that the annular body 252 is increased in diameter and is engaged with the cylindrical body 246 with one touch.

Even in the case of the connection structure 240 having this configuration, as in the case of the connection structures 170 and 210, work for attaching and detaching the mounting member 244 to and from the movable member 242 is performed outside the operation unit 22. For the work for mounting the mounting member 244, a user presses the slit 253 of the annular body 252 of the mounting member 244 against the cylindrical body 246 of the movable member 242. The mounting member 244 is engaged with the movable member 242 with one touch by this work. Accordingly, the proximal end of the wire 60 can be reliably connected to the movable member 242 through the mounting member 244.

Further, in a case where the annular body 252 is engaged with the cylindrical body 246, the pin 254 is engaged with the groove 248 and the pin 256 is engaged with the groove 250 at the same time with the engagement of the annular body 252. Accordingly, the rotation of the annular body 252 relative to the cylindrical body 246 can be prevented in a case where an operation for pushing or pulling the wire 60 is performed by the movable member 242. Therefore, an operation for pushing or pulling the wire 60 can be smoothly performed.

On the other hand, in a case where a user pulls the mounting member 244 in a direction where the pins 254 and 256 are detached from the grooves 248 and 250 in order to detach the mounting member 244 from the movable member 242 for the washing of the endoscope 10, the annular body 252 is pressed against the cylindrical body 246 and is increased in diameter. Accordingly, the annular body 252 is detached from the cylindrical body 246. As a result, the mounting member 244 is disengaged from the movable member 242 with one touch.

Therefore, according to the connection structure 240 shown in FIGS. 39 and 40, operations for attaching and detaching the proximal end of the wire 60 to and from the movable member 242 can be easily performed in comparison with the above-mentioned endoscopes disclosed in JP1994-315458A (JP-H06-315458A) and EP1759626B.

The movable member 242 has been provided with the cylindrical body 246 and the mounting member 244 has been provided with the annular body 252 in the embodiment, but any one of the movable member 242 or the mounting member 244 may be provided with the cylindrical body 246 and the other thereof may be provided with the annular body 252.

Even in the connection structure shown in FIGS. 30 to 40, the connection position between the movable member 96 and the rotating body 97 can be adjusted by the above-mentioned position adjustment member.

The wire 126 has been exemplified as an example of the drive member of the elevating operation mechanism 120 as shown in FIGS. 9 and 10 in the above-mentioned embodiment, but a link mechanism may be employed instead of the wire 126.

Figure 41:
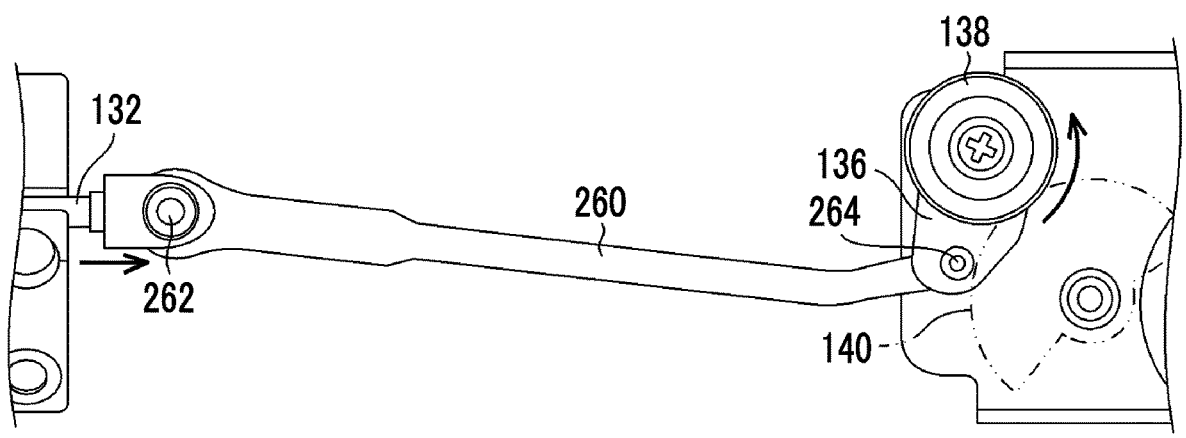
FIG. 41 shows a main structure where a first slider and a lever are connected to each other by a link sheet metal serving as a link mechanism.
Figure 42:
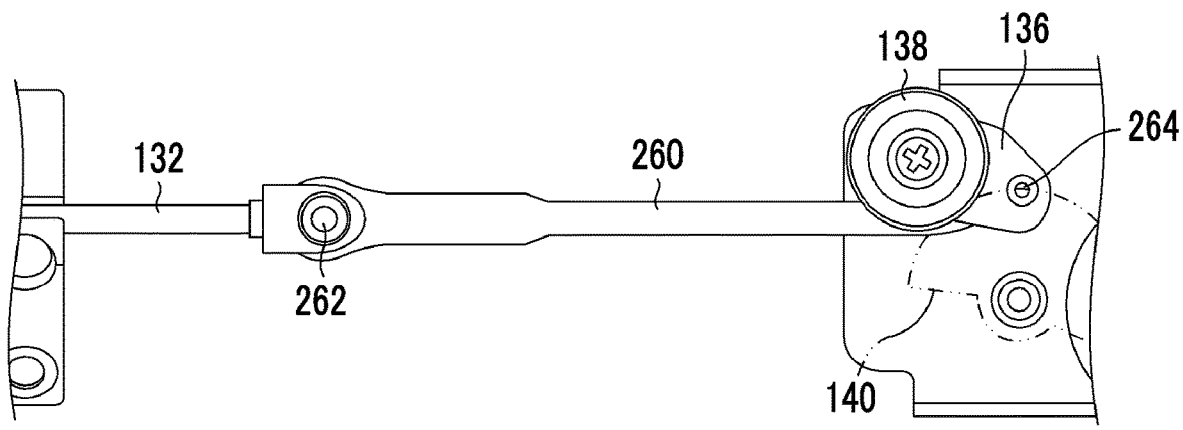
FIG. 42 is a diagram illustrating the operation of the link mechanism shown in FIG. 41.

FIG. 41 shows a main structure where a first slider 132 and a lever 136 are connected to each other by a link sheet metal 260 serving as a link mechanism. FIG. 42 is a diagram illustrating the operation of the link mechanism shown in FIG. 41.

As shown in FIGS. 41 and 42, the distal end of the link sheet metal 260 is rotatably connected to the proximal end of the first slider 132 through a pin 262 and the proximal end of the link sheet metal 260 is rotatably connected to the lever 136 through a pin 264.

Accordingly, in a case where the elevating operation lever 20 shown in FIGS. 9 and 10 is rotated, the linear motion of the first slider 132 can be transmitted to the lever 136 through the link sheet metal 260 that is the link mechanism. Therefore, since the lever 136 is rotated in the rotation range shown in FIG. 42 from FIG. 41, the torque of the lever 136 can be transmitted to the movable member 96 shown in, for example, FIGS. 9 and 10.

Further, a duodenoscope has been exemplified as the endoscope 10 in the embodiment. However, as long as an endoscope comprises, at a distal end part of an insertion unit, an elevator for adjusting the lead-out direction of a treatment tool, the invention can be applied to various endoscopes, such as an ultrasound endoscope.

EXPLANATION OF REFERENCES

10: endoscope
12: endoscope system
14: processor device
16: light source device
18: display
20: elevating operation lever
22: operation unit
22A: one side surface
22B: the other side surface
24: insertion unit
26: distal end part
28: distal end member
28A: peripheral surface
30: elevator
30A: guide surface
30B: base portion
32: operation unit body
34: grip part
36: extending part
38: bending-proof pipe
38A: proximal end portion
40: flange
42: treatment tool inlet
44: mount portion
44A: distal end portion
46: universal cord
48: electrical connector
50: light source connector
52: bendable part
54: soft part
56: treatment tool
56A: distal end portion
58: treatment tool channel
60: wire
62: wire channel
64: angle knob
66: air/water supply button 68: suction button
70: air/water supply nozzle
72: treatment tool outlet
74: outlet
76: cap
76A: open window
78: partition wall
78A: bearing portion
80: partition wall
80A: bearing portion
82: elevator-housing chamber
84: rotational movement shaft
86: rotational movement shaft
88: optical system-housing chamber
90: illumination window
92: observation window
94: inlet
95: valve element
96: movable member
96A: through hole
96B: recess
96C: grip portion
96D: inner peripheral groove
97: rotating body
97A: protruding portion
97B: outer peripheral groove
98: mounting member
98A: mounting member
100: engaging member
102: housing groove
104: opening
106: guide portion for engagement
108: guide passage for engagement
110: deformation generating portion
112: groove
114: groove
116: guide surface for disengagement
120: elevating operation mechanism
124: first conversion mechanism
126: wire
128: second conversion mechanism
130: crank member
132: first slider
134: second slider
135: connection mechanism
136: lever
138: first gear
140: second gear
142: third gear
144: fourth gear
146: bracket
148: shaft
150: shaft
152: drive shaft
154: fixing screw
156: fixing screw
157: fixing screw
158: fastening screw
159: cap
160: beam portion
160A: back
162: leg portion
164: leg portion
166: O-ring
168: driven shaft
170: connection structure
170A: connection structure
172: wire assembly
174: engaging hole
174A: engaging hole
175: edge portion
176: engaging portion
176A: engaging portion
177: cylindrical portion
178: core portion
180: hole portion
182: notch
184: elastically deformable portion
184A: slotted portion
186: claw portion
186A: claw portion
187: tapered portion
190: cap
200: branch pipe
202: distal end pipe
204: pipe line
206: pipe line
208: suction pipe
210: connection structure
212: mounting member
214: engaging hole
216: engaging portion
218: knob portion
220: shaft portion
222: hole portion
224: narrow portion
226: wide portion
228: enlarged-diameter portion
230: friction resistance portion
232: connection structure
234: mounting member
236: engaging portion
237: slotted groove
238: enlarged-diameter portion
240: connection structure
242: movable member
244: mounting member
246: cylindrical body
248: groove
250: groove
252: annular body
253: slit
254: pin
256: pin
260: link sheet metal
262: pin
264: pin

What is claimed is:

1. An endoscope comprising:
an operation unit that is provided with an operation member;
an insertion unit that is provided on a distal end side of the operation unit and is to be inserted into an object to be examined;
a treatment tool-elevator that is provided in a distal end part of the insertion unit;
a rotating body that is disposed to be exposed to an outside of the operation unit and operates in conjunction with an operation of the operation member;
a movable member comprises a movable beam and is attachably and detachably connected to the rotating body;

a position adjustment member that is capable of adjusting a connection position of the movable member in a rotation direction of the rotating body;

an elevating operation wire, of which a distal end side is connected to the treatment tool-elevator and a proximal end side is connected to the movable member and which causes the treatment tool-elevator to operate by being pushed or pulled according to an operation of the movable member; and a mounting member that comprises a plate and is provided at a proximal end of the elevating operation wire and is attachably and detachably engaged with the movable member, wherein the position adjustment member includes an outer peripheral groove that is provided on at least a part of the rotating body, a housing portion which is provided in the movable member and on which an inner peripheral groove to be engaged with the outer peripheral groove is formed, and a fixing screw that fixes positions of the rotating body housed in the housing portion and the movable member.

2. The endoscope according to claim 1, wherein the housing portion houses at least a part of the rotating body and the position adjustment member further includes a fixing screw that fixes positions of the rotating body housed in the housing portion and the movable member.

3. The endoscope according to claim 1, wherein any one of the movable member or the mounting member is provided with an engaging hole and the other thereof is provided with an engaging portion to be attachably and detachably engaged with the engaging hole.

4. The endoscope according to claim 3, wherein the engaging portion is provided with an elastically deformable portion that is elastically deformed to be engaged with the engaging hole.

5. The endoscope according to claim 4, wherein a pair of elastically deformable claw portions to be locked to an edge portion of the engaging hole is fall led at the elastically deformable portion, and the pair of claw portions is displaced so as to approach each other through elastic deformation in a case where the engaging hole and the engaging portion are engaged with each other or disengaged from each other.

6. The endoscope according to claim 1, further comprising:

an engaging member that is provided at a distal end of the elevating operation wire; and a housing groove that is provided in the treatment tool-elevator and is attachably and detachably engaged with the engaging member.

7. The endoscope according to claim 1, further comprising:

a proximal end opening that is provided in the operation unit;

a distal end opening that is provided in the distal end part; and an elevating operation wire channel that is provided in the insertion unit and allows the proximal end opening and the distal end opening to communicate with each other, wherein the elevating operation wire is inserted into the elevating operation wire channel, a distal end side of the elevating operation wire is connected to the treatment tool-elevator disposed outside the distal end opening, and a proximal end side of the elevating operation wire is connected to the movable member disposed outside the proximal end opening.

8. The endoscope according to claim 1, wherein the movable member is provided to be rotatable about a direction, which is perpendicular to an axial direction of the elevating operation wire, as a rotation axis.

9. The endoscope according to claim 8, wherein the operation member is an operation member that is rotatably supported on the operation unit, and the endoscope further comprises a first conversion mechanism that converts rotary motion of the operation member into linear motion, a drive member that is linearly driven by the first conversion mechanism, and a second conversion mechanism that converts linear motion of the drive member into rotary motion to rotate the movable member.

10. The endoscope according to claim 9, wherein the second conversion mechanism includes a speed reducer.

11. The endoscope according to claim 1, wherein the position adjustment member includes a grip portion that is provided at the movable member and grips at least a part of the rotating body and a fastening screw that fastens a distal end portion of the grip portion and fixes positions of the rotating body and the movable member.

12. The endoscope according to claim 4, wherein the engaging portion includes a cylindrical portion to be inserted into the engaging hole, and the elastically deformable portion is formed of a slotted portion provided at a distal end portion of the cylindrical portion, and the slotted portion is adapted to be elastically deformed to be capable of being reduced in diameter in a case where the distal end portion of the cylindrical portion is inserted into the engaging hole.

13. The endoscope according to claim 3, wherein the engaging hole includes a narrow portion having a first width and a wide portion having a second width larger than the first width, and the engaging portion includes a shaft portion that has an outer diameter equal to or smaller than the first width, and an enlarged-diameter portion that is provided at a distal end of the shaft portion and has an outer diameter larger than the first width and smaller than the second width.

14. The endoscope according to claim 4, wherein the engaging hole includes a narrow portion having a first width and a wide portion having a second width larger than the first width, and the engaging portion includes a shaft portion that has an outer diameter equal to or smaller than the first width, and an enlarged-diameter portion that fomis the elastically defoimable portion, is provided at a distal end of the shaft portion, has an outer diameter larger than the second width, and includes a plurality of slotted grooves, and the enlarged-diameter portion is adapted to be elastically deformed due to the plurality of slotted grooves to be capable of being reduced in diameter in a case where the enlarged-diameter portion is inserted into the wide portion.

15. The endoscope according to claim 14, wherein the engaging hole includes a friction resistance portion that is in contact with an outer peripheral surface of the shaft portion to apply frictional resistance to the shaft portion in a case where the shaft portion is moved between the narrow portion and the wide portion.

16. The endoscope according to claim 1,
wherein any one of the movable member or the mounting member is provided with a cylindrical body extending in a direction perpendicular to an axial direction of the elevating operation wire and the other thereof is provided with an annular body to be rotatably engaged with an outer periphery of the cylindrical body, and
the endoscope comprises a rotation-regulating stopper that regulates relative rotation of the cylindrical body and the annular body.

* * * * *